(12) United States Patent
Miller

(10) Patent No.: US 7,670,612 B2
(45) Date of Patent: Mar. 2, 2010

(54) MULTI-PHASE, MULTI-COMPARTMENT CAPSULAR DELIVERY APPARATUS AND METHODS FOR USING SAME

(75) Inventor: Fred H. Miller, Tampa, FL (US)

(73) Assignee: Innercap Technologies, Inc., Tampa, FL (US)

( * ) Notice: Subject to any disclaimer, the term of this patent is extended or adjusted under 35 U.S.C. 154(b) by 1159 days.

(21) Appl. No.: 10/804,576

(22) Filed: Mar. 19, 2004

(65) Prior Publication Data

US 2005/0008690 A1    Jan. 13, 2005

Related U.S. Application Data

(63) Continuation-in-part of application No. PCT/US03/10816, filed on Apr. 9, 2003.

(60) Provisional application No. 60/371,448, filed on Apr. 10, 2002.

(51) Int. Cl.
*A61K 9/48* (2006.01)
*A61K 9/14* (2006.01)

(52) U.S. Cl. .................. 424/400; 424/451

(58) Field of Classification Search .......... 424/451, 424/400
See application file for complete search history.

(56) References Cited

U.S. PATENT DOCUMENTS

| 3,072,528 A | 1/1963 | Kludas et al. |
| 4,185,740 A | 1/1980 | Perfect |
| 4,578,075 A | 3/1986 | Urquhart et al. |
| 4,606,909 A | 8/1986 | Bechgaard et al. |
| 4,627,808 A | 12/1986 | Hughes |
| 4,642,233 A | 2/1987 | Urquhart et al. |
| 4,681,583 A | 7/1987 | Urquhart et al. |
| 4,695,466 A | 9/1987 | Morishita et al. |

(Continued)

FOREIGN PATENT DOCUMENTS

DE    27 29 068 A1    1/1979

(Continued)

OTHER PUBLICATIONS

"Formulation Advantages: The hard gelatin capsule is a versatile container," The Hard Gelatin Capsule Advantage, BAS179-E-96, 1996, 3 pages.

(Continued)

*Primary Examiner*—Robert A Wax
*Assistant Examiner*—Aradhana Sasan
(74) *Attorney, Agent, or Firm*—Davidson, Davidson & Kappei, LLC; Clifford M. Davidson

(57) ABSTRACT

A multi-compartment capsule, comprising, a first receiving chamber comprising at least one ingredient having a first physical state, wherein said ingredient is selected from the group consisting of a nutraceutical, a vitamin, a dietary supplement and a mineral; and a second receiving chamber comprising at least one ingredient having a second physical state, wherein said ingredient is selected from the group consisting of a nutraceutical, a vitamin, a dietary supplement and a mineral; wherein said first physical state of said ingredient of said first receiving chamber being different from said second physical state of said ingredient of said second receiving chamber; and said ingredient of said first receiving chamber being different from said ingredient of said second receiving chamber.

111 Claims, 13 Drawing Sheets

U.S. PATENT DOCUMENTS

| | | | |
|---|---|---|---|
| 4,702,732 A | 10/1987 | Powers et al. | |
| 4,764,359 A | 8/1988 | Lemelson | |
| 4,773,907 A | 9/1988 | Urquhart et al. | |
| 4,793,493 A | 12/1988 | Makiej | |
| 4,808,413 A | 2/1989 | Joshi | |
| 4,822,619 A | 4/1989 | Eichel et al. | |
| 4,863,741 A | 9/1989 | Becker | |
| 4,904,476 A | 2/1990 | Mehta et al. | |
| 4,936,461 A | 6/1990 | Makiej | |
| 4,940,499 A * | 7/1990 | Lebrun et al. | 156/69 |
| 4,994,279 A | 2/1991 | Aoki et al. | |
| 5,017,379 A | 5/1991 | Lemelson | |
| 5,074,426 A | 12/1991 | Goodhart et al. | |
| 5,196,205 A | 3/1993 | Borody | |
| 5,256,684 A | 10/1993 | Marshall | |
| 5,310,555 A | 5/1994 | Zimmer | |
| 5,314,696 A | 5/1994 | Paulos | |
| 5,394,980 A | 3/1995 | Tsai | |
| 5,472,695 A | 12/1995 | Neeman et al. | |
| 5,472,708 A | 12/1995 | Chen | |
| 5,501,857 A | 3/1996 | Zimmer | |
| 5,558,878 A | 9/1996 | Paulos | |
| 5,560,912 A | 10/1996 | Neeman et al. | |
| 5,562,918 A | 10/1996 | Stimpson | |
| 5,576,019 A | 11/1996 | Paulos | |
| 5,582,837 A | 12/1996 | Shell | |
| 5,587,837 A | 12/1996 | Kebo | |
| 5,672,359 A | 9/1997 | Digenis et al. | |
| 5,674,530 A | 10/1997 | Amidon et al. | |
| 5,674,858 A | 10/1997 | McColm | |
| 5,738,871 A * | 4/1998 | Story | 424/451 |
| 5,750,143 A * | 5/1998 | Rashid et al. | 424/451 |
| 6,024,980 A | 2/2000 | Hoy | |
| 6,262,092 B1 | 7/2001 | Chang et al. | |
| 6,350,468 B1 | 2/2002 | Sanso | |
| 6,352,719 B1 | 3/2002 | Brown et al. | |
| 6,455,574 B1 | 9/2002 | Buch | |
| 6,486,182 B1 | 11/2002 | Chang et al. | |
| 6,517,866 B1 | 2/2003 | Am Ende et al. | |
| 6,528,809 B1 | 3/2003 | Thomas et al. | 250/573 |
| 6,569,152 B2 | 5/2003 | Brines et al. | |
| 6,620,806 B2 | 9/2003 | Day et al. | |
| 6,702,683 B2 | 3/2004 | Abrams et al. | 464/465 |
| 6,737,145 B1 | 5/2004 | Watanabe et al. | |
| 7,019,010 B2 | 3/2006 | Cohen | |
| 2002/0081333 A1 | 6/2002 | Oshlack et al. | |
| 2002/0094992 A1 | 7/2002 | MacLean | |
| 2002/0192277 A1 | 12/2002 | Oshlack et al. | |
| 2003/0035839 A1 | 2/2003 | Hirsh et al. | |
| 2003/0068369 A1 | 4/2003 | McAllister et al. | |
| 2003/0077297 A1 | 4/2003 | Chen | |
| 2003/0194428 A1 | 10/2003 | Miller et al. | |
| 2003/0194429 A1 | 10/2003 | Miller et al. | |
| 2003/0194430 A1 | 10/2003 | Miller et al. | |
| 2003/0194431 A1 | 10/2003 | Miller et al. | |
| 2005/0008690 A1 | 1/2005 | Miller | |

FOREIGN PATENT DOCUMENTS

| | | |
|---|---|---|
| EP | 0141373 A2 | 5/1985 |
| EP | 0211079 | 2/1987 |
| EP | 0228067 A2 | 7/1987 |
| EP | 0319318 A2 | 6/1989 |
| EP | 0325571 A1 | 7/1989 |
| FR | 1454013 | 9/1966 |
| FR | 2524311 | 4/1982 |
| GB | 2103564 A | 2/1983 |
| GB | 2353950 | 3/2001 |
| GB | 2365336 A | 2/2002 |
| JP | 60-193917 | 2/1985 |
| JP | 6211135 | 1/1987 |
| JP | 2000239159 * | 9/2000 |
| WO | WO 85/00015 | 1/1985 |
| WO | WO 89/03219 | 4/1989 |
| WO | WO 90/11129 | 10/1990 |
| WO | WO 92/06680 | 4/1992 |
| WO | WO 92/11848 | 7/1992 |
| WO | WO 93/00439 | 1/1993 |
| WO | WO 94/23770 | 10/1994 |
| WO | WO 95/10262 | 4/1995 |
| WO | WO 95/16438 | 6/1995 |
| WO | WO 96/02236 | 2/1996 |
| WO | WO 96/10996 | 4/1996 |
| WO | WO 99/30693 | 6/1999 |
| WO | WO 99/59413 | 11/1999 |
| WO | WO 00/28976 | 5/2000 |
| WO | WO 01/03676 | 1/2001 |
| WO | 0136290 | 5/2001 |
| WO | WO 01/32217 A2 | 5/2001 |
| WO | WO 02/07710 A2 | 1/2002 |
| WO | WO 02/11544 A1 | 2/2002 |
| WO | 02/96347 | 5/2002 |
| WO | WO 02/060384 A2 | 8/2002 |
| WO | WO 02/060385 A2 | 8/2002 |

OTHER PUBLICATIONS

"Producto de llenado de las capsulas," Todo sobre la capsula de gelatina dura, BAS126SP 1997, Capsugel Library, pp. 26-27 (4 pages).

"Fill material for hard gelatin capsules," All about the hard gelatin capsule, BAS126E 1999, Capsugel Library, pp. 26-27 (4 pages).

"The Hard Gelatin Capsule Advantage," Innercap Technologies Inc., 2004, pp. 2-9.

Michael Hopkin, "A healthy heart in a single pill," Nature News Service, Macmillan Magazines Ltd, Jun. 27, 2003, pp. 1 & 2.

Alexis Borisy, et al., "Systematic discovery of multicomponent therapeutics," PNAS, vol. 100, No. 9, Jun. 24, 2003, pp. 7977-7982.

Drug Delivery Technology, 2005, vol. 5, No. 9, pp. 40-86.

"Main Benefits of Liquid Fill Encap Drug Delivery" liquid fill encapsulation beats tablet alternative, http://www.encapdrugdelivery.com/benefits.html, 2003, 1 PG.

Scott Hensley, "Drug Makers 'Combos' Treat Two Disorders With One Pill," The Wall Street Journal, 2004, (Copyright © 2004, Dow Jones & Company, Inc.), pp. 1-3.

"FDA Approves Pfizer Medicine Caduet for the Treatment of Hypertension and High Cholesterol," FDA Approves Pfizer Medicine Caduet for the Treatment of Hypertension and High Cholesterol, http://www.medicalnewstoday.com/medicalnews.php?newsid=5666, Feb. 3, 2004, pp. 1-3.

Website print-out re: Capsugel Liquid Formulations in Licaps® Capsules.

Brochure by ONdrugDelivery Ltd. (2007).

Article from *Drug Delivery Technology Magazine*, vol. 5, No. 9, (Oct. 2005) pp. 40, 42, 44, and 46.

"Combination Products: Industry Strategies and Innovation Takes Combination Products to New Levels" *Drug Delivery Report Autumn/Winter 2005.*

"InnerCap Technologies Develops New Capsule Drug Delivery System" *Drug Delivery Technology Magazine*, vol. 4, No. 6 (Jul./Aug. 2004).

"Combo Pills Made Simple with Capsule Tech", (May 27, 2004), InPharma.com.

Coppola, Doreen R. "Multicompartment Capsules Prove Less is More" *Pharmaceutical Technology* (Jul. 2004) p. 16.

Brochure from InnerCap Technologies, Inc.

Advertisement by Health International Products, Inc.

Advertisement by Energy X Centric™.

Advertisement concerning Diet X Centric™.

Nutrex® product Lipo® 6X, Muscle Fitness® Magazine.

"The Hard Gelatin Capsule Advantage", Capsugel Advertisement (8 pages).

Action for Declaratory Judgment and Breach of Contract.

Action for Declaratory Judgment, Breach of Contract and Fraudulent or Negligent Inducement.

Innercap Technologies, Inc.'s Answer, Affirmative Defenses, and Counterclaims to Plaintiff Nutrex Research, Inc.'s Complaint.

Richardson, M., et al., Filing Two-Piece Hard Gelatin Capsules with Liquids, Jan. 2008.

Partial translation of JP Utility Model Publication (Kokai) No. 62-011135 A (1987).

* cited by examiner

MULTI-PHASE, MULTI-COMPARTMENT CAPSULAR DELIVERY APPARATUS AND METHODS FOR USING SAME

RELATED APPLICATIONS

This Application is a continuation-in-part of PCT/US/03/10816 filed Apr. 9, 2003, and entitled "MULTI-PHASE, MULTI-COMPARTMENT CAPSULAR SYSTEM", the contents of which are hereby incorporated by reference in their entirety. This application incorporates herein by reference U.S. Provisional Application Ser. No. 60/371,448, filed Apr. 10, 2002, and entitled "INTEGRATED CAPSULE DELIVERY APPARATUS AND METHOD." This application further claims the benefit of U.S. patent application Ser. No. 10/369,427, filed Feb. 18, 2003, entitled "MULTI-PHASE, MULTI-COMPARTMENT CAPSULAR DELIVERY APPARATUS AND METHODS FOR USING SAME," which is hereby incorporated herein by reference. This application further claims the benefit of U.S. patent application Ser. No. 10/368,951, filed Feb. 18, 2003, entitled "PROCESS FOR ENCAPSULATING MULTI-PHASE, MULTI-COMPARTMENT CAPSULES," which is hereby incorporated herein by reference. This application further claims the benefit of U.S. patent application Ser. No. 10/369,244, filed on Feb. 18, 2003, and entitled "MULTI-PHASE, MULTI-COMPARTMENT CAPSULAR DELIVERY APPARATUS FOR THERAPEUTIC COMPOSITIONS AND METHODS FOR USING SAME," which is hereby incorpoated herein by reference. This application further claims the benefit of U.S. patent application Ser. No. 10/369,247, filed Feb. 18, 2003, and entitled "PROCESS FOR ENCAPSULATING MULTI-PHASE, MULTI-COMPARTMENT CAPSULES FOR THERAPEUTIC COMPOSITIONS," which is hereby incorporated herein by reference.

BACKGROUND

1. The Field of the Invention

The present invention relates to delivery of active ingredients or medicaments and, more particularly, to novel capsular delivery apparatus and methods for delivering one or more active ingredients or medicaments having diverse physical states (e.g., solid, liquid, gas or dispersion) into a single dosage, multi-compartment capsule.

The present invention further relates to methods for the administration of a plurality of heterogenous chemical and biological compounds to animals and humans using a multi-compartment delivery system for treatment of different conditions or the same condition or diseases (different or same) in one or more organ systems.

2. Background of the Invention

As appreciated by those skilled in the art, the contemplation, design, testing and manufacture of chemicals and biomolecules for administration to humans and animals, as nutritional or therapeutic agents, requires a thorough integration of clinically contemplated delivery principles and modalities. Chemicals and biomolecules that may be administered to humans and animals are often referred to herein as "actives," "active ingredients" or "medicaments."

Oral administration has become one of the most frequent routes for delivering one or more active ingredients or medicaments to the body. Active ingredients or medicaments, such as nutritional or therapeutic agents, may be orally administered in a variety of physical states (i.e., solid, liquid or gas). Tablets and capsules are generally the most common vehicle for the oral delivery of medicaments. As appreciated, a tablet may be broadly characterized as a compressed powder or granular solid. Prior to compression of the granular powder comprising the medicament into tablet form, the presence of one or more excipients may be required. An excipient includes any inert substance (i.e., gum arabic, starch or the like) combined with a principal ingredient to facilitate the preparation of an agreeable or convenient dosage form of the active or medicament. Functional characteristics of excipients may include, for example, disintegration, lubrication, appearance, palatability, shelf-stability or the like.

Those skilled in the art also developed capsules as a contrivance for containing a solid or liquid dosage form of a medicament. Traditional capsular embodiments include a first containment section referred to as a base, and a second containment section referred to as a cap. The two pieces of the capsule are usually formulated and designed in a manner such that the material to be encapsulated may be introduced into the base section, whereas the open end of the cap section may be correspondingly positioned over the open end of the base. The walls of the cap and base are generally in physical contact with one another to form a single internal cavity. A means for structurally sealing the cap in relation to the base may also be incorporated during manufacture to insure non-tampering of the capsule. In this regard, those skilled in the art developed sealing technology which contemplates banding, heat fusion (spot-welding) and snap seals which utilize a "tongue and groove" scheme.

The outer walls of a capsule are preferably formed of a soluble ingredient, such as, for example, gelatin (animal-based product), starch, hydrophillic polymer or hydroxypropyl methyl-cellulose (HPMC), which provides a barrier for containing the active ingredient or medicament, in powder or liquid form, within the internal periphery of the capsule walls. Traditionally, hard gelatin capsules may be manufactured by dipping plates of stainless steel pins into a pool of gelatin solution. The pins are then removed from the gelatin and rotated while the gelatin is dried in a kiln with forced, humidity-controlled air. Once dried, the gelatin capsules are typically stripped from the pins, trimmed to a suitable length and then joined together (e.g., base and cap) and packaged for production use.

With the advent of automated encapsulation machinery, the responsibility to produce encapsulated products shifted mainly to industrial manufacturers. Contemporaneous with the development of the encapsulation industry, those skilled in the art have advanced the state of the encapsulation art. For example, several significant improvements in encapsulation technology have been seen over the last forty years. These technological improvements have included, for example, the development of soft elastic capsules, film-coating techniques, micro-encapsulation and multiple-compartment technology.

Soft elastic capsules, often referred to as soft gelatin capsules, were developed in an effort to provide means for encapsulating liquids and other medicaments which are typically poorly soluble in water. In preferred design, soft elastic capsules are made from a thicker and more plastic gelatin having an increased flexibility due to the addition of a polyol, such as glycerin or sorbitol. The addition of such plasticizers has been found, however, to have the potential disadvantage of increasing the risk for microbial growth. Thus an antimicrobial, such as a paraben or sorbic acid, may be added to the soft elastic capsule shell in order to address any microbial concern.

Prior art film-coating techniques generally involve a plating process, whereby a thin, uniform film may be deposited onto the outer surface of the delivery vehicle (e.g., tablet or capsule). Several successive layers may be deposited onto the outer surface of the vehicle, if desired, in an effort to facilitate various desirable properties. For example, sugar-coating, a precursor to film-coating, has been used by those skilled in the art for more than one hundred years to make tablets more palatable. Other advantages or properties of film-coating may include for example, but not by way of limitation, protection from moisture, oxidation, controlling microbial contamination and inhibiting modification of the chemical properties of the active ingredient. As further appreciated by those skilled in the art, prior art film-coating may form an interfacial barrier between two chemicals or chemical compounds that might otherwise react when they come into contact.

Enteric coatings and sustained-release formulations are contemplated as variations on prior art film-coating techniques. In particular, enteric coating describes a process where the delivery vehicle (e.g., tablet or capsule) is coated with one or more layers of chemicals that are somewhat resistant to extreme pH conditions. For example, conditions of extremely low pH are commonly encounter in the stomach. Many active ingredients or medicaments are in the form of a pharmaeceutical salt and thus highly susceptible to ionization in the presence of hydrogen ions. Thus, the presence of an enteric coating generally provides a level of protection as to degradation of the active ingredient or medicament until transit from the stomach into the small intestine is accomplished.

Film coatings have also led to the development of delivery vehicles (e.g., tablets and capsules) having sustained-release properties. Mixtures of waxes, cellulose, silicone and similar resins have been found useful by those skilled in the art for creating-sustained release coatings. In principle, these prior art coatings function to delay the release of the active ingredient or medicament to the targeted body system, thereby facilitating a timed, absorption rate in the body. Furthermore, the entire daily dosage of an active or medicament may be contained in a single, sustained-release delivery vehicle (e.g., tablet or capsule), whereas the immediate absorption of the entire dosage could possibly lead to an overdosage of the medicament. Thus, by layering quanta of medicament with differential coatings, the dosage undergoes a controlled release over specified time period. The application of sustained-release film coating technology therefore may inherently facilitate the delivery of a total daily dosage amount of an active or medicament to be released to the body in controlled increments.

Over the last several years, a considerable amount of attention has been focused on the further development of multi-compartment capsule technology for the delivery of therapeutic and diagnostic agents. Series formulations teach the use of membranes or other types of barriers to cordon a line of separate chambers within a single encapsulating shell. As appreciated, the purpose of such multi-compartment delivery devices is the administration of multiple dosages. Moreover, multiple-compartment delivery mechanisms of the prior art were developed to circumvent or diminish the effects of harsh pH environments within humans. For example, the prior art contemplates a hard capsule formulation which contains three different compartments of active medicaments for administration to the vaginal and rectal areas. In preferred structure, the formulation outer, rapid-release layer may contain an active medicament and excipient; the middle, intermediate-release layer may include a powder form of active medicament; and the inner, slow-release layer may contain pellets or granules of active medicament.

Also taught in the prior art are multi-compartment capsules having groups of spheroids with pH-dependent coatings which are encapsulated within a hard gelatin shell and provided for treating female yeast infection. The first spheroid is preferably uncoated and may be in a powder form; the second spheroid may contain a pH sensitive coat; and the inner spheroid may include a pH insensitive coat.

In addition to pH-sensitive coatings, hydrogels and other gastric retention technologies have been developed by those skilled in the art in an effort to retard the progression of the delivery vehicle during enteric transit. This retarding action, presumably, allows the full amount of active medicament to be released and/or targeted to a specific area of the gastrointestinal tract. Hydrogel and related gastric retention devices of the prior art generally rely upon the imbibing of water into a center core which is filled with cellulose or similar water absorbent material. In preferred operation, the material swells and releases multiple compartments of active medicament. The concept of using bulk size to slow transit of single active medicament in a single physical state is thus appreciated.

In an effort to administer active ingredients or medicaments to a specific location in the body to treat a specific disorder caused by a specific pathogen, those skilled in the art have used targeted-release systems using multi-compartment capsular technology. For example, a method for carrying out a triple therapy against the microorganisms *Helicobacter pylori*, a known infectious agent which is believed largely responsible for the development of gastric ulcer disease, was developed which comprises the steps of oral administration of a pharmaeceutical dosage form comprising an internal capsule placed inside an external capsule, wherein the external capsule comprises a soluble salt of bismuth and a first antibiotic, and the internal capsule comprises a second antibiotic. In addition, multi-compartmental capsules were developed which combine a nutrient supplement with a viable direct-fed microbial (i.e., gastrointestinal microorganisms, including bacteria, live cell yeasts, fungi or a combination thereof) for the purpose of treating livestock for feeding disorders and improving feed efficiency.

A disadvantage with prior art encapsulation technology is when the base and corresponding cap of a capsule are joined, dead space volume is typically created within the internal periphery of the capsule. Internal capsular dead space may be filed with an air bubble which may ultimately react with one or more of the active ingredients or medicaments introduced within the capsule, thereby potentially degrading the quality and effectiveness of the active ingredients.

Although the prior art discloses multiple compartment, capsular delivery technology, these manifestations generally includes one of two approaches. For example, one approach contemplates the introduction of a single active or medicament into multiple capsular compartments to vary the temporal release of the medicament and ultimately the absorption rate into the body. Another approach contemplates the introduction of a plurality of active ingredients or medicaments into different compartments of a single capsule for delivery to a specific area of the body to treat a targeted illness or condition.

The use or contemplation of multiple-compartment capsular delivery apparatus or methods which deliver different physical forms of the same active or medicament, or a variation in physical forms of different actives or medicaments in a single dosage, however, has not heretofore been contemplated in the art. As appreciated by those skilled in the art, active ingredients or medicaments may take the physical form of a solid (e.g., pill, tablet, capsule (both hard and soft elastic), powder, granulation, flakes, troches (lozenges and pastilles), suppositories and semi-solid ointments, pastes, emulsions and creams), a liquid (e.g., solution, spirits, elixir, syrups, sprays and fluid extracts), a gas or a dispersion. A dispersion is a system in which a dispersed phase is distributed through a continuous phase (e.g., aerosols (liquid or solid in gas), suspensions (solid in liquid), emulsion (liquid in liquid), foam (gas in liquid), solid foam (solid in gas) or gel (liquid or solid in solid)). Dispersions can be classified as molecular, colloidal and coarse, depending on size. In many circumstances, however, the different physical forms or phases of more than one active ingredient or medicament may not be suitably combined or mixed together without altering the individual desirable properties of the active ingredient or medicament. For example, although it would be possible and desirable to formulate a dispersion by combining a first active ingredient in the solid state with a second active ingredient that exists as a liquid, adverse chemical interactions between the active ingredients may adversely affect various characteristics of the ingredients, including but not limited to, their shelf lives. The resulting chemical decomposition—and the potential formation of any unwanted side products—could result in diminished drug potency or even toxicity to a patient.

Additionally, the physical properties of crystalline active ingredients could be drastically altered in scenarios where it is desirable to co-administer a crystalline active ingredient with a liquid or semi-liquid different active ingredient. In this context, the control of physical properties such as active ingredient dissolution rate and solubility is often a critical factor in determining the overall bioavailability of the active ingredient. It is well established in the art that different polymorphs or solvates of the same crystalline active ingredient exhibit dramatically different solubility and dissolution rates. Thus, combining a crystalline active agent with a liquid or semi-liquid active agent could give rise to an equilibrium between concentrations of different polymorphs and/or solvates of the crystalline active ingredient, and thereby frustrate efforts at tailoring an active ingredient mixture to its intended purpose as a medicament.

Another shortcoming with co-administering plural active ingredients in different physical forms in an intimate mixture is the potential for adverse in vivo drug-drug interactions upon administration. The desire to co-administer these active ingredients would be offset by the one active ingredient, for example as in a liquid or semi-liquid (e.g., a paste, solution, or syrup) form, becoming rapidly available. In this context, the active ingredient may adversely react with a co-administered drug, for example a less bioavailable solid or semi-solid, in a physiological environment. Thus, the true therapeutic benefit resulting from the pharmacological effects of the individual active agents may never be realized. It would be desirable to co-administer plural active ingredients while insuring against the potential of such harmful drug-drug interactions.

Providing active ingredients or medicaments in separate capsules may also be undesirable in the context of patient compliance. Geriatric and pediatric populations in particular disfavor the handling and consumption of multiple capsules of active ingredients. Patient compliance is essential in maintaining patient health in many dosage regimens. For example, deviations from accurate dosing and consistent consumption of immunosuppressant therapies can result in severe or even lethal consequences for a patient. Providing combined dosages of active ingredients would result in fewer capsules a patient or consumer would have to take, and thereby contribute to an overall increase in compliance.

Therefore, it would be desirable to provide a multi-compartment capsular delivery apparatus and methods that provide active ingredients or medicaments having diverse physical properties (e.g., solid, liquid, gas or dispersion), which may or may not be properly combined or stored together into a unitary structure (i.e., multi-compartment capsule) for usage in a single dosage form. The present invention, in overcoming the shortcomings of the prior art, satisfies these and other objectives.

The art and practice of pharmacy can be divided into four distinct divisions. Pharmacology is the study of interactions occurring between the pharmacologic agent, or medicament and specific targeted cells in the body. More specifically, the interaction between an active agent and a cellular receptor along with the resulting change in cell physiology is examined. Medicinal chemistry is largely concerned with the identification of naturally occurring and synthetic compounds which possess medicinal characteristics.

Pharmacotherapeutics is the holistic application of pharmacy practice to specific pathologies, illnesses, and other body functions. Finally, Pharmaceutical science ascertains or regulates the composition of medicinal substances, and is largely directed to the development of new mechanisms for delivering chemicals and biomolecules into animals and humans. A subcategory of pharmaceutical science is called pharmacokinetics and sometimes generally referred to as biopharmaceutics.

A.D.M.E. is an acronym often used to describe the four essential components to pharmaceutical science: absorption, distribution, metabolism, and elimination, respectively. One way to differentiate between pharmacology and pharmaceutical science is that the former is primarily concerned with the effect of the medicament on the body, whereas, the latter is primarily concerned with the delivery and time-course of the medicament on its journey through the body.

In clinical applications, chemicals and biomolecules are often referred to as active ingredients or medicaments. Medicaments may include "pharmaceuticals, nutraceuticals, biotechnicals, vitamins, minerals and dietary supplements." Oral administration is the most frequent route for delivery of medicaments. Medicaments may be orally administered in a variety of physical states, including, solid, liquid, dispersion, and gaseous forms. As appreciated, tablets and capsules are the most common vehicle for oral delivery of medicaments.

Frequently, a medical or surgical patient may receive a plurality of concurrent medicaments. Data has been accumulated to demonstrate that patients undergoing a surgical procedure may receive ten (10) or more medicaments during the surgery and the resulting surgical recovery period. Some patients who have undergone organ transplantation or who have contracted human immunodeficiency virus (HIV) may receive three (3) or more medicaments which require multiple administrations per day. HIV patients often receive many more than three (3) medicaments. These medicaments may be necessary for the treatment of several conditions occurring in a plurality of organ systems or they may be necessary to treat a single condition or some combination thereof.

In some cases, it may be desirous to combine a plurality of medicaments because of a synergistic interaction between a plurality of medicaments. This synergy may enhance the efficacy of one or more of the medicaments. Medicaments may be combined to increase the intensity of response or efficacy. A plurality of medicaments, in combination, may be homergic (i.e., ellicit the same quality of effect). In many cases, a plurality of homergic medicaments may also be homodynamic (i.e., interact with the same receptor). A plurality of homergic medicaments may be additive, supra-additive and infra-additive. A plurality of combined medicaments which do not produce the same quality of response may be called, heterergic. When heterergy is found to be a positive effect (i.e., at least one medicament enhances the response to another medicament), this may be called synergism and is sometimes called synergy.

In further cases, it may be desirous to combine a plurality of medicaments to decrease their individual dosages and possibility for toxicity. It may also be desirous to combine a plurality of medicaments to target the treatment of a disease, illness or condition from divergent angles. It may be desirous to combine a plurality of medicaments to minimize the side effects and adverse effects of one or more medicaments. It may be still further desirous to combine a plurality of medicaments to alter the pharmacokinetic characteristics of one or more medicaments. For example, alterations in the absorption, distribution, metabolism or elimination of one or more medicaments.

Fixed combinations of a plurality of medicaments have been generally disfavored due to any number of perceived disadvantages. These disadvantages may include, for example: (1) complicating the interpretation of safety and efficacy in therapeutic regimens, (2) there may be inter-patient differences to fixed combinations, (3) there may be difficulties in dosage titration, and (4) the delivery platforms for fixed combinations have generally been found to be uneconomical to produce.

On the other hand, fixed combinations of a plurality of medicaments may lead to several therapeutic advantages, including, for example, but not by way of limitation: (1) increasing patient compliance with therapy, (2) increasing efficacy by optimizing timing of medicaments, (3) minimization of side effects and adverse effects, (4) enhancement of pharmacokinetic characteristics of one or more medicaments in a fixed combination, (5) increased patient quality of life, (6) optimization of institutional resources by minimizing the amount of medicament administrations, and (7) minimizing patient length of stay in institutional facilities by optimizing therapy.

Prior art therapeutic technologies contain isolated examples of pharmaceutical formulations containing fixed combinations of medicaments. However, therapeutic technologies of the prior art teach a fixed combination, wherein a plurality of medicaments are placed into a single receiving chamber in the delivery formulation (i.e., no separation between the plurality of medicaments).

In view of the state of the technology as it exists today, generally, therapeutic apparatus and methods are needed to provide a plurality of medicaments for medical and surgical conditions, as well as maintenance of normal health function for delivery to animals and humans using a multi-chambered delivery apparatus. Such apparatus and methods for delivering a plurality of medicaments to animals and humans using a multi-chambered delivery apparatus are contemplated herein.

BRIEF SUMMARY AND OBJECTS OF THE INVENTION

In view of the foregoing, it is a primary object of the present invention to provide novel integrated capsule delivery apparatus and methods for delivering diverse physical states (e.g., solid, liquid, gas or dispersion) of a single active ingredient or medicament, or a plurality of active ingredients or medicaments, in a single dosage form, wherein at least two of the active ingredients or medicaments have physical states that differ.

It is also an object of the present invention to provide novel integrated capsule delivery apparatus and methods which facilitate various desirable properties including, for example, controlling time-release of key active ingredients or medicaments, prolonging shelf-life of the active ingredients or medicaments, improving palatability, reducing overall production costs and, accordingly, reducing the number of capsules consumed by a patient or consumer as nutritional or therapeutic agents.

Further, it is an object of the present invention to provide novel integrated capsule delivery apparatus and methods for delivering one or more active ingredients or medicaments (e.g., pharmaeceutical, biotechical, nutraceutical, vitamin, dietary supplement, mineral or combination thereof) in the form of a single dosage, multi-compartment capsule having one or more active ingredients in a primary capsule, and one or more active ingredients introduced into a secondary smaller capsule having a size sufficient for being selectively positionable within the primary capsule, wherein the active ingredient(s) within the primary capsule comprises a physical state (e.g., solid, liquid, gas or dispersion) that is different from the physical state of the active ingredient(s) in the secondary capsule.

It is an additional object of the present invention to provide novel integrated capsule delivery apparatus and methods for delivering one or more active ingredients or medicaments (e.g., pharmaeceutical, biotechnical, nutraceutical, vitamin, dietary supplement, mineral or combination thereof) in the form of a single dosage, multi-compartment capsule having one or more active ingredients in a primary capsule and the same active ingredient(s) introduced into a smaller secondary capsule having a size sufficient for being positionable within the primary capsule, wherein the active ingredient(s) in the primary capsule comprises a physical state (e.g., solid, liquid, gas or dispersion) different from the active ingredient(s) in the secondary capsule.

It is a further object of the present invention to provide novel integrated capsule delivery apparatus and methods for delivering one or more active ingredients or medicaments (e.g., pharmaeceutical, biotechnical, nutraceutical, vitamin, dietary supplement, mineral or combination thereof) in the form of a single dosage, multi-compartment capsule wherein at least one of the primary and secondary capsules include a time-release coating for controlling the release of the active ingredient(s) contained therein.

It is also another object of the present invention to provide novel integrated capsule delivery apparatus and methods for delivering one or more active ingredients or medicaments (e.g., pharmaeceutical, biotechnical, nutraceutical, vitamin, dietary supplement, mineral or combination thereof) in the form of a single dosage, multi-compartment capsule having one or more active ingredients in the capsular body, wherein the capsule includes a longitudinally extending body and at least one dividing wall formed along a length of the extending body to form a first chamber and an opposing second chamber within the capsular body and introducing at least one active ingredient or medicament having a first physical state into the first chamber and at least one active ingredient or medicament having a second physical state into a second chamber, whereas the physical state (e.g., solid, liquid, gas or dispersion) of the ingredient(s) in the first chamber is different from the physical state of the ingredient(s) in the second chamber.

It is an additional object of the present invention to provide novel integrated capsule delivery apparatus and methods for delivering one or more active ingredients or medicaments (e.g., pharmaeceutical, biotechnical, nutraceutical, vitamin, dietary supplement, mineral or combination thereof) in the form of a single dosage, multi-compartment capsule having a longitudinally extending body and one or more dividing walls disposed along the length of the longitudinally extending body of the capsule, wherein the capsule and one or more of the dividing walls contained therein may include time-release coatings for controlling the release of the active ingredients or medicaments contained therein, respectively.

It is a further object of the present invention to provide novel integrated capsule delivery apparatus and methods for delivering one or more active ingredients or medicaments (e.g., pharmaeceutical, biotechnical, nutraceutical, vitamin, dietary supplement, mineral or combination thereof) in the form of a single dosage, multi-compartment capsule having a plurality of active ingredients or medicaments having the physical form of a solid (e.g., pill, tablet, capsule (both hard and soft elastic), powder, granulation, flakes, troches (lozenges and pastilles), suppositories and semi-solid ointments, pastes, emulsions and creams), a liquid (e.g., solution, spirits, elixir and fluid extracts), a gas or a dispersion (e.g., aerosols (liquid or solid in gas), suspensions (solid in liquid), emulsion (liquid in liquid), foam (gas in liquid), solid foam (solid in gas) or gel (liquid or solid in solid), wherein the physical form of the active ingredients differ between a primary and secondary capsule, and between one or more dividing walls disposed in spaced-apart relationship along the length of a longitudinally extending capsular body.

It is a still further object of the present invention to provide novel integrated capsule delivery apparatus and methods for delivering one or more active ingredients or medicaments (e.g., pharmaeceutical, biotechnical, nutraceutical, vitamin, dietary supplement, mineral or combination thereof) in the form of a single dosage, multi-compartment capsule, wherein an encapsulation process comprises the steps of: (1) providing a capsule comprising a first end, a second end, a longitudinally extending body having a length disposed between the first and second ends, and a plurality of dividing walls spaced apart along the length of the extending body, wherein the dividing walls form a plurality of receiving chambers; (2) introducing at least one active ingredient having a first physical state into a first receiving chamber; (3) introducing at least one active ingredient having a second physical state into a second receiving chamber; (4) introducing at least one active ingredient having a third physical state into a third receiving chamber, wherein the physical states of at least two of the active ingredients introduced into the first, second or third receiving chambers differ; and (5) sealing the first and second ends of said capsule.

Additionally, it is an object of the present invention to provide novel integrated capsule delivery apparatus and methods for delivering a single dosage, multi-compartment capsule comprising a capsular base and cap configuration, wherein the size and shape of the cap, relative to its sealing relationship with the base, generally eliminates or substantially reduces any potential dead space volume within the internal periphery of the capsule, thereby functionally negating the opportunity for reaction between an air bubble and one or more active ingredients introduced into the capsule and, accordingly, improving stability of the capsular ingredient(s).

Consistent with the foregoing objects, and in accordance with the invention as embodied and broadly described herein, one presently preferred embodiment of the novel integrated capsule delivery apparatus and methods of the present invention comprises a multi-compartment capsule including a primary capsule and a secondary capsule selectively positionable within an internal periphery of the primary capsule. The secondary capsule may include a base, a corresponding cap and one or more receiving chambers. Each of the receiving chambers of the secondary capsule may be formed having an internal periphery sufficient for receiving at least one active ingredient or medicament (e.g., pharmaeceutical, biotechnical, nutraceutical, vitamin, dietary supplement, mineral or combination thereof) therein. Similarly, the primary capsule may be formed having a base, a corresponding cap and one or more receiving chambers. The receiving chambers of the primary capsule may be formed having an internal periphery sufficient for receiving the secondary capsule and one or more active ingredients or medicaments (e.g., pharmaeceutical, biotechnical, nutraceutical, vitamin, dietary supplement, mineral or combination thereof) having a physical state (i.e., solid, liquid, gas or dispersion) different from the physical state of the active ingredient(s) housed within the receiving chamber of the secondary capsule.

As further contemplated herein, a multi-compartment capsule is provided comprising a base, a corresponding cap and one or more dividing walls positionable between the base and the cap. Structurally, the size, shape and positioning of the dividing walls relative to the base and corresponding cap facilitates the formation of at least two, independent and separate receiving chambers. Each of the receiving chambers having an internal periphery sufficient for receiving one or more active ingredients or medicaments (e.g., pharmaeceutical, biotechnical, nutraceutical, vitamin, dietary supplement, mineral or combination thereof) therein. In preferred design, the physical state (e.g., solid, liquid, gas or dispersion) of the active ingredient(s) in the first receiving chamber is different from the physical state of the active ingredient(s) in the second receiving chamber. After introducing one or more active ingredients or medicaments into each receiving chamber, the cap may be selectively positioned in sealing relationship with the base to form one presently preferred embodiment of the single, dosage multi-compartment capsule.

One presently preferred embodiment of an encapsulation process for forming a multi-compartment capsule may comprise the steps of: (1) providing a primary capsule having a base, a corresponding cap and a receiving chamber; (2) providing a secondary capsule having a base, a corresponding cap and a receiving chamber; (3) introducing at least one ingredient or medicament (e.g., pharmaeceutical, biotechnical, nutraceutical, vitamin, dietary supplement, mineral or combination thereof) having a first physical state (e.g., solid, liquid, gas or dispersion) into at least a portion of the receiving chamber of the secondary capsule and selectively positioning the cap in sealing relationship with the base; (4) introducing at least one ingredient or medicament (e.g., pharmaeceutical, biotechnical, nutraceutical, vitamin, dietary supplement, mineral or combination thereof) having a second physical state (e.g., solid, liquid, gas or dispersion) into at least a portion of the receiving chamber of the primary capsule, wherein the first physical state of the ingredient(s) in the secondary capsule is different from the second physical state of the ingredient(s) in the primary capsule; and (5) introducing the secondary capsule into at least a portion of the receiving chamber of the primary capsule and selectively positioning the cap in sealing relationship with the base to form a single dosage multi-compartment capsule.

In alternate presently preferred embodiments of the present invention, a tertiary capsule comprising a base, a corresponding cap and a receiving chamber having an internal periphery sufficient for receiving one or more active ingredients or medicaments (e.g., pharmaeceutical, biotechnical, nutraceutical, vitamin, dietary supplement, mineral or combination thereof) may be selectively introduced within an internal periphery of at least one receiving chamber of the secondary capsule. After the introduction of at least one active ingredient into one or more receiving chambers of a tertiary capsule pursuant to an encapsulation process of the present invention, the cap of the tertiary capsule may be selectively positioned in sealing relationship with the base and then introduced into at least a portion of the internal periphery of the secondary capsule, together with one or more active ingredients therein. It is contemplated herein that at least two of the active ingredients introduced within the receiving chambers of the primary, secondary and tertiary capsules, respectively, comprise at least two different physical states (e.g., solid, liquid, gas or dispersion).

In preferred structural design, the primary capsule may comprise a cap having a generally U-shaped configuration adapted to provide a sealing relationship when engaging the corresponding base, thereby reducing dead space volume in the internal periphery of the cap and receiving chamber of the base. A cap having a configuration adapted to generally eliminate or substantially reduce potential dead space volume of the cap and receiving chamber of the base may, accordingly, function to negate the potential for a reaction between an air bubble and one or more active ingredient(s) introduced into the base of the primary capsule.

Alternatively, a multi-compartment capsule of the present invention may include the introduction of a filling material into the cap of the primary capsule, the cap having a general cylindrical configuration adapted to provide a sealing relationship when engaging the corresponding base. An amount of filling material may be introduced into at least a portion of the internal periphery of the cap to fill, either partially or completely, the inner volume of the cap, thereby reducing the dead space volume in the cap and the internal periphery of the receiving chamber of the base. In this regard, the introduction of a filling material relative to the internal periphery of the cap may generally eliminate or substantially reduce the potential dead space volume, thus functionally negating the potential for a reaction between an air bubble and one or more active ingredient(s) introduced into the base of the primary capsule.

The primary, secondary or tertiary capsules, in accordance with the present invention, may be formed having the same or different colors. Moreover, the base and corresponding cap of a single capsule may be formed having different colors in an effort to enhance the aesthetics of the capsule to the consumer. In one presently preferred embodiment of a multi-compartment capsule of the present invention, the dosage may be banded, sealed or easily dividable in a contact area of the primary and secondary capsules or the sealing band may be color-coded to assist in branding, if desired.

It is further contemplated herein that a multi-compartment capsule of the present invention may comprise component parts of the capsule having various time-release coatings to facilitate the release and ultimately the absorption of those active ingredients introduced into the different receiving chambers of the multi-compartment capsule to release at different release rates. In particular, a primary capsule may be formed having a conventional time-release coating that dissolves and releases the active ingredient(s) contained therein before the timed-release of the active ingredient(s) contained within a secondary capsule. Likewise, the dividing walls disposed within the internal periphery of the base of a capsule may be formed having conventional time-release coatings that dissolve and release the active ingredients within each receiving chamber defined by the dividing walls at different rates, thereby delivering the active ingredients or medicaments contained within a multi-compartment capsule at different rates. Certain active ingredients or medicaments may, therefore, be delivered at a selected interval, while other ingredients may be released at a later interval. In this way, the novel design of the multi-compartment capsules of the present invention may facilitate precision delivery of active ingredients to targeted areas of the consumer.

Still further, a primary object of the present invention is to provide novel delivery apparatus and methods for affecting multiple organ systems in animals or humans using a plurality of medicaments delivered by a pharmaceutical formulation comprising a multi-chambered apparatus. Accordingly, the present invention provides novel delivery apparatus and administration techniques or methods aimed at affecting multiple organ systems in an animal or human using a plurality of medicaments. A delivery apparatus may be in any multi-chambered apparatus, but preferably in a capsular formulation. Thus, a plurality of medicaments may be encapsulated and stored separately within a larger capsule until the time of ingestion, consumption, or the like. Upon consumption, the capsule walls of one or more dividing walls of a capsule may dissolve to release their contents. Different methods of encapsulation may be used to deliver their respective contents, including but not limited to, dissolution, melting, ablation or biodegradation of the encapsulating wall. In certain embodiments and as contemplated herein, the medicaments retained in the multicompartment capsule may actually diffuse through one or more of the encapsulating walls.

In one embodiment of the present invention there is a multi-compartment capsule, comprising a first receiving chamber comprising at least one ingredient having a first physical state, wherein said ingredient is selected from the group consisting of a nutraceutical, a vitamin, a dietary supplement and a mineral; and a second receiving chamber comprising at least one ingredient having a second physical state, wherein said ingredient is selected from the group consisting of a nutraceutical, a vitamin, a dietary supplement and a mineral; said first physical state of said ingredient of said first receiving chamber being different from said second physical state of said ingredient of said second receiving chamber.

In another embodiment of the present invention, there is a multi-compartment capsule as defined above, further comprising a base and a corresponding cap, wherein said cap is configured to provide a sealing relationship when engaging said base.

In another embodiment of the present invention, there is a multi-compartment capsule as defined above, wherein said cap comprises a configuration adapted to reduce dead volume space within said first receiving chamber.

In another embodiment of the present invention, there is a multi-compartment capsule as defined above, further comprising a filling material introduced into said cap to reduce dead volume space within said first receiving chamber.

In another embodiment of the present invention, there is a multi-compartment capsule as defined above, wherein said filling material is selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, oleoresin, polyvinylacetate-phtalate, polymerisates of acrylic or methacrylic esters and combinations thereof.

In another embodiment of the present invention, there is a multi-compartment capsule as defined above, wherein said first receiving chamber comprises no dead volume space.

In another embodiment of the present invention, there is a multi-compartment capsule as defined above, wherein said physical state of said ingredient in said first receiving chamber is selected from the group consisting of a solid, a liquid, a gas and a dispersion.

In another embodiment of the present invention, there is a multi-compartment capsule as defined above, wherein said physical state of said ingredient in said second receiving chamber is selected from the group consisting of a solid, a liquid, a gas and a dispersion.

In another embodiment of the present invention, there is a multi-compartment capsule as defined above, wherein said solid is selected from the group consisting of a pill, a tablet, a capsule, a powder, granulation, flakes, a troche, a suppository, an ointment, a paste, an emulsion and a cream.

In another embodiment of the present invention, there is a multi-compartment capsule as defined above, wherein said liquid is selected from the group consisting of a solution, a spirit, an elixir, a spray, a syrup and a fluid extract.

In another embodiment of the present invention, there is a multi-compartment capsule as defined above, wherein said dispersion is selected from the group consisting of an aerosol, a suspension, an emulsion, a foam, a solid foam and a gel.

In another embodiment of the present invention, there is a multi-compartment capsule as defined above, wherein said first receiving chamber comprises a time-release coating.

In another embodiment of the present invention, there is a multi-compartment capsule as defined above, wherein said second receiving chamber comprises a time-release coating.

In another embodiment of the present invention, there is a multi-compartment capsule as defined above, wherein said time-release coating of said second receiving chamber is different from said time-release coating of said primary capsule.

In another embodiment of the present invention, there is a multi-compartment capsule as defined above, further comprising a third receiving chamber comprising at least one ingredient.

In another embodiment of the present invention, there is a multi-compartment capsule as defined above, wherein said ingredient in said third receiving chamber is selected from the group consisting of a nutraceutical, a vitamin, a dietary supplement and a mineral.

In another embodiment of the present invention, there is a multi-compartment capsule as defined above, wherein said ingredient in said third receiving chamber comprises a physical state selected from the group consisting of a solid, a liquid, a gas and a dispersion.

In another embodiment of the present invention, there is a multi-compartment capsule as defined above, wherein said third receiving chamber comprises a time-release coating.

In another embodiment of the present invention, there is a multi-compartment capsule, comprising a primary capsule comprising at least one ingredient having a first physical state, wherein said ingredient is selected from the group consisting of a nutraceutical, a vitamin, a dietary supplement and a mineral; a secondary capsule comprising at least one ingredient having a second physical state, wherein said ingredient is selected from the group consisting of a nutraceutical, a vitamin, a dietary supplement and a mineral; said first physical state of said ingredient of said primary capsule being different from said second physical state of said ingredient of said secondary capsule; and said primary capsule comprising an internal periphery sufficient for receiving said ingredient and said secondary capsule therein.

In another embodiment of the present invention, there is a multi-compartment capsule as defined above, wherein said primary capsule further comprises a base and a corresponding cap, wherein said cap is configured to provide a sealing relationship when engaging said base.

In another embodiment of the present invention, there is a multi-compartment capsule as defined above, wherein said primary capsule comprises no dead volume space.

In another embodiment of the present invention, there is a multi-compartment capsule as defined above, wherein said first physical state of said ingredient in said primary capsule is selected from the group consisting of a solid, a liquid, a gas and a dispersion.

In another embodiment of the present invention, there is a multi-compartment capsule as defined above, wherein said second physical state of said ingredient in said secondary capsule is selected from the group consisting of a solid, a liquid, a gas and a dispersion.

In another embodiment of the present invention, there is a multi-compartment capsule as defined above, wherein said primary capsule comprises a time-release coating.

In another embodiment of the present invention, there is a multi-compartment capsule as defined above, wherein said secondary capsule comprises a time-release coating.

In another embodiment of the present invention, there is a multi-compartment capsule as defined above, wherein said time-release coating of said secondary capsule is different from said time-release coating of said primary capsule.

In another embodiment of the present invention, there is a multi-compartment capsule as defined above, wherein said third receiving chamber comprises a time-release coating.

In another embodiment of the present invention, there is a multi-compartment capsule as defined above, wherein said primary capsule is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, oleoresin, polyvinylacetate, hydroxypropyl methyl cellulose, polymerisates of acrylic or methacrylic esters, polyvinylacetate-phtalate and combinations thereof.

In another embodiment of the present invention, there is a multi-compartment capsule as defined above, wherein said primary capsule further comprises a soft elastic capsule formed of a material selected from the group consisting of glycerin and sorbitol.

In another embodiment of the present invention, there is an encapsulation process as defined above, wherein said soft elastic capsule includes an antimicrobial selected from the group consisting of paraben and sorbic acid.

In another embodiment of the present invention, there is a multi-compartment capsule as defined above, wherein said secondary capsule is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, oleoresin, polyvinylacetate, hydroxypropyl methyl cellulose, polymerisates of acrylic or methacrylic esters, polyvinylacetate-phtalate and combinations thereof.

In another embodiment of the present invention, there is a multi-compartment capsule as defined above, wherein said ingredient introduced in said primary capsule comprises a moisture content in the range of about 0% to 6% by weight.

In another embodiment of the present invention, there is a multi-compartment capsule as defined above, wherein said ingredient introduced in said secondary capsule comprises a moisture content in the range of about 0% to 6% by weight.

In another embodiment of the present invention, there is a multi-compartment capsule as defined above, wherein said primary and secondary capsules contain at least one pharmaceutically acceptable lubricant in the range of about 0% to 10% by weight.

In another embodiment of the present invention, there is a multi-compartment capsule as defined above, wherein said lubricant is selected from the group consisting of aluminiumstearate, calciumstearate, magnesiumstearate, tinstearate, talc, sodium lauryl sulfate, lecithins, mineral oils, stearic acid, silicones and mixtures thereof.

In another embodiment of the present invention, there is a multi-compartment capsule as defined above, wherein said primary and secondary capsules have different colors.

In another embodiment of the present invention, there is a multi-compartment capsule as defined above, wherein said primary capsule is formed having a first color.

In another embodiment of the present invention, there is a multi-compartment capsule as defined above, wherein said secondary capsule is formed having a second color different from said first color of said primary capsule.

In another embodiment of the present invention, there is a multi-compartment capsule as defined above, wherein said capsule further comprises a base and a corresponding cap, wherein said cap is configured to provide a sealing relationship when engaging said base.

In another embodiment of the present invention, there is a multi-compartment capsule as defined above, wherein said base and said cap are formed having different colors.

In another embodiment of the present invention, there is a multi-compartment capsule as defined above, wherein said sealing relationship between said base and corresponding cap comprises no dead volume space.

In another embodiment of the present invention, there is a multi-compartment capsule as defined above, wherein said physical state of said ingredient in said first receiving chamber is selected from the group consisting of a solid, a liquid, a gas and a dispersion.

In another embodiment of the present invention, there is a multi-compartment capsule as defined above, wherein said physical state of said ingredient in said second receiving chamber capsule is selected from the group consisting of a solid, a liquid, a gas and a dispersion.

In another embodiment of the present invention, there is a multi-compartment capsule as defined above, wherein said capsule comprises a time-release coating.

In another embodiment of the present invention, there is a multi-compartment capsule as defined above, wherein said dividing wall comprises a time-release coating.

In another embodiment of the present invention, there is a multi-compartment capsule as defined above, wherein said time-release coating of said dividing wall is different from said time-release coating of said capsule.

In another embodiment of the present invention, there is a multi-compartment capsule as defined above, wherein said third receiving chamber comprises a time-release coating.

In another embodiment of the present invention, there is a multi-compartment capsule as defined above, wherein said capsule is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, oleoresin, polyvinylacetate, hydroxypropyl methyl cellulose, polymerisates of acrylic or methacrylic esters, polyvinylacetate-phtalate and combinations thereof.

In another embodiment of the present invention, there is a multi-compartment capsule as defined above, wherein said capsule further comprises a soft elastic capsule formed of a material selected from the group consisting of glycerin and sorbitol.

In another embodiment of the present invention, there is a multi-compartment capsule as defined above, wherein said dividing wall is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, oleoresin, polyvinylacetate, hydroxypropyl methyl cellulose, polymerisates of acrylic or methacrylic esters, polyvinylacetate-phtalate and combinations thereof.

In another embodiment of the present invention, there is a multi-compartment capsule as defined above, wherein said ingredient introduced in said first receiving chamber comprises a moisture content in the range of about 0% to 6% by weight.

In another embodiment of the present invention, there is a multi-compartment capsule as defined above, wherein said ingredient introduced in said second receiving chamber comprises a moisture content in the range of about 0% to 6% by weight.

In another embodiment of the present invention, there is a multi-compartment capsule as defined above, wherein said capsule contains at least one pharmaceutically acceptable lubricant in the range of about 0% to 10% by weight.

In another embodiment of the present invention there is, an encapsulation process for forming a multi-compartment capsule, said process comprising the steps of providing a primary capsule having a base and a cap; providing a secondary capsule having a base and a cap; introducing at least one ingredient having a first physical state into said secondary capsule, wherein said ingredient introduced into said primary capsule is selected from the group consisting of a nutraceutical, a vitamin, a dietary supplement and a mineral; positioning said cap of said secondary capsule in sealing relationship with said base; introducing at least one ingredient having a second physical state into said primary capsule, wherein said ingredient introduced into said primary capsule is selected from the group consisting of a nutraceutical, a vitamin, a dietary supplement and a mineral; and wherein said first physical state of said ingredient of said secondary capsule is different from said second physical state of said ingredient of said primary capsule; introducing said secondary capsule into said base of said primary capsule; and positioning said cap of said primary capsule in sealing relationship with said base.

In another embodiment of the present invention there is, an encapsulation process as defined above, further comprising the step of reducing dead volume space within said primary capsule.

In another embodiment of the present invention, an encapsulation process as defined above, further comprising the step of introducing a filling material into said cap of said primary capsule to reduce dead volume space.

In another embodiment of the present invention, there is an encapsulation process as defined above, wherein said filling material is selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, oleoresin, polyvinylacetate-phtalate, polymerisates of acrylic or methacrylic esters and combinations thereof.

In another embodiment of the present invention, an encapsulation process as defined above, wherein said cap of said primary capsule comprises a configuration sufficient for reducing dead volume space within the primary capsule.

In another embodiment of the present invention, there is an encapsulation process as defined above, wherein said physical state of said ingredient in said primary capsule is selected from the group consisting of a solid, a liquid, a gas and a dispersion.

In another embodiment of the present invention, there is an encapsulation process as defined above, wherein said physical state of said ingredient in said secondary capsule is selected from the group consisting of a solid, a liquid, a gas and a dispersion.

In another embodiment of the present invention, there is an encapsulation process as defined above, wherein said ingredient introduced into said primary capsule is the same as said ingredient introduced into said secondary capsule.

In another embodiment of the present invention, there is an encapsulation process as defined above, wherein said primary capsule comprises a time-release coating.

In another embodiment of the present invention, there is an encapsulation process as defined above, wherein said secondary capsule comprises a time-release coating.

In another embodiment of the present invention, there is an encapsulation process as defined above, wherein said time-release coating of said secondary capsule is different from said time-release coating of said primary capsule.

In another embodiment of the present invention, there is an encapsulation process as defined above, further comprising the steps of providing a tertiary capsule having a base and a cap; introducing at least one ingredient having a third physical state into said tertiary capsule; positioning said cap of said secondary capsule in sealing relationship with said base; and introducing said tertiary capsule into said base of said secondary capsule.

In another embodiment of the present invention, there is an encapsulation process as defined above, wherein said ingredient in said tertiary capsule is selected from the group consisting of a nutraceutical, a vitamin, a dietary supplement and a mineral.

In another embodiment of the present invention, there is an encapsulation process as defined above, wherein said ingredient in said tertiary capsule comprises a physical state selected from the group consisting of a solid, a liquid, a gas and a dispersion.

In another embodiment of the present invention, there is an encapsulation process as defined above, wherein said tertiary capsule comprises a time-release coating.

In another embodiment of the present invention, there is an encapsulation process as defined above, wherein said primary capsule is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, oleoresin, polymerisates of acrylic or mthacrylic esters, polyvinylacetate-phtalate and combinations thereof.

In another embodiment of the present invention, there is an encapsulation process as defined above, wherein said primary capsule further comprises a soft elastic capsule formed of a material selected from the group consisting of glycerin and sorbitol.

In another embodiment of the present invention, there is an encapsulation process as defined above, wherein said secondary capsule is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, oleoresin, polymerisates of acrylic or mthacrylic esters, polyvinylacetate-phtalate and combinations thereof.

In another embodiment of the present invention, there is an encapsulation process as defined above, wherein said secondary capsule further comprises a soft elastic capsule formed of a material selected from the group consisting of glycerin and sorbitol.

In another embodiment of the present invention, there is an encapsulation process as defined above, wherein said ingredient introduced in said primary capsule comprises a moisture content in the range of about 0% to 6% by weight.

In another embodiment of the present invention, there is a multi-compartment capsule as defined above, wherein said ingredient introduced in said secondary capsule comprises a moisture content in the range of about 0% to 6% by weight.

In another embodiment of the present invention, there is an encapsulation process as defined above, wherein said primary and secondary capsules contain at least one pharmaceutically acceptable lubricant in the range of about 0% to 10% by weight.

In another embodiment of the present invention, there is an encapsulation process as defined above, wherein said lubricant is selected from the group consisting of aluminiumstearate, calciumstearate, magnesiumstearate, tinstearate, talc, sodium lauryl sulfate, lecithins, mineral oils, stearic acid, silicones and combinations thereof.

In another embodiment of the present invention, there is an encapsulation process as defined above, wherein said primary and secondary capsules are formed having different colors.

In another embodiment of the present invention, there is an encapsulation process for forming a multi-compartment capsule, said process comprising the steps of providing a capsule comprising a cap, a base configured having a longitudinally extending body including a length and at least one dividing wall formed along said length of said extending body, said dividing wall adapted to form a first receiving chamber and a second receiving chamber; introducing at least one ingredient having a first physical state into said second receiving chamber, wherein said ingredient introduced into said primary capsule is selected from the group consisting of a nutraceutical, a vitamin, a dietary supplement and a mineral; introducing at least one ingredient having a second physical state into said first receiving chamber, wherein said ingredient introduced into said primary capsule is selected from the group consisting of a nutraceutical, a vitamin, a dietary supplement and a mineral, and wherein said first physical state of said ingredient of said second receiving chamber being different from said second physical state of said ingredient of said first receiving chamber; and positioning said cap in sealing relationship with said base.

In another embodiment of the present invention, there is an encapsulation process as defined above, further comprising the step of reducing dead volume space within said primary capsule.

In another embodiment of the present invention, there is an encapsulation process as defined above, further comprising the step of introducing a filling material into said cap to reduce said dead volume space.

In another embodiment of the present invention, there is an encapsulation process as defined above, wherein said filling material is selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, oleoresin, polyvinylacetate-phtalate, polymerisates of acrylic or methacrylic esters and combinations thereof.

In another embodiment of the present invention, there is an encapsulation process as defined above, wherein said cap comprises a configuration sufficient for reducing dead volume space within said capsule.

In another embodiment of the present invention, there is an encapsulation process as defined above, wherein said physical state of said ingredient in said receiving chamber is selected from the group consisting of a solid, a liquid, a gas and a dispersion.

In another embodiment of the present invention, there is an encapsulation process as defined above, wherein said physical state of said ingredient in said second receiving chamber is selected from the group consisting of a solid, a liquid, a gas and a dispersion.

In another embodiment of the present invention, there is an encapsulation process as defined above, wherein said first receiving chamber comprises a time-release coating.

In another embodiment of the present invention, there is an encapsulation process as defined above, wherein said second receiving chamber comprises a time-release coating.

In another embodiment of the present invention, there is an encapsulation process as defined above, wherein said time-release coating of said second receiving chamber is different from said time-release coating of said first receiving chamber.

In another embodiment of the present invention, there is an encapsulation process as defined above, further comprising the steps of positioning a second dividing wall along said length of said extending body, said second dividing wall adapted to form a third receiving chamber; and introducing at least one ingredient having a third physical state into said third receiving chamber.

In another embodiment of the present invention, there is an encapsulation process as defined above, wherein said ingredient in said third receiving chamber is selected from the group consisting of a nutraceutical, a vitamin, a dietary supplement and a mineral.

In another embodiment of the present invention, there is an encapsulation process as defined above, wherein said ingredient in said third receiving chamber comprises a physical state selected from the group consisting of a solid, a liquid, a gas and a dispersion.

In another embodiment of the present invention, there is an encapsulation process as defined above, wherein said dispersion is selected from the group consisting of an aerosol, a suspension, an emulsion, a foam, a solid foam and a gel.

In another embodiment of the present invention, there is an encapsulation process as defined above, wherein said third receiving chamber comprises a time-release coating.

In another embodiment of the present invention, there is an encapsulation process as defined above, wherein said capsule is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, oleoresin, polymerisates of acrylic or mthacrylic esters, polyvinylacetate-phtalate and combinations thereof.

In another embodiment of the present invention, there is an encapsulation process as defined above, wherein said capsule further comprises a soft elastic capsule formed of a material selected from the group consisting of glycerin and sorbitol.

In another embodiment of the present invention, there is an encapsulation process as defined above, wherein said primary and secondary capsules contain at least one pharmaceutically acceptable lubricant in the range of about 0% to 10% by weight.

In another embodiment of the present invention, there is an encapsulation process as defined above, wherein said lubricant is selected from the group consisting of aluminiumstearate, calciumstearate, magnesiumstearate, tinstearate, talc, sodium lauryl sulfate, lecithins, mineral oils, stearic acid, silicones and combinations thereof.

In another embodiment of the present invention, there is an encapsulation process as defined above, wherein said base and said cap of said capsule are formed having different colors.

In another embodiment of the present invention, there is an encapsulation process as defined above, further comprising the step of introducing two or more dividing walls adapted to form a plurality of receiving chambers into said base of said capsule.

In another embodiment of the present invention, there is an encapsulation process as defined above, further comprising the step of introducing a capsule into one of said plurality of receiving chambers.

In another embodiment of the present invention, there is an encapsulation process as defined above, wherein said capsule may comprise a multi-compartment capsule.

In another embodiment of the present invention, there is a multi-compartment capsule, comprising a first receiving chamber comprising at least one ingredient having a first physical state; and a second receiving chamber comprising at least one ingredient having a second physical state, wherein said first physical state of said ingredient of said first receiving chamber being different from said second physical state of said ingredient of said second receiving chamber.

In another embodiment of the present invention, there is a multi-compartment capsule as defined above, wherein said first receiving chamber comprises no dead space.

In another embodiment of the present invention, there is a multi-compartment capsule as defined above, wherein said cap is configured to reduce dead volume space within said first receiving chamber.

In another embodiment of the present invention, there is a multi-compartment capsule as defined above, further comprising a filling material introduced into said cap to reduce dead volume space within said first receiving chamber.

In another embodiment of the present invention, there is a multi-compartment capsule as defined above, wherein said ingredient in said first receiving chamber is selected from the group consisting of a pharmaceutical, a biotechnical, a nutraceutical, a vitamin, a dietary supplement and a mineral.

In another embodiment of the present invention, there is a multi-compartment capsule as defined above, wherein said ingredient in said second receiving chamber is selected from the group consisting of a pharmaceutical, a biotechnical, a nutraceutical, a vitamin, a dietary supplement and a mineral.

In another embodiment of the present invention, there is a multi-compartment capsule as defined above, wherein said ingredient in said first receiving chamber comprises a pharmaceutical and said ingredient in said second receiving chamber comprises a pharmaceutical.

In another embodiment of the present invention, there is a multi-compartment capsule as defined above, wherein said ingredient in said first receiving chamber comprises a pharmaceutical and said ingredient in said second receiving chamber is selected from the group consisting of a biotechnical, a nutraceutical, a vitamin, a dietary supplement and a mineral.

In another embodiment of the present invention, there is a multi-compartment capsule as defined above, wherein said physical state of said ingredient in said first receiving chamber is selected from the group consisting of a solid, a liquid, a gas and a dispersion.

In another embodiment of the present invention, there is a multi-compartment capsule as defined above, wherein said physical state of said ingredient in said second receiving chamber is selected from the group consisting of a solid, a liquid, a gas and a dispersion.

In another embodiment of the present invention, there is a multi-compartment capsule as defined above, wherein said time-release coating of said second receiving chamber is different from said time-release coating of said primary capsule.

In another embodiment of the present invention, there is a multi-compartment capsule, comprising a primary capsule comprising at least one ingredient having a first physical state; a secondary capsule comprising at least one ingredient having a second physical state; said first physical state of said ingredient of said primary capsule being different from said second physical state of said ingredient of said secondary capsule; and said primary capsule comprising an internal periphery sufficient for receiving said ingredient and said secondary capsule therein.

In another embodiment of the present invention, there is a multi-compartment capsule as defined above, wherein said primary capsule further comprises a base and a corresponding cap, wherein said cap is configured to provide a sealing relationship when engaging said base.

In another embodiment of the present invention, there is a multi-compartment capsule as defined above, wherein said primary capsule comprises no dead volume space.

In another embodiment of the present invention, there is a multi-compartment capsule as defined above, wherein said ingredient in said primary capsule is selected from the group consisting of a pharmaceutical, a biotechnical, a nutraceutical, a vitamin, a dietary supplement and a mineral.

In another embodiment of the present invention, there is a multi-compartment capsule as defined above, wherein said ingredient in said secondary capsule is selected from the group consisting of a pharmaceutical, a biotechnical, a nutraceutical, a vitamin, a dietary supplement and a mineral.

In another embodiment of the present invention, there is a multi-compartment capsule as defined above, wherein said ingredient in said first receiving chamber comprises a pharmaceutical and said ingredient in said second receiving chamber comprises a pharmaceutical.

In another embodiment of the present invention, there is a multi-compartment capsule as defined above, wherein said ingredient introduced in said primary capsule comprises a moisture content in the range of about 0% to 6% by weight.

In another embodiment of the present invention, there is a multi-compartment capsule as defined above, wherein said ingredient introduced in said secondary capsule comprises a moisture content in the range of about 0% to 6% by weight.

In another embodiment of the present invention, there is a multi-compartment capsule as defined above, wherein said primary and secondary capsules contain at least one pharmaceutically acceptable lubricant in the range of about 0% to 10% by weight.

In another embodiment of the present invention, there is a multi-compartment capsule as defined above, wherein said lubricant is selected from the group consisting of aluminiumstearate, calciumstearate, magnesiumstearate, tinstearate, talc, sodium lauryl sulfate, lecithins, mineral oils, stearic acid, silicones and mixtures thereof.

In another embodiment of the present invention, there is a multi-compartment capsule as defined above, wherein said primary and secondary capsules have different colors.

In another embodiment of the present invention, there is a multi-compartment capsule as defined above, wherein said primary capsule is formed having a first color.

In another embodiment of the present invention, there is a multi-compartment capsule as defined above, wherein said secondary capsule is formed having a second color different from said first color of said primary capsule.

In another embodiment of the present invention, there is a multi-compartment capsule, comprising a capsule comprising a longitudinally extending body having a length; at least one dividing wall formed along said length of said extending body, said dividing wall forming a first receiving chamber and a second receiving chamber; said first receiving chamber comprising at least one ingredient having a first physical state; said second receiving chamber comprising at least one ingredient having a second physical state; and said first physical state of said ingredient of said first receiving chamber being different from said second physical state of said ingredient of said second receiving chamber.

In another embodiment of the present invention, there is a multi-compartment capsule as defined above, wherein said capsule further comprises a base and a corresponding cap, wherein said cap is configured to provide a sealing relationship when engaging said base.

In another embodiment of the present invention, there is a multi-compartment capsule as defined above, wherein said base and said cap are formed having different colors.

In another embodiment of the present invention, there is a multi-compartment capsule as defined above, wherein said sealing relationship between said base and corresponding cap comprises no dead volume space within said capsule.

In another embodiment of the present invention, there is a multi-compartment capsule as defined above, wherein said ingredient in said first receiving chamber comprises a pharmaceutical and said ingredient in said second receiving chamber comprises a pharmaceutical.

In another embodiment of the present invention, there is a multi-compartment capsule as defined above, wherein said ingredient in said first receiving chamber comprises a pharmaceutical and said ingredient in said second receiving chamber is selected from the group consisting of a biotechnical, a nutraceutical, a vitamin, a dietary supplement and a mineral.

In another embodiment of the present invention, there is a multi-compartment capsule as defined above, wherein said first physical state of said ingredient in said first receiving chamber is selected from the group consisting of a solid, a liquid, a gas and a dispersion.

In another embodiment of the present invention, there is a multi-compartment capsule as defined above, wherein said second physical state of said ingredient in said second receiving chamber capsule is selected from the group consisting of a solid, a liquid, a gas and a dispersion.

In another embodiment of the present invention, there is a multi-compartment capsule as defined above, wherein said capsule comprises a time-release coating.

In another embodiment of the present invention, there is a multi-compartment capsule as defined in above, wherein said capsule is formed of a material selected from the group consisting of gelatin, starch, casein, chitosan, soya bean protein, safflower protein, alginates, gellan gum, carrageenan, xanthan gum, phtalated gelatin, succinated gelatin, celluloseph-talate-acetate, polyvinylacetate, hydroxypropyl methyl cellulose, oleoresin, polymerisates of acrylic or methacrylic esters, polyvinylacetate-phtalate and mixtures thereof.

In another embodiment of the present invention, there is a multi-compartment capsule as defined above, wherein said capsule further comprises a soft elastic capsule formed of a material selected from the group consisting of glycerin and sorbitol.

In another embodiment of the present invention, there is a multi-compartment capsule as defined above, wherein said lubricant is selected from the group consisting of aluminiumstearate, calciumstearate, magnesiumstearate, tinstearate, talc, sodium lauryl sulfate, lecithins, mineral oils, stearic acid, silicones and mixtures thereof.

In another embodiment of the present invention, there is an encapsulation process for forming a multi-compartment capsule, said process comprising the steps of providing a primary capsule having a base and a cap; providing a secondary capsule having a base and a cap; introducing at least one ingredient having a first physical state into said secondary capsule; positioning said cap of said secondary capsule in sealing relationship with said base; introducing at least one ingredient having a second physical state into said primary capsule, wherein said first physical state of said ingredient of said secondary capsule is different from said second physical state of said ingredient of said primary capsule; introducing said secondary capsule into said base of said primary capsule; and positioning said cap of said primary capsule in sealing relationship with said base.

In another embodiment of the present invention, there is an encapsulation process as defined above, further comprising the step of reducing dead volume space within said primary capsule.

In another embodiment of the present invention, there is an encapsulation process as defined above, further comprising the step of introducing a filling material into said cap of said primary capsule to reduce dead volume space.

In another embodiment of the present invention, there is an encapsulation process as defined above, wherein said cap of said primary capsule comprises a configuration sufficient for reducing dead volume space within the primary capsule.

In another embodiment of the present invention, there is an encapsulation process as defined above, wherein said ingredient introduced into said primary capsule is selected from the group consisting of a pharmaceutical, a biotechnical, a nutraceutical, a vitamin, a dietary supplement and a mineral.

In another embodiment of the present invention, there is an encapsulation process as defined above, wherein said physical state of said ingredient in said primary capsule is selected from the group consisting of a solid, a liquid, a gas and a dispersion.

In another embodiment of the present invention, there is an encapsulation process as defined above, wherein said ingredient in said secondary capsule is selected from the group consisting of a pharmaceutical, a biotechnical, a nutraceutical, a vitamin, a dietary supplement and a mineral.

In another embodiment of the present invention, there is an encapsulation process as defined above, wherein said physical state of said ingredient in said secondary capsule is selected from the group consisting of a solid, a liquid, a gas and a dispersion.

In another embodiment of the present invention, there is an encapsulation process as defined above, wherein said ingredient in said primary capsule comprises a pharmaceutical and said ingredient in said secondary capsule is selected from the group consisting of a pharmaceutical.

In another embodiment of the present invention, there is an encapsulation process as defined above, wherein said ingredient in said primary capsule comprises a pharmaceutical and said ingredient in said secondary capsule is selected from the group consisting of a biotechnical, a nutraceutical, a vitamin, a dietary supplement and a mineral.

In another embodiment of the present invention, there is an encapsulation process as defined above, wherein said ingredient introduced into said primary capsule is the same as said ingredient introduced into said secondary capsule.

In another embodiment of the present invention, there is an encapsulation process as defined above, wherein said time-release coating of said secondary capsule is different from said time-release coating of said primary capsule.

In another embodiment of the present invention, there is an encapsulation process as defined above, further comprising the steps of providing a tertiary capsule having a base and a cap; introducing at least one ingredient having a third physical state into said tertiary capsule; positioning said cap of said secondary capsule in sealing relationship with said base; and introducing said tertiary capsule into said base of said secondary capsule.

In another embodiment of the present invention, there is an encapsulation process as defined above, wherein said ingredient in said tertiary capsule is selected from the group consisting of a pharmaceutical, a biotechnical, a nutraceutical, a vitamin, a dietary supplement and a mineral.

In another embodiment of the present invention, there is an encapsulation process as defined above, wherein said ingredient in said tertiary capsule comprises a physical state selected from the group consisting of a solid, a liquid, a gas and a dispersion.

In another embodiment of the present invention, there is an encapsulation process as defined above, wherein said tertiary capsule comprises a time-release coating.

In another embodiment of the present invention, there is an encapsulation process as defined above, wherein said lubricant is selected from the group consisting of aluminiumstearate, calciumstearate, magnesiumstearate, tinstearate, talc, sodium lauryl sulfate, lecithins, mineral oils, stearic acid, silicones and combinations thereof.

In another embodiment of the present invention, there is an encapsulation process as defined above, wherein said primary and secondary capsules are formed having different colors.

In another embodiment of the present invention, there is an encapsulation process for forming a multi-compartment capsule, said process comprising the steps of providing a capsule comprising a cap, a base configured having a longitudinally extending body including a length and at least one dividing wall formed along said length of said extending body, said dividing wall adapted to form a first receiving chamber and a second receiving chamber; introducing at least one ingredient having a first physical state into said second receiving chamber; introducing at least one ingredient having a second physical state into said first receiving chamber, wherein said first physical state of said ingredient of said second receiving chamber being different from said second physical state of said ingredient of said first receiving chamber; and positioning said cap in sealing relationship with said base.

In another embodiment of the present invention, there is an encapsulation process as defined above, further comprising the step of reducing dead volume space within said primary capsule.

In another embodiment of the present invention, there is an encapsulation process as defined above, wherein said filling material is selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, polyvinylacetate-phtalate, polymerisates of acrylic or methacrylic esters and combinations thereof.

In another embodiment of the present invention, there is an encapsulation process as defined above, wherein said cap comprises a configuration sufficient for reducing dead volume space within said capsule.

In another embodiment of the present invention, there is an encapsulation process as defined above, wherein said ingredient in said first receiving chamber is selected from the group consisting of a pharmaceutical, a biotechnical, a nutraceutical, a vitamin, a dietary supplement and a mineral.

In another embodiment of the present invention, there is an encapsulation process as defined above, wherein said physical state of said ingredient in said receiving chamber is selected from the group consisting of a solid, a liquid, a gas and a dispersion.

In another embodiment of the present invention, there is an encapsulation process as defined above, wherein said ingredient in said second receiving chamber is selected from the group consisting of a pharmaceutical, a biotechnical, a nutraceutical, a vitamin, a dietary supplement and a mineral.

In another embodiment of the present invention, there is an encapsulation process as defined above, wherein said physical state of said ingredient in said second receiving chamber is selected from the group consisting of a solid, a liquid, a gas and a dispersion.

In another embodiment of the present invention, there is an encapsulation process as defined above, wherein said ingredient in said first receiving chamber comprises a pharmaceutical and said ingredient in said second receiving chamber is selected from the group consisting of a pharmaceutical.

In another embodiment of the present invention, there is an encapsulation process as defined above, wherein said time-release coating of said second receiving chamber is different from said time-release coating of said first receiving chamber.

In another embodiment of the present invention, there is an encapsulation process as defined above, further comprising the steps of positioning a second dividing wall along said length of said extending body of said base, said second dividing wall adapted to form a third receiving chamber; and introducing at least one ingredient having a physical state into said third receiving chamber.

In another embodiment of the present invention, there is an encapsulation process as defined above, wherein said ingredient introduced into said third receiving chamber is selected from the group consisting of a pharmaceutical, a biotechnical, a nutraceutical, a vitamin, a dietary supplement and a mineral.

In another embodiment of the present invention, there is an encapsulation process as defined above, wherein said physical state of said ingredient introduced into said third receiving chamber is selected from the group consisting of a solid, a liquid, a gas and a dispersion.

In another embodiment of the present invention, there is an encapsulation process as defined above, wherein said second dividing wall comprises a time-release coating.

In another embodiment of the present invention, there is an encapsulation process as defined above, wherein said capsule further comprises a soft elastic capsule formed of a material selected from the group consisting of glycerin and sorbitol.

In another embodiment of the present invention, there is an encapsulation process as defined above, wherein said lubricant is selected from the group consisting of aluminiumstearate, calciumstearate, magnesiumstearate, tinstearate, talc, sodium lauryl sulfate, lecithins, mineral oils, stearic acid, silicones and combinations thereof.

In another embodiment of the present invention, there is an encapsulation process as defined above, wherein said base and said cap of said capsule are formed having different colors.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations and process steps. Those of ordinary skill in the art will, of course, appreciate that various modifications to the details herein may easily be made without departing from the essential characteristics of the invention, as described. Thus, the following more detailed description of the embodiments of apparatus and methods of the present invention, as represented in FIGS. 1 through 13, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 1:
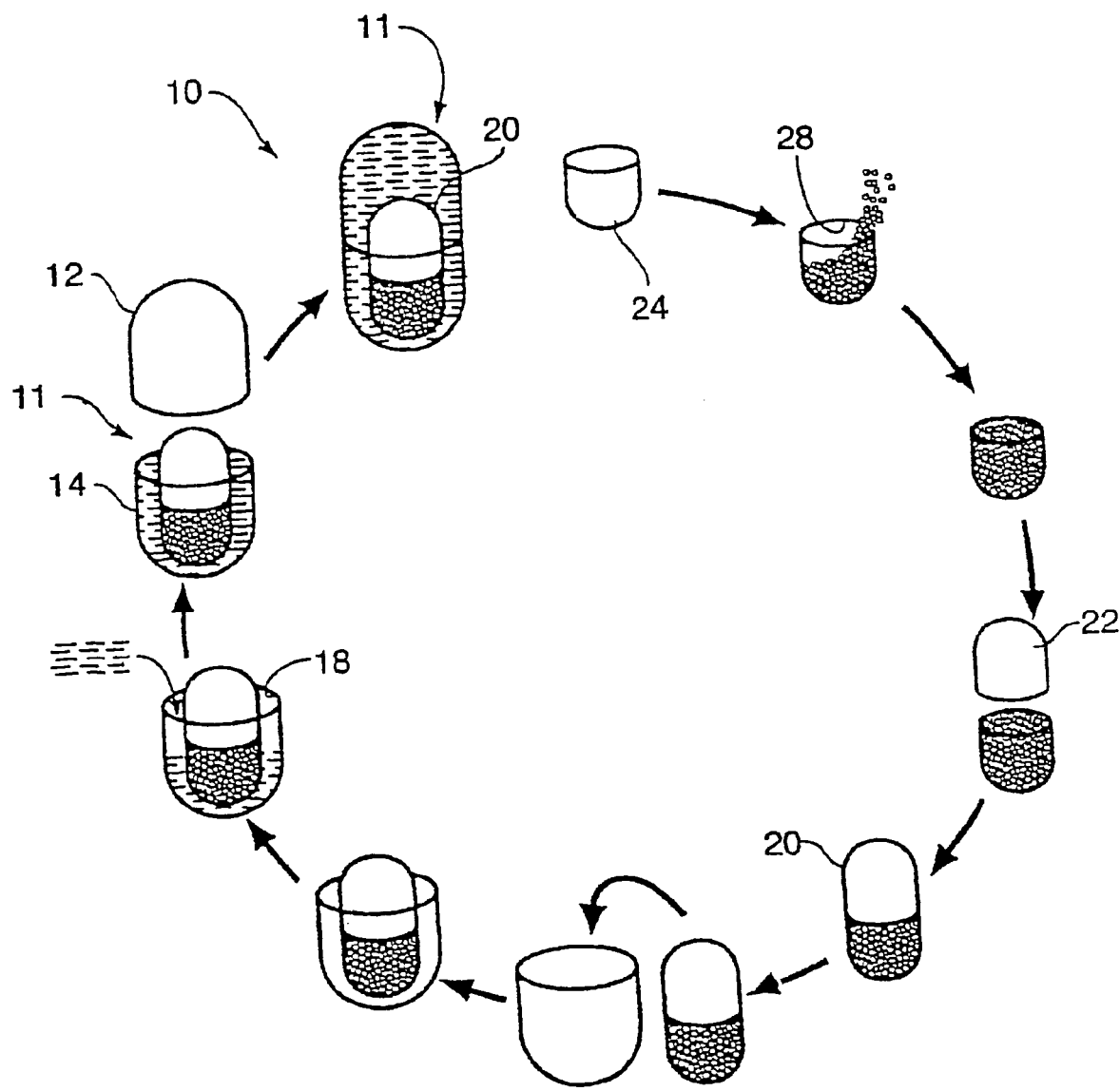
FIG. 1 is a flow diagram illustrating one presently preferred embodiment of a process of the present invention comprising the steps of introducing at least one active ingredient or medicament having a solid physical state into a secondary capsule and introducing the secondary capsule into a primary capsule further including at least one active ingredient or medicament having a liquid physical state.

One presently preferred embodiment of the present invention, designated generally at 10, is best illustrated in FIG. 1. As shown, a multi-compartment capsule 10 is illustrated comprising a primary capsule 11 and a secondary capsule 20 selectively introduced within at least a portion of an internal periphery of the primary capsule. The secondary capsule 20 includes a base 24, a corresponding cap 22 and a receiving chamber 28 formed between the base and cap. The receiving chamber 28 is configured having an internal periphery sufficient for receiving at least one active ingredient or medicament (e.g., pharmaeceutical, biotechnical, nutraceutical, vitamin, dietary supplement, mineral or combination thereof) therein. In similar structural design, the primary capsule 11 may be formed having a base 14, a corresponding cap 12 and a receiving chamber 18 formed between the base and cap. The receiving chamber 18 of the primary capsule 11 is preferably formed having an internal periphery sufficient for receiving the secondary capsule 20, together with at least one active ingredient or medicament (e.g., pharmaeceutical, biotechnical, nutraceutical, vitamin, dietary supplement, mineral or combination thereof) therein.

Still referring to FIG. 1, one presently preferred embodiment of an encapsulation process for forming a multi-compartment capsule 10 is comprising the steps of: (1) providing a primary capsule 11 having a base 14, a corresponding cap 12 and a receiving chamber 18; (2) providing a secondary capsule 20 having a base 24, a corresponding cap 22 and a receiving chamber 28; (3) introducing at least one ingredient or medicament (e.g., pharmaeceutical, biotechnical, nutraceutical, vitamin, dietary supplement, mineral or combination thereof) having a first physical state (e.g., solid, liquid, gas or dispersion) into at least a portion of the receiving chamber 28 of the secondary capsule 20 and selectively positioning the cap 22 in sealing relationship with the base 24; (4) introducing at least one ingredient or medicament (e.g., pharmaeceutical, biotechnical, nutraceutical, vitamin, dietary supplement, mineral or combination thereof) having a second physical state (e.g., solid, liquid, gas or dispersion) into at least a portion of the receiving chamber 18 of the primary capsule 11, wherein the first physical state of the ingredient(s) in the secondary capsule is different from the second physical state of the ingredient(s) in the primary capsule; and (5) introducing the secondary capsule 20 into at least a portion of the receiving chamber 18 of the primary capsule 11 and selectively positioning the cap 12 in sealing relationship with the base 14 to form a single dosage multi-compartment capsule.

As shown, a solid is selectively introduced within at least a portion of the internal periphery of the receiving chamber 28 of the secondary capsule 20 and a liquid is selectively introduced within at least a portion of the internal periphery of the receiving chamber 18 of the primary capsule 11. Although the ingredient(s) introduced into the receiving chamber 18 of the primary capsule 11 may be the same or different from the ingredient(s) introduced into the receiving chamber 28 of the secondary capsule, the active ingredient(s) in the primary capsule 11 have a physical state (i.e., solid, liquid, gas or dispersion) that varies from the physical state of the active ingredient(s) in the secondary capsule 20. Accordingly, those skilled in the art will readily recognize other possible modifications and adaptations relative to the contemplated variations in physical states of the active ingredient(s) selectively positionable within the receiving chambers 18, 28 of the primary and secondary capsules, respectively, which are consistent with the spirit and scope of the present invention. It is intended, therefore, that the figures and examples provided herein be viewed as exemplary of the principles of the present invention, and not as restrictive to a particular structure or method for implementing those principles.

Figure 2:
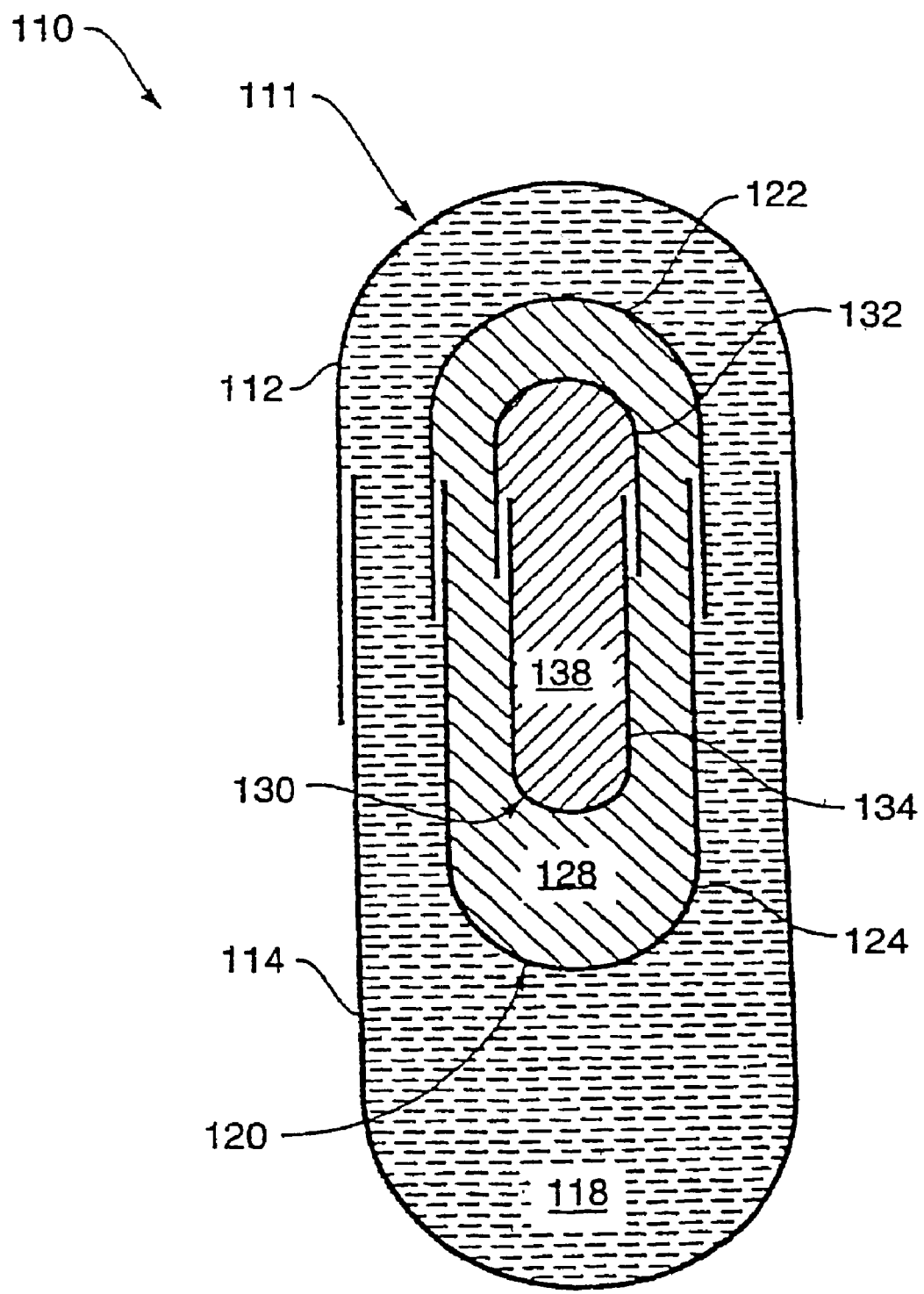
FIG. 2 is a cross-sectional view illustrating another presently preferred embodiment of a multi-compartment capsule of the present invention wherein a primary capsule houses a secondary capsule and a secondary capsule houses a tertiary capsule, wherein each of the capsules include one or more active ingredients or medicaments and the active ingredient(s) introduced into at least two of the capsules comprise different physical states.

Referring now to FIG. 2, an alternate presently preferred embodiment of a multi-compartment capsule 110 is shown comprising a primary capsule 111, a secondary capsule 120 and a tertiary capsule 130. The tertiary capsule 130 includes a base 134, a corresponding cap 132 and a receiving chamber 138 formed between the base and cap. The receiving chamber 138 is preferably formed having an internal periphery sufficient for receiving at least one active ingredient or medicament (e.g., pharmaeceutical, biotechnical, nutraceutical, vitamin, dietary supplement, mineral or combination thereof). Structurally, the tertiary capsule 130 is configured having a size sufficient for being selectively introduced within at least a portion of an internal periphery of a receiving chamber 128 defined between a base 124 and a corresponding cap 122 of the secondary capsule 120. One or more active ingredients or medicaments (e.g., pharmaeceutical, biotechnical, nutraceutical, vitamin, dietary supplement, mineral or combination thereof) may be introduced into at least a portion of the receiving chamber 128 of the secondary capsule 120, together with the introduction of the tertiary capsule 130 comprising its active ingredient(s). The secondary capsule 120 having its active ingredient(s) and housing the tertiary capsule 130 with its active ingredient(s) may then be selectively introduced within at least a portion of an internal periphery of a receiving chamber 118 of the primary capsule 111 defined between a base 114 and a corresponding cap 112. Preferably, the receiving chamber 118 of the primary capsule 111 may also include one or more active ingredients or medicaments (e.g., pharmaeceutical, biotechnical, nutraceutical, vitamin, dietary supplement, mineral or combination thereof) introduced therein.

Still referring to FIG. 2, another presently preferred embodiment of an encapsulation process for forming a multi-compartment capsule 110 may comprise the steps of: (1) providing a primary capsule 111 having a base 114, a corresponding cap 112 and a receiving chamber 118 defined between the base and cap; (2) providing a secondary capsule 120 having a base 124, a corresponding cap 122 and a receiving chamber 128 defined between the base and cap; (3) providing a tertiary capsule 130 having a base 134, a corresponding cap 132 and a receiving chamber 138 defined between the base and cap; (4) introducing at least one ingredient (e.g., pharmaeceutical, biotechnical, nutraceutical, vitamin, dietary supplement, mineral or combination thereof) having a first physical state (e.g., solid, liquid, gas or dispersion) into at least a portion of the receiving chamber 138 of the tertiary capsule 130 and selectively positioning the cap 132 in sealing relationship with the base 134; (5) introducing at least one ingredient (e.g., pharmaeceutical, biotechnical, nutraceutical, vitamin, dietary supplement, mineral or combination thereof) having a second physical state (e.g., solid, liquid, gas or dispersion) into at least a portion of the receiving chamber 128 of the secondary capsule 120, wherein the first physical state of the ingredient(s) in the tertiary capsule 130 are the same as the second physical state of the ingredient(s) in the secondary capsule 120; (6) introducing the tertiary capsule 130 into at least a portion of the receiving chamber 218 of the secondary capsule 120 and selectively positioning the cap 122 in sealing relationship with the base 124; (7) introducing at least one ingredient (e.g., pharmaeceutical, biotechnical, nutraceutical, vitamin, dietary supplement, mineral or combination thereof) having a third physical state (e.g., solid, liquid, gas or dispersion) into at least a portion of the receiving chamber 118 of the primary capsule 111, wherein the third physical state of the ingredient(s) in the primary capsule are different from the first and second physical states of the ingredient(s) in the tertiary capsule 130 and the secondary capsule 120, respectively; and (8) introducing the secondary capsule 120 into at least a portion of the receiving chamber 118 of the primary capsule 111 and selectively positioning the cap 112 in sealing relationship with the base 114 to form a single dosage multi-compartment capsule.

In the presently preferred embodiment illustrated in FIG. 2, a liquid may be selectively introduced into at least a portion of the internal periphery of the receiving chamber 118 of the primary capsule 111, a solid may be selectively introduced into at least a portion of the internal periphery of the receiving chamber 128 of the secondary capsule 120 and a solid may be selectively introduced into at least a portion of the receiving chamber 138 of the tertiary capsule 130. Although the ingredient(s) selectively introduced into the receiving chambers 118, 128, 138 of the primary, secondary and tertiary capsules 111, 120, 130, respectively, may be the same or different, the active ingredient(s) in at least two of the receiving chambers comprise at least two different physical states (e.g., solid, liquid, gas or dispersion). It is further contemplated herein as an alternate embodiment that the active ingredient(s) introduced in the receiving chamber 118 of the primary capsule 111 comprises a physical state (e.g., solid, liquid, gas or dispersion) different from the physical state of the active ingredient(s) contained within the receiving chamber 128 of the secondary capsule 120 which is different from the physical state of the active ingredient(s) contained within the receiving chamber 138 of the tertiary capsule 130. Those skilled in the art will readily recognize other possible modifications and adaptations relative to contemplated variations in physical states of the active ingredient(s) selectively introduced within the receiving chambers 118, 128, 138 of the primary, secondary and tertiary capsules, respectively, which are consistent with the spirit and scope of the present invention. It is intended, therefore, that the figures and examples provided herein be viewed as exemplary of the principles of the present invention, and not as restrictive to a particular structure or method for implementing those principles.

Figure 3:
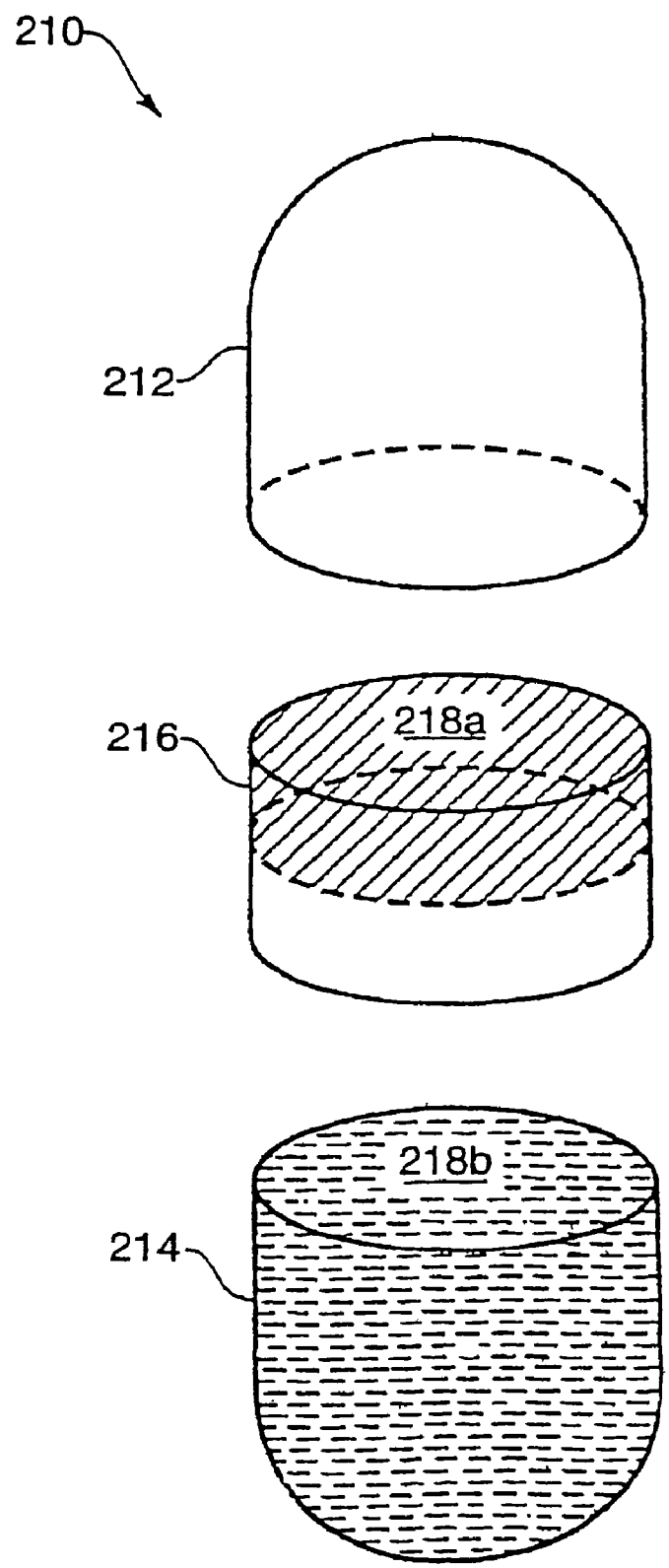
FIG. 3 is a perspective view illustrating yet another presently preferred embodiment of a multi-compartment capsule comprising a base, a cap and a dividing wall positioned between the base and the cap, wherein the dividing wall facilitates the formation of at least two, independent receiving chambers for receiving one or more active ingredients or medicaments having different physical states.
Figure 4:
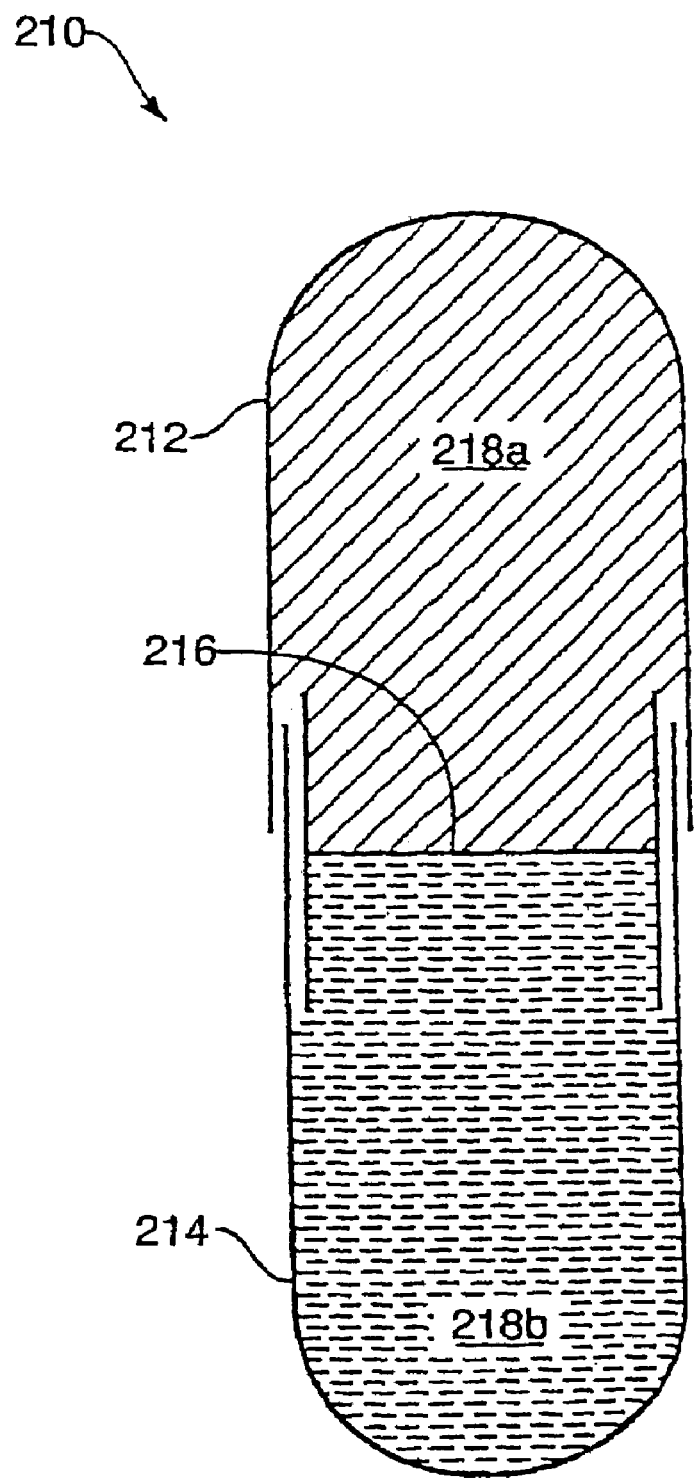
FIG. 4 is a cross-sectional view of the multi-compartment capsule shown in FIG. 3 wherein the base, the dividing wall defining the two receiving chambers and the cap are assembled to form a capsule of the present invention and wherein one or more active ingredients or medicaments having different physical states are introduced into the receiving chambers.

Referring now to FIGS. 3 and 4, another presently preferred embodiment of a multi-compartment capsule 210 is shown comprising a base 214, a corresponding cap 212 and a dividing wall 216 positionable between the base and the cap. Structurally, the size, shape and positioning of the dividing wall 216 relative to the base 214 and corresponding cap 212 facilitates the formation of at least two, independent and separate receiving chambers 218a, 218b, each having an internal periphery sufficient for receiving one or more active ingredients or medicaments (e.g., pharmaeceutical, biotechnical, nutraceutical, vitamin, dietary supplement, mineral or combination thereof) therein. As best shown in FIG. 4, the dividing wall 216 seats within the internal periphery of both the base 214 and the corresponding cap 212. After introducing one or more active ingredients or medicaments into receiving chamber 218b and disposing the dividing wall 216 relative thereto, one or more active ingredients or medicaments (e.g., pharmaeceutical, biotechnical, nutraceutical, vitamin, dietary supplement, mineral or combination thereof) may be introduced into receiving chamber 218a and the cap may be selectively positioned in sealing relationship with the base 214 to form one presently preferred embodiment of the single, dosage multi-compartment capsule 210. Moreover, the dividing wall 216 may functionally assist in forming a sealing relationship between the base 214 and corresponding cap 212 of the multi-compartment capsule 210, if desired.

In one presently preferred embodiment of the multi-compartment capsule 211 of the present invention, a solid may be selectively introduced into at least a portion of the internal periphery of the receiving chamber 218a and a liquid may be selectively introduced into at least a portion of the internal periphery of the receiving chamber 218b. Although the ingredient(s) introduced into the receiving chamber 218a may be the same or different from the ingredient(s) introduced into the receiving chamber 218, the active ingredient(s) in the first receiving chamber 218a preferably comprise a physical state (e.g., solid, liquid, gas or dispersion) that is different from the physical state of the active ingredient(s) in the second receiving chamber 218b. Those skilled in the art will readily recognize other possible modifications and adaptations relative to the contemplated variations in physical states (e.g., solid, liquid, gas and dispersion) of the active ingredient(s) selectively positionable within the receiving chambers 218a, 218b which are consistent with the spirit and scope of the present invention. It is intended, therefore, that the figures and examples provided herein be viewed as exemplary of the principles of the present invention, and not as restrictive to a particular structure or method for implementing those principles.

Figure 5:
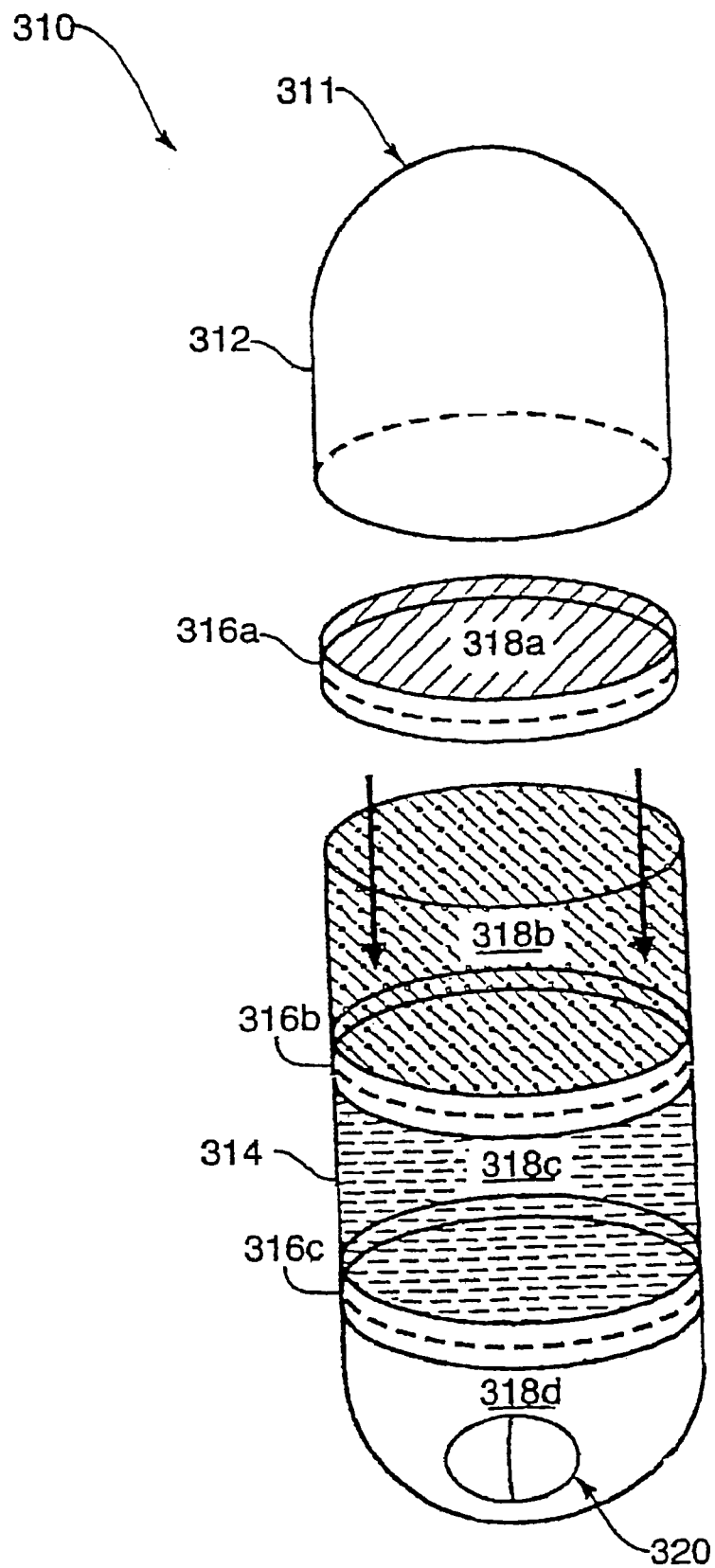
FIG. 5 is a perspective view illustrating an alternate presently preferred embodiment of a multi-compartment capsule of the present invention having a primary capsule comprising a capsular base configured with a longitudinally extending body, a corresponding cap and a series of dividing walls disposed in spaced apart relationship along the length of the longitudinally extending body of the base, wherein the dividing walls define a plurality of independent receiving chambers having an internal periphery sufficient for introducing one or more active ingredients or medicaments having different physical states therein and for introducing a secondary capsule, having one or more active ingredients contained therein, within at least one of said receiving chambers.
Figure 6:
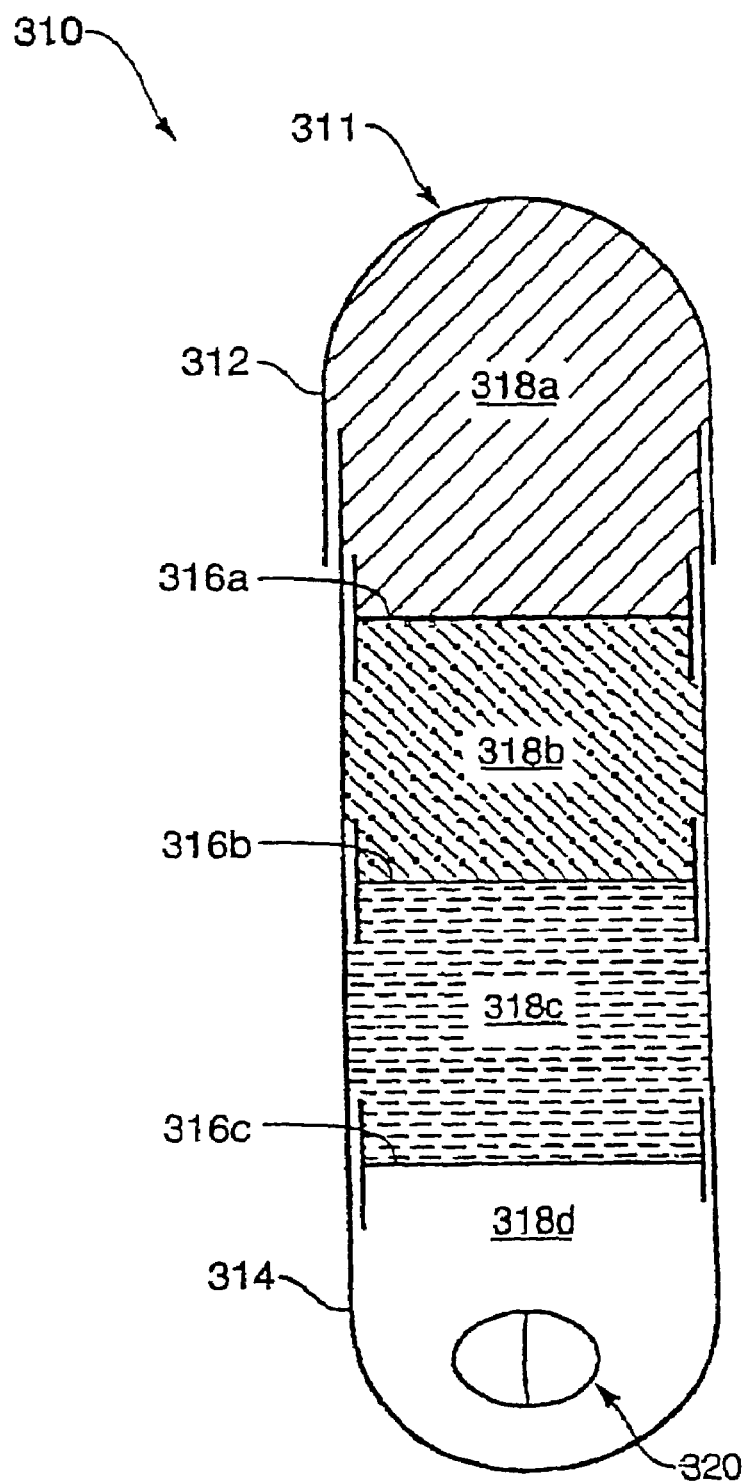
FIG. 6 is a cross-sectional view of the multi-compartment capsule shown in FIG. 5 wherein the base and the cap are assembled to form a single dosage capsule having a series of dividing walls that define a plurality of chambers for receiving one or more active ingredients or medicaments, wherein the active ingredient(s) in at least two of the receiving chambers comprise different physical states.

Referring now to FIGS. 5 and 6, another presently preferred embodiment of a multi-compartment capsule, designated as 310, is shown including a primary capsule 311 comprising a capsular base 314 configured having an elongated or longitudinally extending body, a corresponding cap 312 and a plurality of dividing walls 316 selectively disposed along the length of the longitudinally extending body of the base. Preferably, the structural size, shape and positioning of the dividing walls 316a, 316b, 316c along the length of the elongated body of the base 314 facilitate the formation of a plurality of independent receiving chambers 318a, 318b, 318c, 318d. Each receiving chamber 318a, 318b, 318c, 318d of the primary capsule 311 having an internal periphery sufficient for receiving one or more active ingredients or medicaments (e.g., pharmaeceutical, biotechnical, nutraceutical, vitamin, dietary supplement, mineral or combination thereof) therein.

As best shown in FIG. 6, the dividing walls 316a, 316b, 316c are preferably seated within the internal periphery of the base 314 of the primary capsule 311 and in a spaced apart relationship along the length of the longitudinally extending body and form four independent receiving chambers 318a, 318b, 318c, 318d. In one presently preferred embodiment of the multi-compartment capsule 310 of the present invention, each of the receiving chambers 318a, 318b, 318c comprises at least one active ingredient or medicament having a physical state (e.g., solid, liquid, gas or dispersion) different from the physical state of the ingredient(s) in the other receiving chambers.

As illustrated by way of example, and not by way of restriction, a solid may be selectively introduced into at least a portion of the internal periphery of the receiving chamber 318a, a dispersion may be selectively introduced into at least a portion of the internal periphery of the receiving chamber 318b, a liquid may be selectively introduced into at least a portion of the internal periphery of the receiving chamber 318c and a secondary capsule 320 may be selectively introduced into at least a portion of the internal periphery of the receiving chamber 318d. As contemplated herein, receiving chamber 318d may be further configured having an internal periphery sufficient for receiving a secondary capsule 320, together with at least one active ingredient or medicament therein.

One presently preferred embodiment of an encapsulation process, as defined by the structural configuration of the multi-compartment capsule 310 illustrated in FIGS. 5 and 6, may comprise the steps of: (1) introducing a secondary capsule 320 (e.g., tablet) and one or more active ingredients or medicaments into receiving chamber 318d; (2) selectively positioning dividing wall 316c along the length of the elongated body of the base 314; (3) introducing one or more active ingredients or medicaments (e.g., pharmaeceutical, biotechnical, nutraceutical, vitamin, dietary supplement, mineral or combination thereof) into receiving chamber 318c; (4) selectively positioning dividing wall 316b along the length of the elongated body of the base 314 in a spaced apart relationship to dividing wall 316c; (5) introducing one or more active ingredients or medicaments (e.g., pharmaeceutical, biotechnical, nutraceutical, vitamin, dietary supplement, mineral or combination thereof) into receiving chamber 318b; (6) selectively positioning dividing wall 316a along the length of the elongated body of the base 314 in a spaced apart relationship to dividing wall 316b; and (7) selectively positioning the cap 312 in sealing relationship with the base 314 to form a presently preferred embodiment of a single, dosage multi-compartment capsule 310. The dividing wall 316a may also function in the formation of the sealing relationship between the base 314 and the corresponding cap 312, if desired.

Although the ingredient(s) introduced into one of the receiving chambers 318 may be the same ingredient or may be different from the ingredient(s) introduced into the other receiving chambers, the active ingredient(s) in at least two of the receiving chambers 318 preferably comprise a physical state (e.g., solid, liquid, gas or dispersion) that is different from the physical state of the active ingredient(s) in one or more of the remaining receiving chambers. Those skilled in the art will readily recognize other possible modifications and adaptations relative to the contemplated variations in physical states (e.g., solid, liquid, gas and dispersion) of the active ingredient(s) selectively introduced within the receiving chambers 318 which are consistent with the spirit and scope of the present invention. It is intended, therefore, that the figures and examples provided herein be viewed as exemplary of the principles of the present invention, and not as restrictive to a particular structure or method for implementing those principles.

Figure 7:
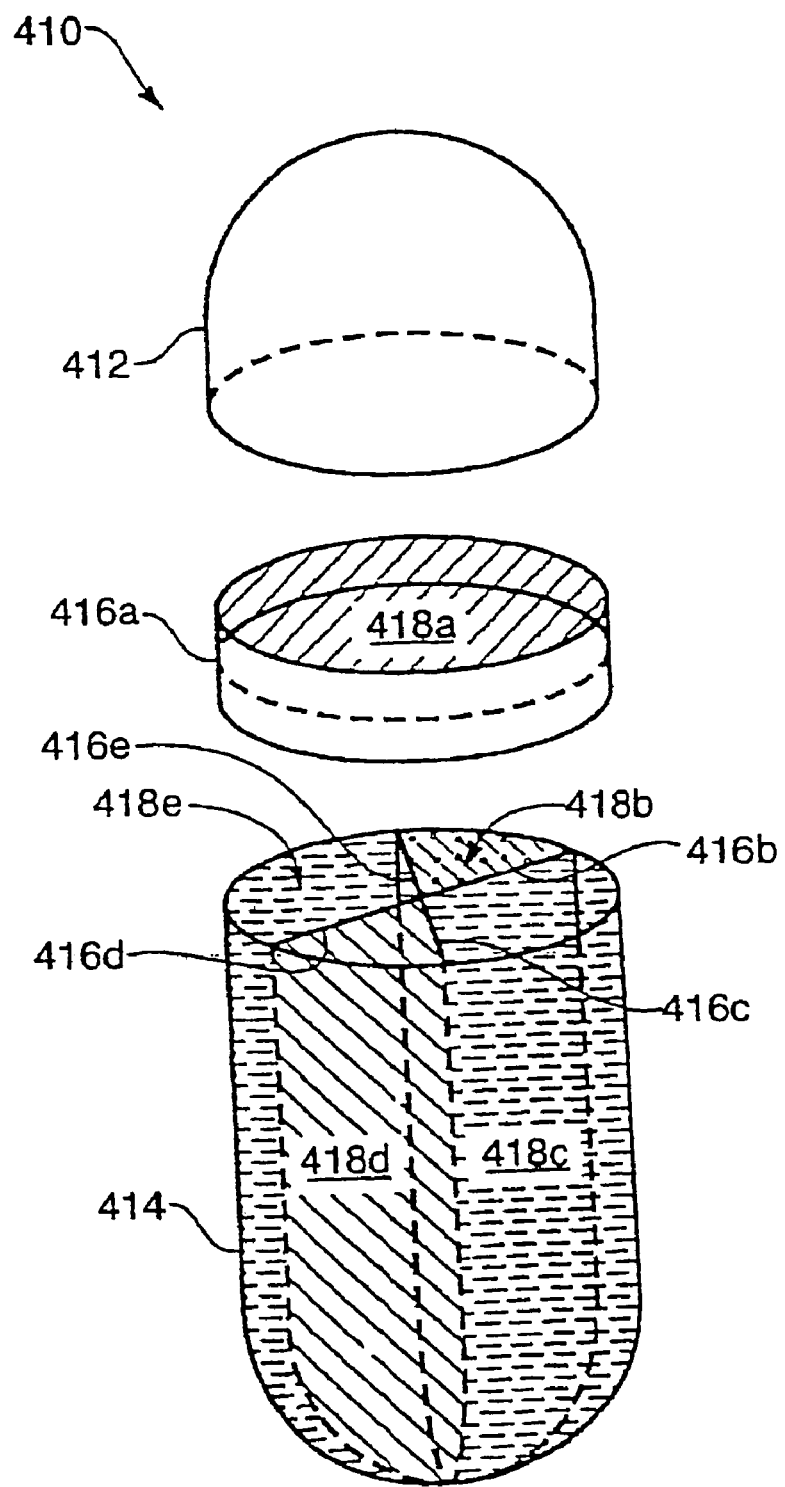
FIG. 7 is a perspective view illustrating yet another presently preferred embodiment of a multi-compartment capsule of the present invention having a primary capsule comprising a capsular base configured with a longitudinally extending body, a corresponding cap and a series of dividing walls disposed in spaced apart relationship, both vertically and horizontally, along the length of the longitudinally extending body of the base, wherein the dividing walls define a plurality of independent receiving chambers having an internal periphery sufficient for introducing one or more active ingredients or medicaments having different physical states therein.

Another presently preferred embodiment of a multi-compartment capsule of the present invention, generally designated as 410 in FIG. 7, is shown comprising a capsular base 414 preferably configured having an elongated or longitudinally extending body, a corresponding cap 412 and a plurality of dividing walls 416 selectively disposed along the length of the longitudinally extending body of the base, both horizontally and vertically. In structural design, the size, shape and positioning of the dividing walls 416a, 416b, 416c, 416d, 416e along the length of the longitudinally extending body of the base 414 facilitate the formation of a plurality of independent receiving chambers 418.

In one presently preferred embodiment, the dividing walls 416a, 416b, 416c, 416d, 416e are preferably disposed or seated in a spaced apart relationship within the internal periphery of the base 414 of the primary capsule 411 along the length of the longitudinally extending body, whereby forming five (5) independent receiving chambers 418a, 418b, 418c, 418d, 418e. Each receiving chamber 418a, 418b, 418c, 418d, 418e of the primary capsule 411 are preferably configured having an internal periphery dimensionally sufficient for receiving one or more active ingredients or medicaments (e.g., pharmaeceutical, biotechnical, nutraceutical, vitamin, dietary supplement, mineral or combination thereof) therein.

Still referring to FIG. 7, one presently preferred embodiment of an encapsulation process, as defined by the structural configuration of the multi-compartment capsule 410, may comprise the steps of: (1) introducing one or more active ingredients or medicaments into receiving chamber 418e defined by dividing walls 416d, 416e which are vertically disposed along the length of the elongated body of the base 414; (2) introducing one or more active ingredients or medicaments into receiving chamber 418d defined by dividing walls 416c, 416d which are vertically disposed along the length of the elongated body of the base 414; (3) introducing one or more active ingredients or medicaments into receiving chamber 418c defined by dividing walls 416b, 416c which are vertically disposed along the length of the elongated body of the base 414; (4) introducing one or more active ingredients or medicaments into receiving chamber 418b defined by dividing walls 416b, 416e which are vertically disposed along the length of the elongated body of the base 414; (5) disposing dividing wall 416a along the length of the elongated body of the base 414 perpendicular to the disposition of dividing walls 416b, 416c, 416d, 416e and introducing one or more active ingredients or medicaments into receiving chamber 418a; and (6) selectively positioning the cap 412 in sealing relationship with the base 414 to form one presently preferred embodiment of a single, dosage multi-compartment capsule 410. As appreciated, the dividing wall 416a may also function in the formation of the sealing relationship between the base 414 and the corresponding cap 412, if structurally desired.

As illustrated by way of example, and not by way of restriction, a solid may be selectively introduced into at least a portion of the internal periphery of the receiving chamber 418a, a dispersion may be selectively introduced into at least a portion of the internal periphery of the receiving chamber 418b, a liquid may be selectively introduced into at least a portion of the internal periphery of the receiving chamber 418c, a solid may be selectively introduced into at least a portion of the internal periphery of the receiving chamber 418d and a liquid may be selectively introduced into at least a portion of the internal periphery of the receiving chamber 418e.

Although the ingredient(s) introduced into one of the receiving chambers 418 may be the same ingredient or may be different from the ingredient(s) introduced into the other receiving chambers, the active ingredient(s) in at least two of the receiving chambers 418 preferably comprise a physical state (e.g., solid, liquid, gas or dispersion) that is different from the physical state of the active ingredient(s) in one or more of the remaining receiving chambers. Those skilled in the art will readily recognize other possible modifications and adaptations relative to the contemplated variations in physical states (e.g., solid, liquid, gas and dispersion) of the active ingredient(s) selectively introduced within the receiving chambers 418 which are consistent with the spirit and scope of the present invention. It is intended, therefore, that the figures and examples provided herein be viewed as exemplary of the principles of the present invention, and not as restrictive to a particular structure or method for implementing those principles.

Figure 8:
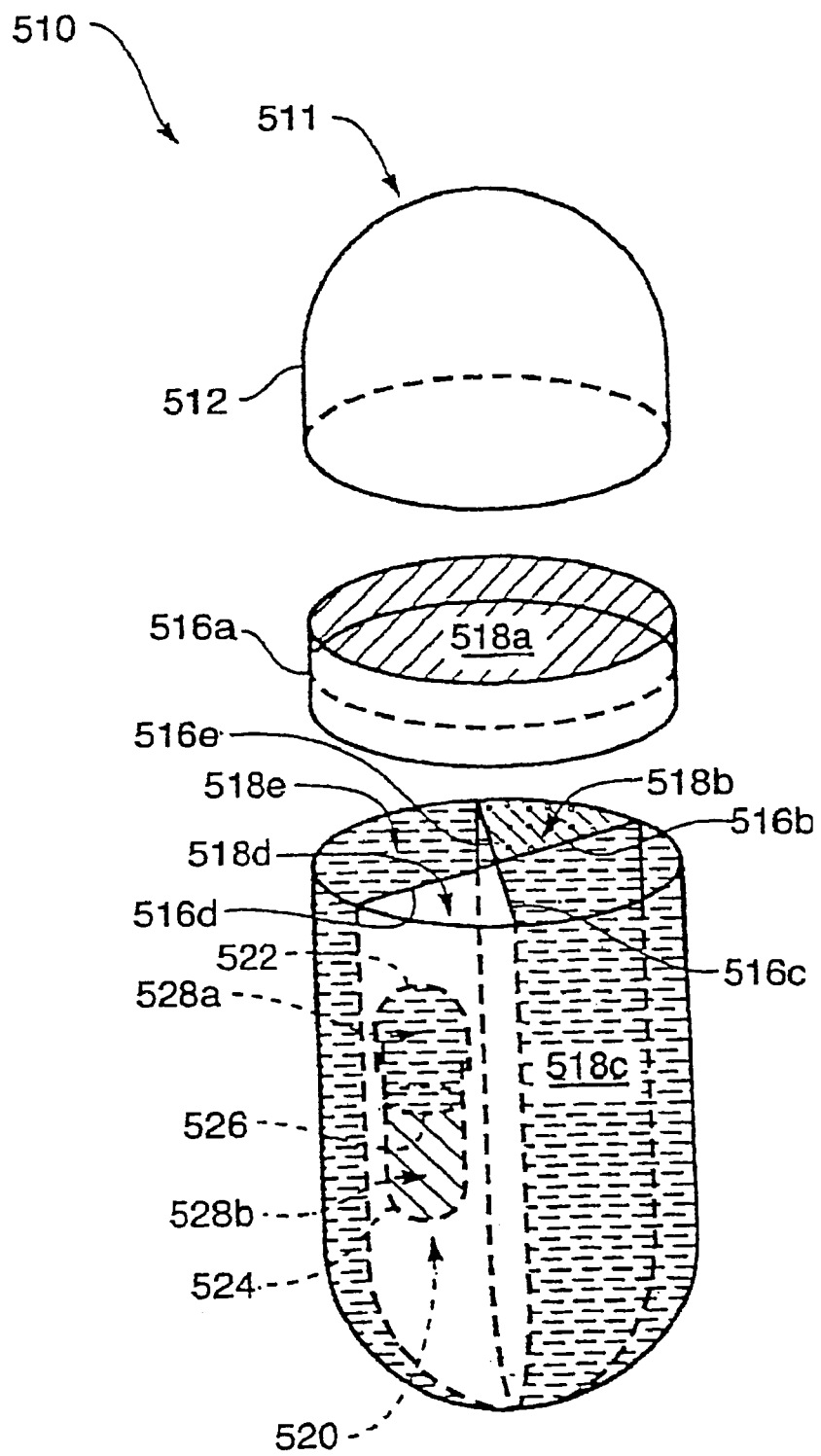
FIG. 8 is a perspective view illustrating an alternate preferred embodiment of the multi-compartment capsule shown in FIG. 7, wherein the multi-compartment capsule includes a primary capsule comprising a capsular base configured with a longitudinally extending body, a corresponding cap and a series of dividing walls disposed in spaced apart relationship, both vertically and horizontally, along the length of the longitudinally extending body of the base, wherein the dividing walls define a plurality of independent receiving chambers having an internal periphery sufficient for introducing one or more active ingredients or medicaments having different physical states therein and for introducing a secondary capsule, having one or more active ingredients contained therein, within at least one of said receiving chambers.

Referring now to FIG. 8, an alternate presently preferred embodiment of a multi-compartment capsule 510 includes a capsular base 514 preferably configured having an elongated or longitudinally extending body, a corresponding cap 512 and a plurality of dividing walls 516 selectively disposed along the length of the longitudinally extending body of the base, both horizontally and vertically. In structural design, the size, shape and positioning of the dividing walls 516a, 516b, 516c, 516d along the length of the longitudinally extending body of the base 514 facilitate the formation of a plurality of independent receiving chambers 518.

In one presently preferred embodiment, the dividing walls 516a, 516b, 516c, 516d, 516e are preferably disposed or seated in a spaced apart relationship within the internal periphery of the base 514 of the primary capsule 511 along the length of the longitudinally extending body, whereby forming five (5) independent receiving chambers 518a, 518b, 518c, 518d, 518e. Each of the receiving chamber 518a, 518b, 518c, 518d, 518e of the primary capsule 411 are preferably configured having an internal periphery dimensionally sufficient for receiving one or more active ingredients or medicaments (e.g., pharmaeceutical, biotechnical, nutraceutical, vitamin, dietary supplement, mineral or combination thereof) therein. Moreover, receiving chamber 518d is formed having an internal periphery sufficient for receiving a secondary capsule 520. The secondary capsule 520 being configured with a base 524, corresponding cap 522 and a dividing wall 526 defining a first receiving chamber 528a and a second receiving chamber 528b. The first receiving chamber 528a is preferably configured having an internal periphery sufficient for receiving one or more active ingredients or medicaments (e.g., pharmaeceutical, biotechnical, nutraceutical, vitamin, dietary supplement, mineral or combination thereof) having a first physical state (e.g., solid, liquid, gas or dispersion) therein. Similarly, the second receiving chamber 528b is configured having an internal periphery sufficient for receiving one or more active ingredients or medicaments (e.g., pharmaeceutical, biotechnical, nutraceutical, vitamin, dietary supplement, mineral or combination thereof) having a second physical state (e.g., solid, liquid, gas or dispersion), wherein the physical state of the ingredient(s) in the second receiving chamber varies from the physical state of the ingredient(s) in the first receiving chamber. As contemplated and disclosed hereinabove, after the ingredients are introduced into the respective receiving chambers 528a, 528b, the cap 522 may be positioned in sealing relationship with the base 524 of the secondary capsule 520.

Still referring to FIG. 8, as illustrated by way of example, and not by way of restriction, a solid may be selectively introduced into at least a portion of the internal periphery of the receiving chamber 528a and a liquid may be selectively introduced into at least a portion of the internal periphery of the receiving chamber 528b. Although the ingredient(s) introduced into one of the receiving chamber 528a may be the same ingredient or may be different from the ingredient(s) introduced into receiving chamber 528b, the active ingredient(s) in the first receiving chamber 528a comprise a physical state (e.g., solid, liquid, gas or dispersion) that is different from the physical state of the active ingredient(s) in receiving chambers 528b. Those skilled in the art will readily recognize other possible modifications and adaptations relative to the contemplated variations in physical states (e.g., solid, liquid, gas and dispersion) of the active ingredient(s) selectively introduced within the receiving chambers 528 which are consistent with the spirit and scope of the present invention. It is intended, therefore, that the figures and examples provided herein be viewed as exemplary of the principles of the present invention, and not as restrictive to a particular structure or method for implementing those principles One presently preferred embodiment of an encapsulation process, as defined by the structural configuration of the multi-compartment capsule 510, may comprise the steps of: (1) introducing one or more active ingredients or medicaments (e.g., pharmaeceutical, biotechnical, nutraceutical, vitamin, dietary supplement, mineral or combination thereof) into receiving chamber 518e defined by dividing walls 516d, 516e which are disposed vertically along the length of the elongated body of the base 514; (2) introducing a secondary capsule 520 into receiving chamber 518d defined by dividing walls 516c, 516d which are disposed vertically along the length of the elongated body of the base 514; (3) introducing one or more active ingredients or medicaments (e.g., pharmaeceutical, biotechnical, nutraceutical, vitamin, dietary supplement, mineral or combination thereof) into receiving chamber 518c defined by dividing walls 516b, 516c which are disposed vertically along the length of the elongated body of the base 514; (4) introducing one or more active ingredients or medicaments (e.g., pharmaeceutical, biotechnical, nutraceutical, vitamin, dietary supplement, mineral or combination thereof) into receiving chamber 518b defined by dividing walls 516b, 516e which are disposed vertically along the length of the elongated body of the base 514; (5) disposing dividing wall 516a along the length of the elongated body of the base 514 perpendicular to the disposition of dividing walls 516b, 516c, 516d, 516e and introducing one or more active ingredients or medicaments (e.g., pharmaeceutical, biotechnical, nutraceutical, vitamin, dietary supplement, mineral or combination thereof) into receiving chamber 518a; and (6) selectively positioning the cap 512 in sealing relationship with the base 514 to form one presently preferred embodiment of a single, dosage multi-compartment capsule 510. As appreciated, the dividing wall 516a may also function in the formation of the sealing relationship between the base 514 and the corresponding cap 512, if structurally desired.

As illustrated by way of example, and not by way of limitation, a solid may be selectively introduced into at least a portion of the internal periphery of receiving chamber 518a, a dispersion may be selectively introduced into at least a portion of the internal periphery of receiving chamber 518b, a liquid may be selectively introduced into at least a portion of the internal periphery of the receiving chamber 518c and a liquid may be selectively introduced into at least a portion of the internal periphery of the receiving chamber 518e. Although the ingredient(s) introduced into one of the receiving chambers 518 may be the same ingredient or may be different from the ingredient(s) introduced into the other receiving chambers, the active ingredient(s) in at least two of the receiving chambers 518 preferably comprise a physical state (e.g., solid, liquid, gas or dispersion) that is different from the physical state of the active ingredient(s) in one or more of the remaining receiving chambers. Those skilled in the art will readily recognize other possible modifications and adaptations relative to the contemplated variations in physical states (e.g., solid, liquid, gas and dispersion) of the active ingredient(s) selectively introduced within the receiving chambers 518 which are consistent with the spirit and scope of the present invention. It is intended, therefore, that the figures and examples provided herein be viewed as exemplary of the principles of the present invention, and not as restrictive to a particular structure or method for implementing those principles.

Figure 9:
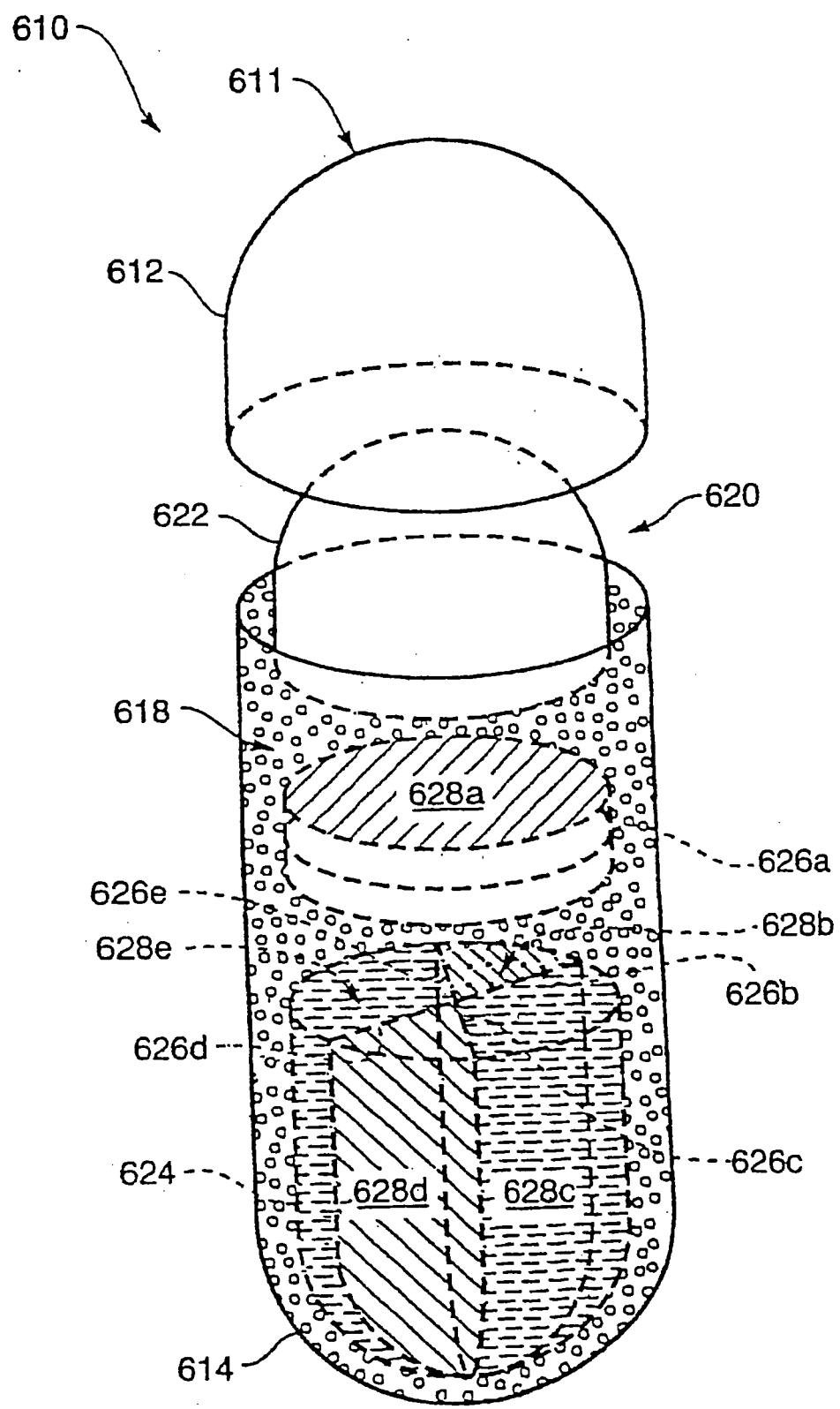
FIG. 9 is a perspective view illustrating yet another presently preferred embodiment of a multi-compartment capsule of the present invention wherein the multi-compartment capsule shown in FIG. 7 is introduced within the internal periphery of a receiving chamber of a primary capsule having one or more active ingredients also contained therein.

Referring now to FIG. 9, yet another presently preferred embodiment of a multi-compartment capsule of the present invention, generally designated as 610, is shown comprising a primary capsule 611 and a secondary capsule 620 selectively positionable within at least a portion of an internal periphery of the primary capsule. The primary capsule 611 having a receiving chamber 618 preferably formed having an internal periphery sufficient for receiving the secondary capsule 620, together with one or more active ingredients or medicaments (e.g., pharmaeceutical, biotechnical, nutraceutical, vitamin, dietary supplement, mineral or combination thereof) therein. The secondary capsule 620 comprising a capsular base 624 preferably configured having an elongated or longitudinally extending body, a corresponding cap 622 and a plurality of dividing walls 626 selectively disposed along the length of the longitudinally extending body of the base, both horizontally and vertically. In structural design, the size, shape and positioning of the dividing walls 626a, 626b, 626c, 626d along the length of the longitudinally extending body of the base 624 facilitate the formation of a plurality of independent receiving chambers 628.

In one presently preferred embodiment, the dividing walls 626a, 626b, 626c, 626d, 626e are preferably disposed or seated in a spaced apart relationship within the internal periphery of the base 624 of the secondary capsule 620 along the length of the longitudinally extending body, whereby forming five (5) independent receiving chambers 628a, 628b, 628c, 628d, 628e. Each receiving chamber 628a, 628b, 628c, 628d, 628e of the secondary capsule 620 are preferably configured having an internal periphery dimensionally sufficient for receiving one or more active ingredients or medicaments (e.g., pharmaeceutical, biotechnical, nutraceutical, vitamin, dietary supplement, mineral or combination thereof) therein.

One presently preferred embodiment of an encapsulation process, as defined by the structural configuration of the multi-compartment capsule 610, may comprise the steps of: (1) introducing one or more active ingredients or medicaments (e.g., pharmaeceutical, biotechnical, nutraceutical, vitamin, dietary supplement, mineral or combination thereof) into receiving chamber 628e defined by dividing walls 626d, 626e which are vertically disposed along the length of the elongated body of the base 624; (2) introducing one or more active ingredients or medicaments (e.g., pharmaeceutical, biotechnical, nutraceutical, vitamin, dietary supplement, mineral or combination thereof) into receiving chamber 628d defined by dividing walls 626c, 626d which are vertically disposed along the length of the elongated body of the base 624; (3) introducing one or more active ingredients or medicaments (e.g., pharmaeceutical, biotechnical, nutraceutical, vitamin, dietary supplement, mineral or combination thereof) into receiving chamber 628c defined by dividing walls 626b, 626c which are vertically disposed along the length of the elongated body of the base 624; (4) introducing one or more active ingredients or medicaments (e.g., pharmaeceutical, biotechnical, nutraceutical, vitamin, dietary supplement, mineral or combination thereof) into receiving chamber 628b defined by dividing walls 626b, 626e which are vertically disposed along the length of the elongated body of the base 624; (5) disposing dividing wall 626a along the length of the elongated body of the base 624 perpendicular to the disposition of dividing walls 626b, 626c, 626d, 626e and introducing one or more active ingredients or medicaments (e.g., pharmaeceutical, biotechnical, nutraceutical, vitamin, dietary supplement, mineral or combination thereof) into receiving chamber 628a; (6) selectively positioning the cap 622 in sealing relationship with the base 624 of the secondary capsule 620; (7) introducing the secondary capsule 620 and one or more ingredients or medicaments (e.g., pharmaeceutical, biotechnical, nutraceutical, vitamin, dietary supplement, mineral or combination thereof) into the receiving chamber 618 of the primary capsule 611; and (8) selectively positioning the cap 612 in sealing relationship with the base 614 of the primary capsule 611 to form one presently preferred embodiment of a single, dosage multi-compartment capsule 610.

As illustrated by way of example, and not by way of restriction, a solid may be selectively introduced into at least a portion of the internal periphery of the receiving chamber 628a, a dispersion may be selectively introduced into at least a portion of the internal periphery of the receiving chamber 628b, a liquid may be selectively introduced into at least a portion of the internal periphery of the receiving chamber 628c, a solid may be selectively introduced into at least a portion of the internal periphery of the receiving chamber 628d and a liquid may be selectively introduced into at least a portion of the internal periphery of the receiving chamber 628e of the secondary capsule 620. In addition, a gas may be introduced into at least a portion of the internal periphery of the receiving chamber 618 of the primary capsule 611.

Although the ingredient(s) introduced into one of the receiving chambers 618, 628 of the primary and secondary capsules, respectively, may be the same ingredient or may be different from the ingredient(s) introduced into the other receiving chambers, the active ingredient(s) in at least two of the receiving chambers 618, 628 preferably comprise a physical state (e.g., solid, liquid, gas or dispersion) that is different from the physical state of the active ingredient(s) in one or more of the remaining receiving chambers. Those skilled in the art will readily recognize other possible modifications and adaptations relative to the contemplated variations in physical states (e.g., solid, liquid, gas and dispersion) of the active ingredient(s) selectively introduced within the receiving chambers 618, 628 which are consistent with the spirit and scope of the present invention. It is intended, therefore, that the figures and examples provided herein be viewed as exemplary of the principles of the present invention, and not as restrictive to a particular structure or method for implementing those principles.

Figure 10:
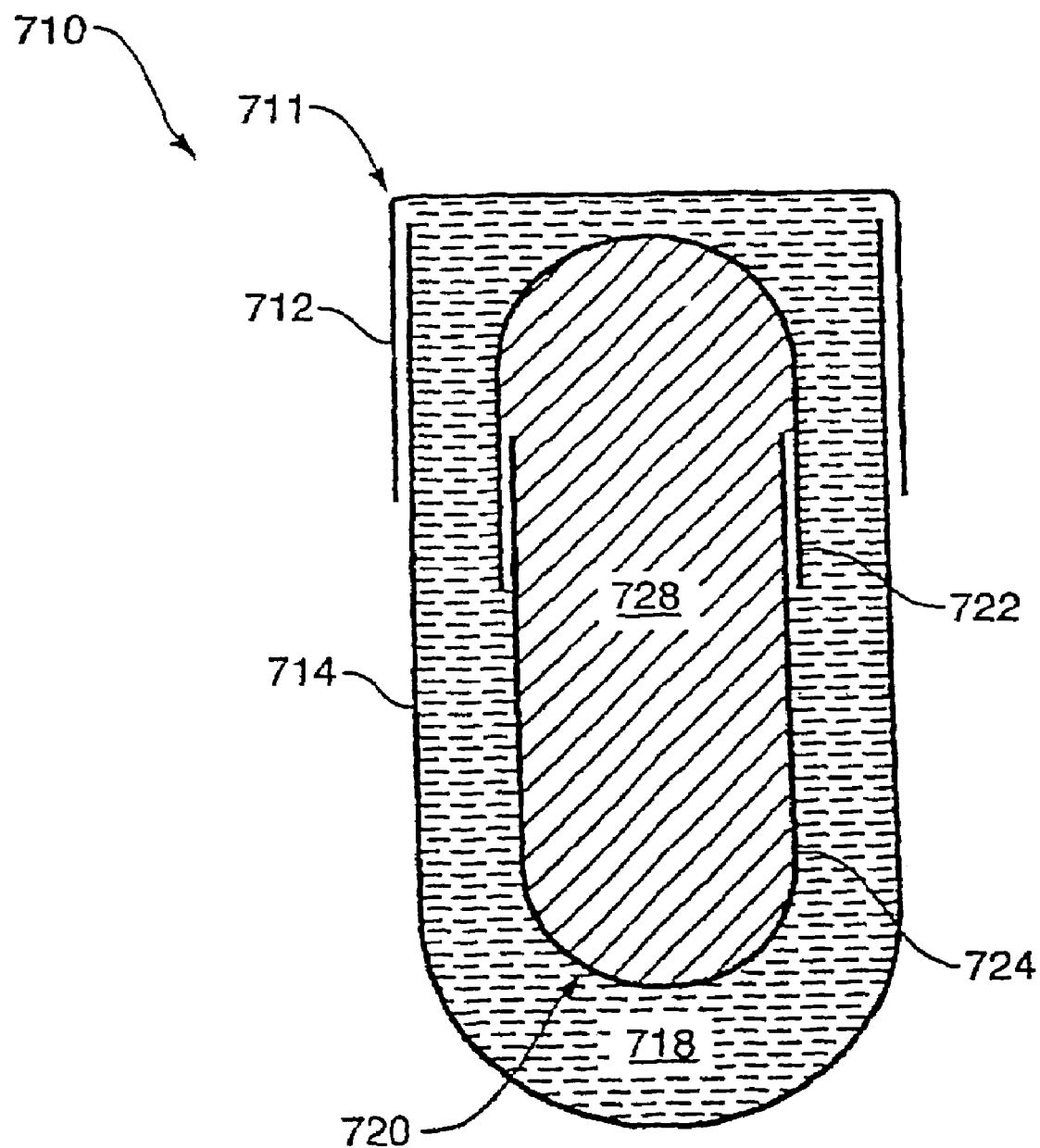
FIG. 10 is a cross-sectional view illustrating a presently preferred embodiment of a multi-compartment capsule of the present invention including a secondary capsule having one or more active ingredients or medicaments selectively introduced into the internal periphery of a primary capsule having one or more active ingredients or medicaments, wherein the active ingredient(s) introduced into the primary capsule comprises a physical state (e.g., solid, liquid, gas or dispersion) which differs from the physical state of the active ingredient(s) introduced into the internal periphery of the secondary capsule, the primary capsule further comprising a cap having a generally U-shaped configuration adapted to provide a sealing relationship when engaging the corresponding base, thereby reducing dead space volume in the internal periphery of the receiving chamber of the base.

Another presently preferred embodiment of a multi-compartment capsule of the present invention, generally designated as 710 in FIG. 10, is shown comprising a secondary capsule 720 including one or more active ingredients or medicaments (e.g., pharmaeceutical, biotechnical, nutraceutical, vitamin, dietary supplement, mineral or combination thereof) within at least a portion of the internal periphery of a receiving chamber 728 and having a size and shape sufficient for being selectively introduced within at least a portion of the internal periphery of a receiving chamber 718 of a primary capsule 711. The primary capsule 711 also includes one or more active ingredients or medicaments (e.g., pharmaeceutical, biotechnical, nutraceutical, vitamin, dietary supplement, mineral or combination thereof) introduced within the internal periphery of the receiving chamber 718, wherein the active ingredient(s) introduced into the primary capsule comprises a physical state (e.g., solid, liquid, gas or dispersion) which differs from the physical state of the active ingredient(s) introduced into the internal periphery of the secondary capsule. In structural design, the primary capsule 711 further comprises a cap 712 having a generally U-shaped configuration adapted to provide a sealing relationship when engaging the corresponding base 714, thereby reducing dead space volume in the internal periphery of the receiving chamber 718 of the base. In this regard, the configuration of the cap 712 generally eliminates or substantially reduces the potential dead space volume within the internal periphery of the receiving chamber 718, thus functionally negating the opportunity for reaction between an air bubble and the active ingredient(s) introduced into the base 714 of the primary capsule 711.

One presently preferred embodiment of an encapsulation process, as defined by the structural configuration of the multi-compartment capsule 710, may include the steps of: (1) introducing one or more active ingredients or medicaments (e.g., pharmaeceutical, biotechnical, nutraceutical, vitamin, dietary supplement, mineral or combination thereof) into receiving chamber 728; (2) selectively positioning the cap 722 in sealing relationship with the base 724 of the secondary capsule 720; (3) introducing one or more active ingredients or medicaments (e.g., pharmaeceutical, biotechnical, nutraceutical, vitamin, dietary supplement, mineral or combination thereof), together with the secondary capsule 720, into the receiving chamber 718 of the primary capsule 711; and (4) selectively positioning the cap 712 having a general U-shaped configuration in sealing relationship with the base 714 of the primary capsule 711 to form a presently preferred embodiment of a single, dosage multi-compartment capsule 710, wherein eliminating or substantially reducing dead space volume within the internal periphery of the receiving chamber 718.

A solid is selectively introduced within at least a portion of the internal periphery of the receiving chamber 728 of the secondary capsule 720 and a liquid is selectively introduced within at least a portion of the internal periphery of the receiving chamber 718 of the primary capsule 711. Although the ingredient(s) introduced into the receiving chamber 718 of the primary capsule 711 may be the same or different from the ingredient(s) introduced into the receiving chamber 728 of the secondary capsule 720, the active ingredient(s) in the primary capsule have a physical state (i.e., solid, liquid, gas or dispersion) that various from the physical state of the active ingredient(s) in the secondary capsule. Accordingly, those skilled in the art will readily recognize other possible modifications and adaptations relative to the contemplated variations in physical states of the active ingredient(s) selectively introduced within the receiving chambers 718, 728 of the primary and secondary capsules 711, 720, respectively, which are consistent with the spirit and scope of the present invention. It is intended, therefore, that the figures and examples provided herein be viewed as exemplary of the principles of the present invention, and not as restrictive to a particular structure or method for implementing those principles.

Figure 11:
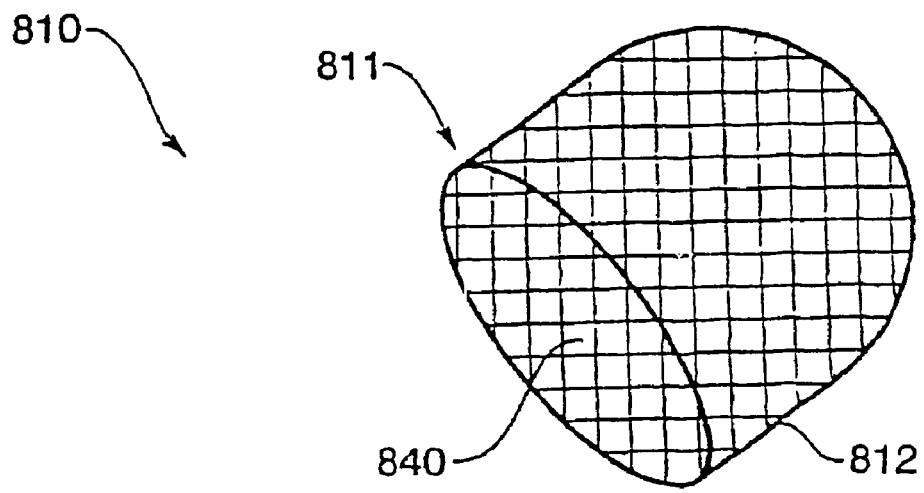
FIG. 11 is a perspective view illustrating yet another presently preferred embodiment of a multi-compartment capsule of the present invention including a secondary capsule having one or more active ingredients or medicaments and having a size and shape sufficient for being selectively introduced into the internal periphery of a primary capsule having one or more active ingredients or medicaments, wherein the active ingredient(s) introduced into the primary capsule comprises a physical state (e.g., solid, liquid, gas or dispersion) which differs from the physical state of the active ingredient(s) introduced into the internal periphery of the secondary capsule, the primary capsule further comprising a filling material introduced into the internal periphery of the cap having a general conical configuration and adapted to provide a sealing relationship when engaging the corresponding base, thereby reducing dead space volume in the internal periphery of the receiving chamber of the base.
Figure 11:
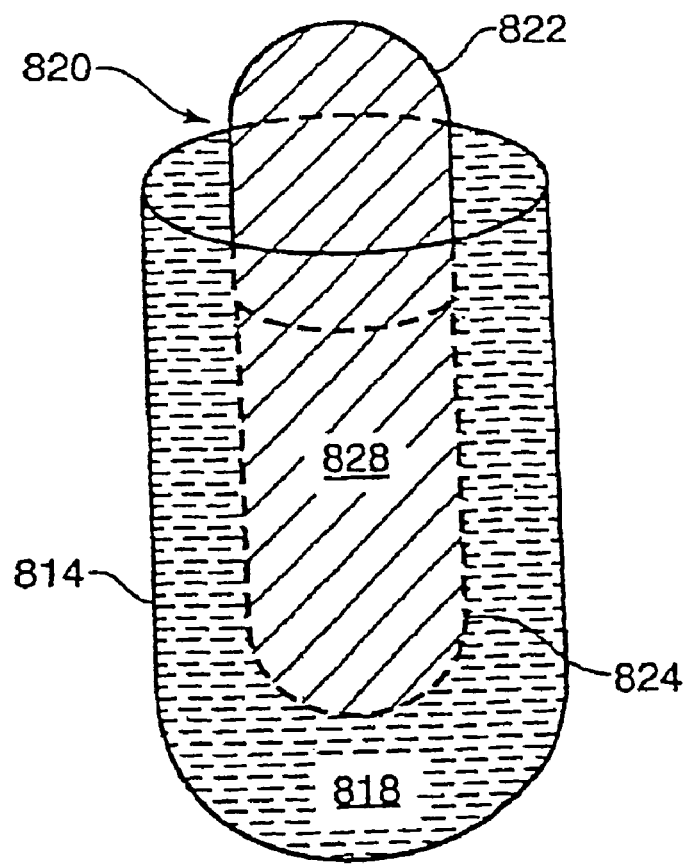
Figure 12:
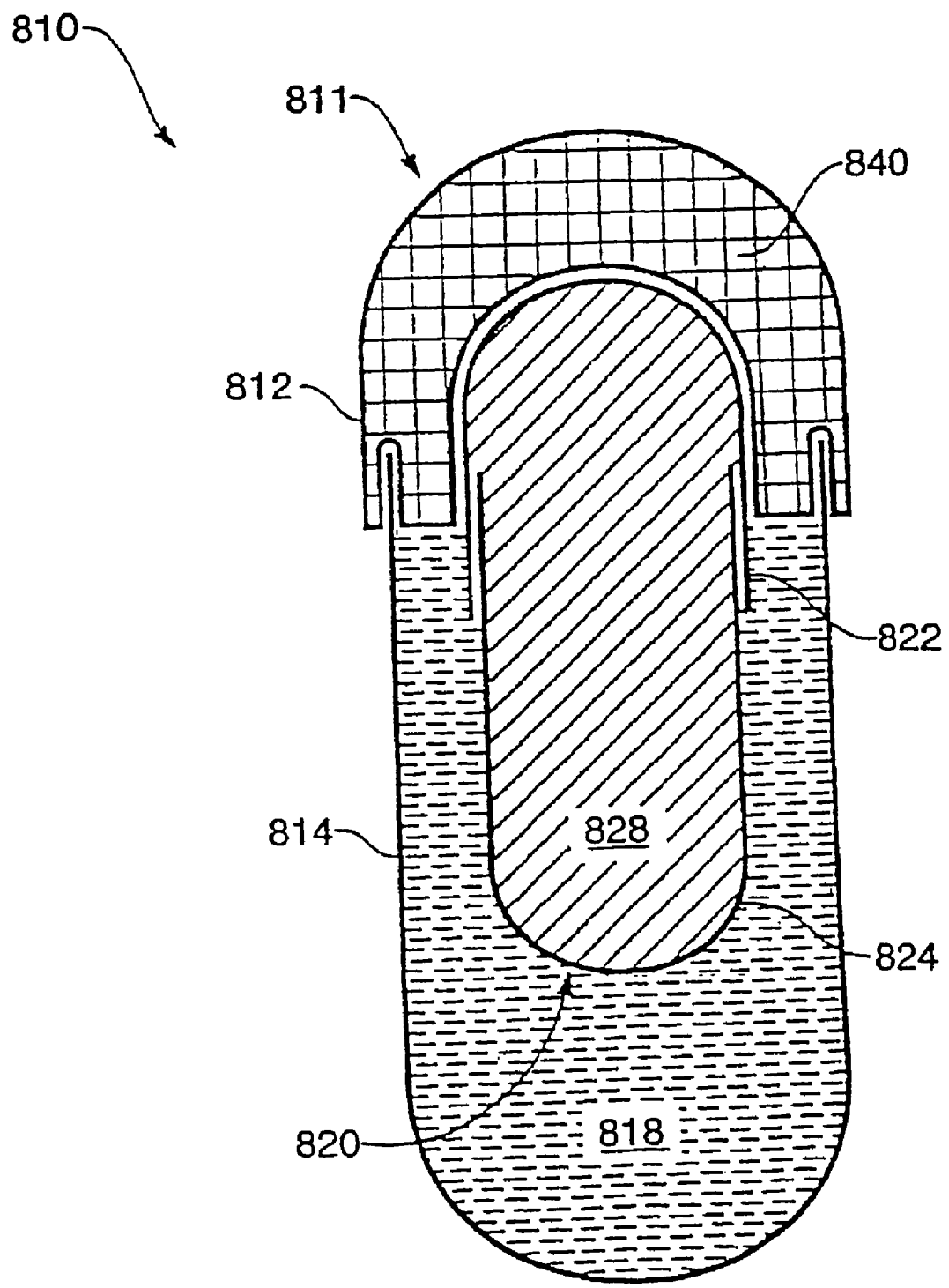
FIG. 12 is a cross-sectional view of the multi-compartment capsule shown in FIG. 11 wherein a sufficient amount of filling material is introduced into the internal periphery of the cap, thereby functioning to eliminate or significantly reduce the dead space volume in the receiving chamber of the primary capsule.

Referring now to FIGS. 11 and 12, yet another presently preferred embodiment of a multi-compartment capsule 810 of the present invention is shown comprising a secondary capsule 820 including one or more active ingredients or medicaments (e.g., pharmaeceutical, biotechnical, nutraceutical, vitamin, dietary supplement, mineral or combination thereof) within at least a portion of the internal periphery of a receiving chamber 828. The secondary capsule 820 being preferably formed having a size and shape sufficient for being selectively introduced within at least a portion of the internal periphery of a receiving chamber 818 of a primary capsule 811. Similarly, the primary capsule 811 includes one or more active ingredients or medicaments (e.g., pharmaeceutical, biotechnical, nutraceutical, vitamin, dietary supplement, mineral or combination thereof) introduced within the internal periphery of the receiving chamber 818, together with the secondary capsule 820, wherein the active ingredient(s) introduced into the primary capsule comprises a physical state (e.g., solid, liquid, gas or dispersion) which differs from the physical state of the active ingredient(s) introduced into the internal periphery of the secondary capsule 820.

In preferred structural design, the primary capsule 811 comprises a cap 812 having a general cylindrical configuration adapted to provide a sealing relationship when engaging the corresponding base 814 to form a single dosage, multi-compartment capsule 810. An amount of filling material 840 may be introduced into the internal periphery of the cap 812 to fill, either partially or completely, the inner volume of the cap, thereby reducing the dead space volume in the internal periphery of the receiving chamber 818 of the base. In this regard, the configuration of the addition of the filler material 840 relative to the internal periphery of the cap 812 generally eliminates or substantially reduces the potential dead space volume within the internal periphery of the receiving chamber 818, thus functionally negating the potential for a reaction between an air bubble and the active ingredient(s) introduced into the base 814 of the primary capsule 811.

Preferably, the filling material 840 introduced into at least a portion of the internal periphery of the cap 812 may include a hydrophilic polymer, such as gelatin. It will be readily appreciated by those skilled in the art that other filling materials may be used, such as, for example, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, (HPMC), oleoresin, polyvinylacetate-phtalate, polymerisates of acrylic or methacrylic esters, and mixtures thereof, or the like, and/or combinations thereof. In other presently preferred embodiments of the present invention, the filling material 840 may include the introduction of an inert compound, for example, nitrogen gas into at least a portion of the internal periphery of the cap 812. Based on the principals of eliminating or reducing the volume dead space in multi-compartment capsules disclosed herein, those skilled in the art will readily recognize other possible modifications and combinations which are consistent with the spirit and scope of the present invention. It is intended, therefore, that the examples provided herein be viewed as exemplary of the principles of the present invention, and not as restrictive to a particular structure or process for implementing those principles.

The filling material 840 introduced within at least a portion of the internal periphery of the cap 812 of the primary capsule 811 is generally intended to promote a binding contact with at least a portion of the cap 822 of the secondary capsule 820, thereby seating at least a portion of the secondary capsule within the cap of the primary capsule and forming a molded appearance. As appreciated, the introduction of the filling material 840 into the cap 812 of the primary capsule 811 prior to the joining and sealing process may prevent the opportunity for a reaction between an air bubble and the active medicament(s) within the receiving chamber 818 of the primary capsule, while preserving the overall rounded shape of the multi-compartment capsule 910 for ease of swallowing by a consumer.

As best illustrated in FIG. 12, one presently preferred embodiment of an encapsulation process, as defined by the structural configuration of the multi-compartment capsule 810, may include the steps of: (1) introducing one or more active ingredients or medicaments (e.g., pharmaeceutical, biotechnical, nutraceutical, vitamin; dietary supplement, mineral or combination thereof) into at least a portion of the receiving chamber 828; (2) selectively positioning the cap 822 in sealing relationship with the base 824 of the secondary capsule 820; (3) introducing one or more active ingredients or medicaments (e.g., pharmaeceutical, biotechnical, nutraceutical, vitamin, dietary supplement, mineral or combination thereof), together with the secondary capsule 820, into at least a portion of the receiving chamber 818 of the primary capsule 811; (4) introducing a filling material 840 into at least a portion of the internal periphery of the cap 812 (i.e., filling the cap); and (5) selectively positioning the cap 812 having a general conical configuration in sealing relationship with the base 814 of the primary capsule 811 to form one presently preferred embodiment of a single, dosage multi-compartment capsule 810, wherein eliminating or substantially reducing dead space volume within the internal periphery of the cap 812 and the receiving chamber 818, respectively.

A solid may be selectively introduced within at least a portion of the internal periphery of the receiving chamber 828 of the secondary capsule 820 and a liquid may be selectively introduced within at least a portion of the internal periphery of the receiving chamber 818 of the primary capsule 811. Although the ingredient(s) introduced into the receiving chamber 818 of the primary capsule 811 may be the same or different from the ingredient(s) introduced into the receiving chamber 828 of the secondary capsule 820, the active ingredient(s) in the primary capsule have a physical state (i.e., solid, liquid, gas or dispersion) that various from the physical state of the active ingredient(s) in the secondary capsule. Accordingly, those skilled in the art will readily recognize other possible modifications and adaptations relative to the contemplated variations in physical states of the active ingredient(s) selectively introduced within the receiving chambers 818, 828 of the primary and secondary capsules 811, 820, respectively, which are consistent with the spirit and scope of the present invention. It is intended, therefore, that the figures and examples provided herein be viewed as exemplary of the principles of the present invention, and not as restrictive to a particular structure or method for implementing those principles.

Figure 13:
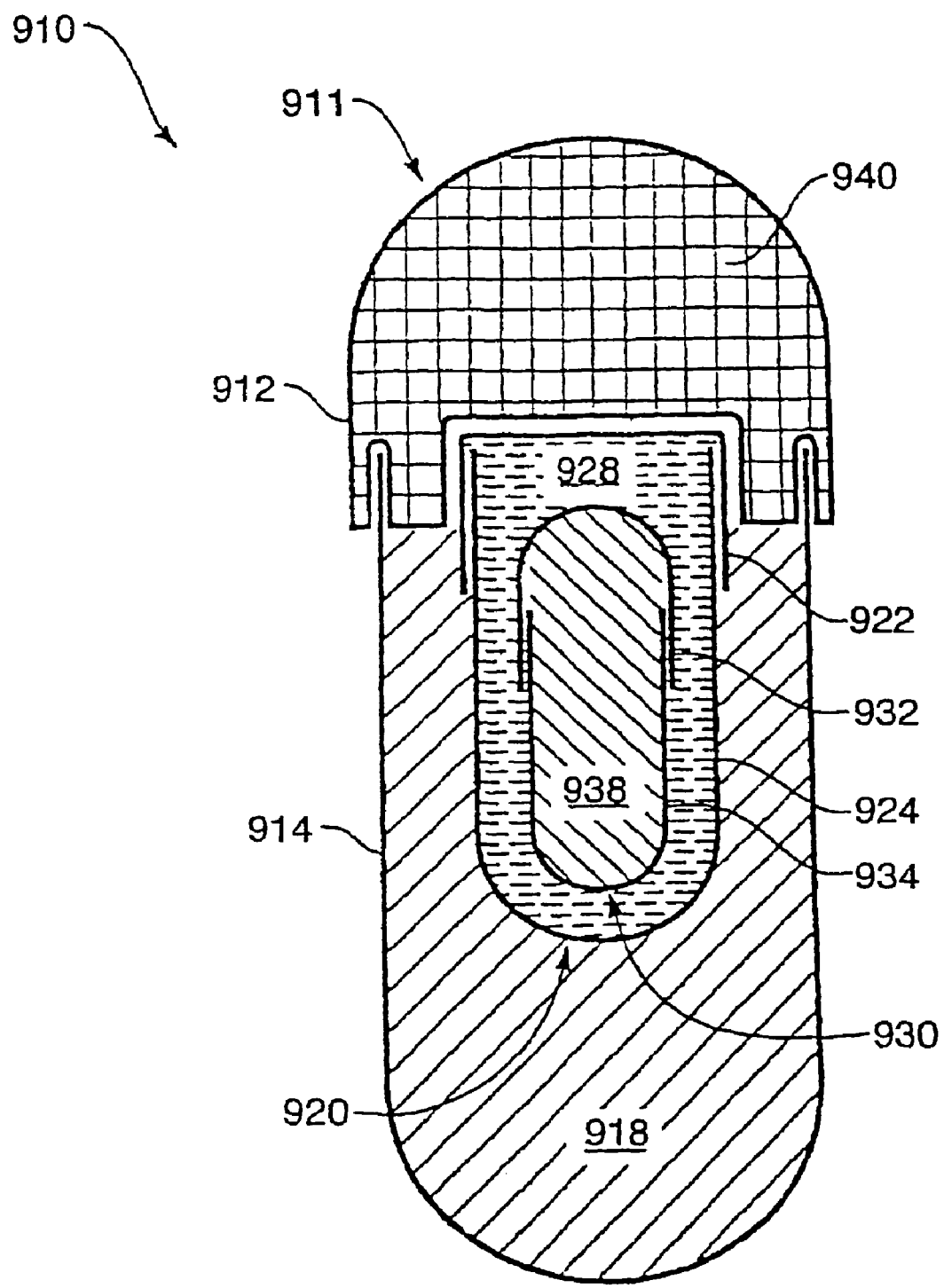
FIG. 13 is a cross-sectional view illustrating an alternate presently preferred embodiment of a multi-compartment capsule of the present invention comprising a tertiary capsule having one or more active ingredients or medicaments and having a size a shape sufficient for being introduced into at least a portion of the internal periphery of the receiving chamber of a secondary capsule having one or more active ingredients or medicaments also introduced therein, the size and shape of the secondary capsule sufficient for being selectively introduced into the internal periphery of a primary capsule having one or more active ingredients or medicaments, wherein the active ingredient(s) introduced into the primary capsule comprises a physical state (e.g., solid, liquid, gas or dispersion) which differs from the physical state of the active ingredient(s) introduced into the receiving chambers of the secondary and tertiary capsules, the primary capsule further comprising a filling material introduced into the internal periphery of the cap having a general conical configuration and adapted to provide a sealing relationship when engaging the corresponding base, thereby reducing dead space volume in the internal periphery of the receiving chamber of the base of the primary capsule.

Referring now to FIG. 13, another presently preferred embodiment of a multi-compartment capsule, generally designated at 910, is shown comprising a tertiary capsule 930 including one or more active ingredients or medicaments (e.g., pharmaeceutical, biotechnical, nutraceutical, vitamin, dietary supplement, mineral or combination thereof) within at least a portion of the internal periphery of a receiving chamber 938 and having a size and shape sufficient for being introduced into the internal periphery of a receiving chamber 928 of a secondary capsule 920. The secondary capsule 920 having one or more active ingredients or medicaments (e.g., pharmaeceutical, biotechnical, nutraceutical, vitamin, dietary supplement, mineral or combination thereof) introduced within at least a portion of the internal periphery of a receiving chamber 928, together with the tertiary capsule 930. The secondary capsule 920 preferably formed having a size and shape sufficient for being selectively introduced within at least a portion of the internal periphery of a receiving chamber 918 of a primary capsule 911. Similarly, the primary capsule 911 may include one or more active ingredients or medicaments (e.g., pharmaeceutical, biotechnical, nutraceutical, vitamin, dietary supplement, mineral or combination thereof) introduced within the internal periphery of the receiving chamber 818, together with the secondary capsule 920 which houses the tertiary capsule 930. In one presently preferred embodiment, the active ingredient(s) introduced into the secondary capsule 920 comprises a physical state (e.g., solid, liquid, gas or dispersion) which differs from the physical state of the active ingredient(s) introduced into the internal periphery of the primary capsule 911 and the internal periphery of the tertiary capsule 930.

In preferred structural design, the primary capsule 911 comprises a cap 912 having a general cylindrical configuration adapted to provide a sealing relationship when engaging the corresponding base 914 to form a single dosage, multi-compartment capsule 910. An amount of filling material 940 may be introduced into at least a portion of the internal periphery of the cap 912 to fill, either partially or completely, the inner volume of the cap, thereby reducing the dead space volume in the cap and the internal periphery of the receiving chamber 918 of the base. In this regard, the configuration of the addition of the filler material 940 relative to the internal periphery of the cap 912 may generally eliminate or substantially reduce the potential dead space volume within the internal periphery of the receiving chamber 918, thus functionally negating the potential for a reaction between an air bubble and the active ingredient(s) introduced into the base 914 of the primary capsule 911.

Preferably, the filling material 940 introduced into at least a portion of the internal periphery of the cap 912 may include a hydrophilic polymer, such as gelatin. It will be readily appreciated by those skilled in the art that other filling materials may be used, such as, for example, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methylcellulose, oleoresin, polyvinylacetatephtalate, polymerisates of acrylic or methacrylic esters, and mixtures thereof, or the like, and/or combinations thereof. In other presently preferred embodiments of the present invention, the filling material 940 may include the introduction of an inert compound, for example, nitrogen gas into at least a portion of the internal periphery of the cap 912. Based on the principals of eliminating or reducing the volume dead space in multi-compartment capsules disclosed herein, those skilled in the art will readily recognize other possible modifications and combinations which are consistent with the spirit and scope of the present invention. It is intended, therefore, that the examples provided herein be viewed as exemplary of the principles of the present invention, and not as restrictive to a particular structure or process for implementing those principles.

The filling material 940 introduced within at least a portion of the internal periphery of the cap 912 of the primary capsule 911 is generally intended to promote a binding contact with at least a portion of the cap 922 of the secondary capsule 920, thereby seating at least a portion of the secondary capsule within the cap of the primary capsule and forming a molded appearance. As appreciated, the introduction of the filling material 940 into the cap 912 of the primary capsule 911 prior to the joining and sealing process tends to prevent the opportunity for a reaction between an air bubble and the active medicament(s) within the receiving chamber 918 of the primary capsule, while preserving the overall rounded shape of the multi-compartment capsule 910 for ease of swallowing by a consumer.

As best illustrated in FIG. 13, one presently preferred embodiment of an encapsulation process, as defined by the structural configuration of the multi-compartment capsule 910, may include the steps of: (1) introducing one or more active ingredients or medicaments (e.g., pharmaeceutical, biotechnical, nutraceutical, vitamin, dietary supplement, mineral or combination thereof) into at least a portion of the receiving chamber 938 of a tertiary capsule 930; (2) selectively positioning the cap 932 in sealing relationship with the base 934 of the tertiary capsule 930; (3) introducing one or more active ingredients or medicaments (e.g., pharmaeceutical, biotechnical, nutraceutical, vitamin, dietary supplement, mineral or combination thereof), together with the tertiary capsule 930, into at least a portion of the receiving chamber 928 of the secondary capsule 920; (4) selectively positioning the cap 922 in sealing relationship with the base 924 of the secondary capsule 920; (5) introducing one or more active ingredients or medicaments (e.g., pharmaeceutical, biotechnical, nutraceutical, vitamin, dietary supplement, mineral or combination thereof), together with the secondary capsule 920, into at least a portion of the receiving chamber 918 of the primary capsule 911; (6) introducing a filling material 940 into at least a portion of the internal periphery of the cap 912 (i.e., preferably filling the cap); and (7) selectively positioning the cap 912 having a general conical configuration in seating relationship with at least a portion of the secondary capsule 920 and sealing the base 914 of the primary capsule 911 to form one presently preferred embodiment of a single, dosage multi-compartment capsule 910, wherein eliminating or substantially reducing dead space volume within the internal periphery of the cap 912 and the receiving chamber 918, respectively.

A solid may be introduced within at least a portion of the internal periphery of the receiving chamber 938 of the tertiary capsule 930, a liquid may be introduced into at least a portion of the internal periphery of the secondary capsule 920 and a solid may be selectively introduced within at least a portion of the internal periphery of the receiving chamber 918 of the primary capsule 911. Although the ingredient(s) introduced into the receiving chambers 918, 928, 938 of the primary, secondary and tertiary capsules 911, 920, 930, respectively, may be the same or different from the ingredient(s) introduced into the other receiving chambers, the active ingredient(s) in at least two of the receiving chambers 918, 928, 938 have different physical states (i.e., solid, liquid, gas or dispersion). Those skilled in the art will readily recognize other possible modifications and adaptations relative to the contemplated variations in physical states of the active ingredient(s) selectively introduced within the receiving chambers 918, 928, 938 of the primary, secondary and tertiary capsules 911, 920, 930, respectively, which are consistent with the spirit and scope of the present invention. It is intended, therefore, that the figures and examples provided herein be viewed as exemplary of the principles of the present invention, and not as restrictive to a particular structure or method for implementing those principles.

Generally referring to FIGS. 1-13, the component parts of the presently preferred embodiments of the multi-compartment capsules (i.e., capsular base, corresponding cap and dividing walls) of the present invention may comprise a hydrophilic polymer, such as gelatin (marine or animal based product). Other suitable materials forming the capsules may include starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose (HPMC), oleoresins, polyvinylacetate-phtalate, polymerisates of acrylic or methacrylic esters, and mixtures thereof, or the like, and/or combinations thereof. The material comprising the capsular components may further include between about 0% to 40% of pharmaeceutically acceptable plasticizers based upon the weight of the hydrophilic polymer. Plasticizers that may be employed include, for example and not by way of limitation, polyethylene glycol, glycerol, sorbitol, dioctyl-sodium sulfosuccinate, triethyl citrate, tributyl citrate, 1,2-propyleneglycol, mono-acetates, di-acetates, or triacetates of glycerol, mixtures thereof, or the like, and/or combinations thereof. As appreciated, plasticizers may also be used in the development of a soft elastic shell, often referred to as a soft gelatin capsule or "soft gel" capsule, for a primary capsule, a secondary capsule and/or a tertiary capsule.

The capsular shell material may contain pharmaeceutically acceptable lubricants in the range of about 0% to 10%, based upon the weight of the hydrophilic polymer. Lubricants that may be used include, for example and not by way of limitation, aluminum stearate, calcium stearate, magnesium stearate, tin stearate, talc, sodium lauryl sulfate, lecithins, mineral oils, stearic acid, silicones, mixtures thereof, or the like, and/or combinations thereof. One presently preferred embodiment of the multi-compartmental capsules of the present invention (e.g., primary capsule, secondary capsule, tertiary capsule, etc.) may include, for example, LICAPS® capsules (for poorly soluble compounds), VCAPS™ capsules (made from cellulosic raw materials), CONI-SNAP® capsules and PRESS-FIT® capsules which are all presently manufactured by Capsugel, a subsidiary of Pfizer, Inc.

In one presently preferred embodiment of an encapsulation process, the primary capsule may be kept under conditions of low humidity within a filling machine during the contemplated steps of rectifying and assembling. In certain embodiments, the primary capsule may contain moisture content in the range of approximately 0% to 6% of the total weight. Similarly, a secondary capsule, a tertiary capsule, etc. may be processed in the same manner as the primary capsule relative to conditions of low humidity during the steps of rectifying and assembling. As contemplated herein, a moisture content of approximately 0% to 3% by weight is preferable. However, capsules having a higher moisture content than those stated herein are certainly not outside the spirit and scope of the present invention.

As illustrated in FIGS. 1-9 and 11-13, the shape of the base and corresponding cap of the capsules (e.g., primary, secondary, tertiary, etc.) of the presently preferred embodiments of the multi-compartment capsules are configured having a general cylindrical shape which defines a diameter and length sufficient for the introduction of an internal smaller capsule or one or more dividing walls along the length of the capsular base. It is apparent that other geometrical configurations of the cap are likewise suitable and contemplated herein, such as the general U-shaped configuration of the cap shown in FIG. 10. It is intended, therefore, that the examples provided herein be viewed as exemplary of the principles of the present invention, and not as restrictive to any particular structure or configuration for implementing those principles.

In one presently preferred embodiment, the clearance between the primary capsule and the secondary capsule introduced within the internal periphery of the primary capsule is preferably greater than +0.2 mm. The clearance between the outer capsular walls of the secondary capsule and the inner capsular walls of the primary capsule (or the tertiary capsule and the secondary capsule) may be in the range of about 0 mm to 0.5 mm, whereas the outer capsular walls of the secondary capsule or tertiary capsule may be in actual contact with the inner capsular walls of the primary capsule or secondary capsule, respectively. As appreciated, in an effort to structural facilitate independent receiving chambers on opposing sides of a dividing wall introduced within the internal periphery of a base of a capsule, the perimeter of the dividing wall preferably engages the inner capsular walls of the capsule to provide a sealing relationship therebetween.

As further contemplated herein, the inner capsular walls of a primary capsule may be treated with an adhesive sufficient to improve engagement between the primary capsule and the outer capsular walls of a secondary capsule. A suitable technique to apply an adhesive may be by way of spraying the same on the shells and capsules immediately before assembling the same. Suitable adhesives that may be used may include, for example, tackidex, an aqueous gelatin solution, or the like.

The primary, secondary or tertiary capsules, in accordance with the present invention, may be formed having the same or different colors. Moreover, the base and corresponding cap of a single capsule may be formed having different colors in an effort to enhance the aesthetics of the capsule to the consumer. In one presently preferred embodiment of a multi-compartment capsule of the present invention, the dosage may be banded, sealed or easily dividable in a contact area of the primary and secondary capsules or the sealing band may be color-coded to assist in branding, if desired.

It is further contemplated herein that a multi-compartment capsule of the present invention may comprise component parts of the capsule having various time-release coatings to facilitate the release and ultimately the absorption of those active ingredients introduced into the different receiving chambers of the multi-compartment capsule to release at different release rates. In particular, a primary capsule may be formed having a conventional time-release coating that dissolves and releases the active ingredient(s) contained therein before the timed-release of the active ingredient(s) contained within a secondary capsule. Likewise, the dividing walls disposed within the internal periphery of the base of a capsule may be formed having conventional time-release coatings that dissolve and release the active ingredients within each receiving chamber defined by the dividing walls at different rates, thereby delivering the active ingredients or medicaments contained within a multi-compartment capsule at different rates. Certain active ingredients or medicaments may, therefore, be delivered at a selected interval, while other ingredients may be released at a later interval. In this way, the novel design of the multi-compartment capsules of the present invention may facilitate precision delivery of active ingredients to targeted areas of the consumer.

The disclosure of secondary and tertiary capsules may be replaced with other forms of microencapsulation. Microencapsulation, as previously described, refers to the process whereby minute parcels of a solid, liquid, gas or dispersion, introduced into one or more of the receiving chambers as active ingredient(s), are film-coated with a secondary material in order to shield the active ingredient from its surrounding environment. Microcapsules may measure from microns to several millimeters, whereas the main purpose being to facilitate the release of the active ingredients at different release rates.

The incorporation of time-release coatings to varying the release rates of the active ingredients of a multi-compartment capsule may be used to target key time intervals or events when the body may be most able to utilize the active ingredients. In one presently preferred embodiment of the present invention, all of the active ingredients may be microencapsulated. In alternate presently preferred embodiments, only selected ingredients may be microencapsulated for delayed release, while other ingredients may be provided for immediate absorption. Thus, the incorporation of time-release coatings in the encapsulation process when forming a multi-compartment capsule may be specifically designed to fit the needs and desires of numerous different users having similar conditions that are being targeted for treatment.

As contemplated herein, the physical states of active ingredients are characterized into one of four different states (e.g., solid, liquid, gas or dispersion). These four different states are sometimes referred to as "phases" (i.e., solid phase, liquid phase, gas phase or dispersion phase). For purposes of the present invention, the term "solid" is defined as including, by way of example only and not by way of limitation, pills, tablets, capsules (including both hard and soft elastic), powders, granulation, flakes, troches (lozenges and pastilles), suppositories and semi-solid pastes, ointments, emulsions or creams. The term "liquid" is defined as including, by way of example only and not by way of limitation, solutions, spirits, elixirs, sprays, syrups or fluid extracts. The term "dispersion" is defined as including, by way of example only and not by way of limitation, aerosols (liquid or solid in gas), suspensions (solid in liquid), emulsions (liquid in liquid), foams (gas in liquid), solid foams (solid in gas) or gels (liquid or solid in solid).

The active ingredients or medicaments introduced into the receiving chambers of the multi-compartment capsules of the present invention preferably comprise a pharmaeceutical, biotechnical, nutraceutical, vitamin, dietary supplement, mineral or combination thereof For purposes of the present invention, the term "pharmaeceutical" is defined as any substance that affects the structure or functioning of a living organism. Pharmaeceuticals, sometimes referred to as "drugs" are widely used for the prevention, diagnosis and treatment of diseases and for the relief of symptoms. The term "biotechnical" is defined as any substance that is derived from a biotechnology process. Biotechnology, sometimes shortened to "biotech", is the development of techniques and methods (e.g., genetic engineering, protein engineering, genomics, proteomics, monoclonal antibody production, polymerase chain reaction, transgenics and the like) for the application of biological processes to the production of materials of use in medicine, foods, nutrition and industry. The term "nutraceutical" is defined as any substance that is a food of a part of a food and provides medical or health benefits, including the prevention and treatment of disease. The term "vitamin" is defined as any of various organic substances or compounds that are essential for the normal processes of growth and maintenance (e.g., essential for energy transformation and regulation of metabolism) of the body which are present in natural foodstuffs or sometimes produced within the body. The term "dietary supplement" is defined as any product (other than tobacco) intended to supplement the diet that bears or contains one or more of the following dietary ingredients: (A) a vitamin; (B) a mineral; (C) an herb or other botanical; (D) an amino acid; (E) a dietary substance for supplementing the diet by increasing the total dietary intake; or (F) a concentrate, metabolite, constituent, extract or combination of any ingredient described in (A), (B), (C), (D), or (E) hereinabove. If desired, excipients may also be introduced into one or more of the receiving chambers of the multi-compartment capsules of the present invention in addition to the active ingredient(s). For example, in some cases involving medicaments with poor water solubility, it may be desirous to stabilize the liquids, solids or dispersions using a lipid, lipoid, lecithin, ghee or the like. Still further by example, in some cases involving active ingredients or medicaments with poor bioavailability, bioequivalence, or other undesirous pharmaeceutical properties (e.g., poor water solubility, pH lability, physical incompatibility, chemical incompatibility, macromolecular size and the like) such as proteins (e.g., hormones, erythropoeitins, colony stimulating factors, interferons, interleukins, plasminogen activators, monoclonal antibodies, vaccines, plant proteins, such as soy and other therapeutic proteins) or other non-polar or weak-polar materials, it may be desirous to complement the active ingredient or medicament in liquid, solid or dispersion form using a fat, lipid, lipoid, lecithin, ghee, polymers, viral and bacterial vectors and the like.

It may be demonstrated that as medical and pharmacy knowledge has continued to expand exponentially, new medicaments, new classes of medicaments and new delivery technologies are becoming available for use in animals and humans who experience particular medical diseases, illnesses or conditions. A disease, illness, or condition may affect one or more organ systems in an animal or human. Organ systems may include, for example: (1) autonomic, (2) cardiovascular, (3) neurological, (4) gastro-intestinal, (5) respiratory, (6) renal system, (7) psychiatric, (8) endocrine, (9) gynecologic, (10) urologic, (11) immunologic, (12) bone and joint systems, (13) ear, nose, and throat, (14) dermatologic, (15) hematologic, (16) infectious defense and (17) nutrition and metabolism. In an animal or human who may be suffering from one disease, illness or condition, it is common to also be suffering from a disease, illness or condition affecting one or more of the other organ system(s). These concomitant diseases, illnesses or conditions occurring within a single animal or human are often labeled as "co-morbidities," a term often shortened and referred to as "co-morbid."

New medicaments and delivery technologies are providing patients and their health care practitioners with unprecedented therapeutic options in managing diseases, illnesses and conditions. In spite of this sophistication, there has been no effort to develop new methods of using fixed combinations of medicaments for therapy of co-morbid diseases, illnesses or conditions. Moreover, there has been no effort to develop new methods of using fixed combinations of medicaments for management of a single disease, illness or condition affecting one or more organ system(s). The aforementioned fixed combinations may include a plurality of medicaments, which may be newly discovered and developed, or have been known for sometime or some combination of medicaments thereof. In any regard, said fixed combinations have not previously been contemplated in the art.

The following examples will illustrate the invention in further detail. It will be readily understood that the various active ingredients or medicaments that may be introduced into the receiving chambers of the multi-compartment capsules of the present invention, as generally described and illustrated in the Examples herein, are to be viewed as exemplary of the principles of the present invention, and not as restrictive to a particular structure or process for implementing those principles. Thus, the following more detailed description of the presently preferred embodiments of the methods, formulations, and compositions of the present invention, as represented in Examples I-XIV below, is not intended to limit the scope of the invention, as claimed, but is merely representative of presently preferred embodiments of the invention.

Example I

Glucosamine/Chondroitin (Solid) & Vitamin E (Liquid)

As appreciated by those skilled in the art, arthritis is an inflammatory condition typically affecting the synovia membranes and cartilage of joints. It has been estimated that as many as one in three persons may experience symptoms associated with arthritis during their lifetime.

In addition to arthritis, various other chronic, debilitating conditions may afflict the aged. Many of these conditions result from the natural process of aging in humans. The natural aging process is partially due to the accumulation and effects of toxic free-radical chemicals. Free-radicals result from several homeostatic biochemical processes. It is, accordingly, desirable to develop nutraceutical or dietary supplement products which may alleviate multiple chronic, debilitating conditions. It is also desirable to package and administer such products in the most economic and convenient possible fashion.

The administration of glucosamine, a naturally occurring substance in mucopoly-saccharides, mucoproteins and chitin, is believed to promote the production of cartilage components and the repair of damaged cartilage. Clinical findings support that fibroblast cells increased production of mucopolysaccharide and collagen synthesis when glucosamine was added.

Chondroitin sulfates are large polymers of glycosaminoglycans, primarily D-glucuronic acid and D-acetylgalactosamine, and disaccharides and may be derived from the cartilage of bovine trachea. The administration of chondroitin sulfate has been shown to promote the formation of new cartilage matrix. In particular, chondroitin stimulates the metabolism of chondrocyte cells and the production of collagen and proteoglycan.

Vitamin E, also known as alpha-tocopherol, is a well-known scavenger of free-radicals in the body. Free-radical scavengers are sometimes referred to as anti-oxidants. This scavenging process is important for detoxifying the body of chemicals which are known to promote apoptosis, or programmed cell death. Apoptosis is a scientific description of cellular destruction. Although vitamin E is a popular anti-oxidant, it is poorly soluble in water and thus can be administered only as a liquid-oil formulation or in an oil formulation enclosed in a soft elastic capsule.

In one presently preferred embodiment of the present invention, therapeutically effective amounts of glucosamine, chondroitin, and vitamin E (active ingredients) may be introduced into receiving chambers of a multi-compartment capsule wherein at least two of the active ingredients have physical states (e.g., solid, liquid, gas or dispersion) that differ. Consistent with the foregoing, multi-compartment, multi-phase capsules and encapsulation technology are herein contemplated to produce a delivery vehicle for delivering anti-arthritic and anti-oxidant compounds to the body in a single dosage. A capsular format of the present invention may include the following composition:

| Primary Capsule: | |
|---|---|
| Glucosamine HCl [500-2000 mg/day] | 500 mg |
| Chondroitin sulfate [400-1600 mg/day] | 400 mg |
| Secondary Capsule: | |
| Vitamin E [200-400 IU/day] | 200 IU |

The incorporation of time-release coatings to varying the release rates of the active ingredients (e.g., glucosamine HCl/chondroitin sulfate and vitamin E) in the primary and secondary capsules, respectively, of the multi-compartment capsule may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment.

A therapeutically effective amount of glucosamine HCl/chondroitin sulfate may be introduced into at least a portion of the internal periphery of the receiving chambers of a primary capsule in the form of a solid and a therapeutically effective amount of vitamin E may be introduced into at least a portion of a secondary capsule in the form of a liquid, if desired. Since the encapsulation process and multi-compartment, multi-phase capsule of the present invention are configured to apply to an anticipated treatment regime or medicinal design of a single dosage capsule, it will be readily appreciated that the introduction of one or more active ingredients into the receiving chambers of the primary and secondary capsules, respectively, is anticipated such that the various ingredients may be introduced in different receiving chambers to accommodate different treatment modalities. For example, a multi-compartment capsule may be formulated having glucosamine HCl and chondroitin sulfate introduced into the receiving chambers of the secondary capsule and vitamin E may be introduced into the receiving chamber of the primary capsule. It is intended, therefore, that the examples provided herein be viewed as exemplary of the principles of the present invention, and not as restrictive to a particular structure or method for implementing those principles.

Example II

S-adenosylmethionine (SAMe) (solid) & Vitamin E (liquid)

S-adenosylmethionine (SAMe), may be derived from two materials: methionine, a sulfur-containing amino acid, and adenosine triphosphate (ATP), the body's main energy compound. SAMe was originally developed around 1950 as an antidepressant. Over the years, it has also been found that SAMe may assist in alleviating arthritic symptoms, assist in the manufacture of melatonin, which is needed to regulate sleep, help protect DNA from harmful mutations and prevent certain types of nerve damage.

As noted above, vitamin E is a popular anti-oxidant, but it is poorly soluble in water and therefore can be administered only as a liquid-oil formulation. Vitamin E is typically measured in international units (IU) of alpha tocopherol.

In one presently preferred embodiment of the present invention, therapeutically effective amounts of SAMe and vitamin E (active ingredients) may be introduced into receiving chambers of a multi-compartment capsule wherein SAMe comprises a physical state (e.g., solid, liquid, gas or dispersion) different from the physical state of vitamin E. As shown in FIGS. 3 and 4, a therapeutically effective amount of SAMe may be introduced into receiving chamber 218a and a therapeutically effective amount of vitamin E may be introduced into receiving chamber 218b of a multi-compartment capsule 210 of the present invention. Consistent with the foregoing, multi-compartment, multi-phase capsules and encapsulation technology are herein contemplated to produce a delivery vehicle for delivering mood enhancing, anti-arthritic and anti-oxidant compounds to the body in a single dosage. A capsular format of the present invention may include the following composition:

| Receiving Chamber (218a): | |
| --- | --- |
| S-adenosylmethionine [200-1600 mg/day] | 1000 mg |
| Receiving Chamber (218b): | |
| Vitamin E [200-400 IU/day] | 200 IU |

The incorporation of time-release coatings to varying the release rates of the active ingredients (e.g., SAMe and vitamin E) of the multi-compartment capsule 210 may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment.

According to one presently preferred embodiment of the present invention, a therapeutically effective amount of SAMe may be introduced into at least a portion of the receiving chamber 218a in the form of a solid and a therapeutically effective amount of vitamin E may be introduced into at least a portion of the receiving chamber 218b of the primary capsule 211 in the form of a liquid.

In an alternative presently preferred embodiment of the present invention, therapeutically effective amounts of SAMe and vitamin E (active ingredients) may be introduced into receiving chambers of a multi-compartment capsule wherein SAMe comprises a physical state (e.g., solid, liquid, gas or dispersion) different from the physical state of vitamin E. As shown in FIG. 2, a therapeutically effective amount of SAMe, in the form of a solid, may be introduced into receiving chamber 118 and 138 and a therapeutically effective amount of vitamin E, in the form of a liquid, may be introduced into receiving chamber 128 of a multi-compartment capsule 110 of the present invention. The material forming the primary capsule shell 111 may be formulated in a manner allowing for immediate dissolution and release of the of the contents of receiving chamber 118. The material forming the secondary capsule shell 120 may be formulated in a manner allowing for either an immediate dissolution or a time-delayed dissolution and release of the contents of receiving chamber 128. The material forming the tertiary capsule shell 138 may be formulated in a manner allowing for time-delayed dissolution and release of the contents of receiving chamber 138. In this presently preferred embodiment of the present invention, a total daily dosage of SAMe may be delivered as two separate dosages within a single oral dosage form. One presently preferred embodiment of the present invention thus makes for a more convenient dosage form.

Since the encapsulation process and multi-compartment, multi-phase capsule of the present invention are configured to apply to an anticipated treatment regime or medicinal design of a single dosage capsule, it will be readily appreciated that the introduction of one or more active ingredients into receiving chambers defined within a capsule is anticipated such that the various ingredients may be introduced in different receiving chambers to accommodate different treatment modalities. It is intended, therefore, that the examples provided herein be viewed as exemplary of the principles of the present invention, and not as restrictive to a particular structure or method for implementing those principles.

Example III

Curcumin, Holy Basil, Zinc (Solid) & Fish Oil (Omega 3 Fatty Acids DHA & EPA-Liquid)

Curcumin belongs to a class of compounds derived from the turmeric root and is a yellow-orange volatile oil. It is believed that curcumin has an inhibitory effect on carcinogenesis, which is the evolution of a normal cell into a cancerous cell. There is clinical evidence to suggest curcumin may help to prevent stomach, colon, oral, esophageal, breast and skin cancers. Additional studies have been conducted to show that curcumin may be helpful in balancing cholesterol levels, protecting against ulcers by inhibition of gastric acid secretion and protection of gastric mucosal tissue, and anti-inflammatory actions. In one clinical study, curcumin was found to be as effective as non-steroidal anti-inflammatory drugs in the treatment of arthritis and post-operative pain.

The administration of Holy Basil (*Ocimum sanctum*) has been shown to have an effect on promoting peripherally mediated analgesic effects. This action allows a broad range of therapeutic effects, including, anti-inflammatory, hypoglycemia, analgesic, anti-ulcer and anti-septic properties.

As known, zinc is a mineral that occurs in animal and plant tissues and is an important co-factor for various enzyme reactions in the body, as well as being helpful for the reproduction system, and for the manufacture of body proteins. Zinc is also an antioxidant nutrient, similar to vitamin E. There is clinical data that suggests that zinc may be important to the prostate and other reproductive organs in the body, may help in the contractility of muscles, help stabilize blood, help maintain the body's alkaline balance and aid in the digestion and metabolism of phosphorus.

Over several decades considerable evidence has been collected to suggest that fish and fish oils are beneficial to the heart, mental health and in reducing cancer risk. The "active" components of fish oils are eicosapentaenoic acid (EPA), a polyunsaturated fatty acid with a 20 carbon chain, and docosahexaenoic acid (DHA), a polyunsaturated fatty acid with a 22 carbon chain. Both active components are members of the omega-3 group of essential fatty acids and are found exclusively in marine animals. The best sources for EPA and DHA may be fatty fish such as herring, sardines, salmon and fresh tuna.

The recommended daily intake of EPA plus DHA is between 650 to 1000 mg/day. Clinical trials have used anywhere from 1 g/day to 10 g/day, but little additional benefit has been observed at levels above 5 g/day of EPA and DHA combined. The onset of beneficial effects is variable. Effects on cholesterol may occur in just a few weeks, but it may take there (3) months or longer to see effects in degenerative diseases, such as arthritis.

In one presently preferred embodiment of the present invention, therapeutically effective amounts of curcumin, Holy Basil, zinc and fish oil (active ingredients) may be introduced into receiving chambers of a multi-compartment capsule wherein curcumin, Holy Basil and zinc comprise a physical state (e.g., solid, liquid, gas or dispersion) different from the physical state of the fish oil. As shown in FIG. 2, a therapeutically effective amount of curcumin may be introduced into receiving chamber 138 of a tertiary capsule 130, a therapeutically effective amount of Holy Basil and zinc may be introduced into receiving chamber 128 of a secondary capsule and a therapeutically effective amount of fish oil may be introduced into receiving chamber 118 of a primary capsule 111 of a multi-compartment capsule 110 of the present invention. Consistent with the foregoing, multi-compartment, multi-phase capsules and encapsulation technology are herein contemplated to produce a delivery vehicle for delivering anti-neoplastic, anti-inflammatory, analgesic and anti-oxidant compounds to the body in a single dosage. A capsular format of the present invention may include the following composition:

| Tertiary Capsule (130): | |
|---|---|
| Curcumin | 400 mg |
| [1200-1800 mg/day; 400 mg three times daily] | |
| Secondary Capsule (120): | |
| Holy Basil | 2.5 gms |
| [2.5 grams fresh dried leaf powder/day] | |
| Zinc | 15 mg |
| [4-15 mg/day] | |
| Primary Capsule (111): | |
| Fish oil | 1000 mg |
| (Omega 3 fatty acids - DHA & EPA) | |
| [650-1000 mg/day] | |

The incorporation of time-release coatings to varying the release rates of the active ingredients (e.g., curcumin, Holy Basil, Zinc and fish oil) in the primary, secondary and tertiary capsules 111, 120, 130 of one presently preferred embodiment of a multi-compartment capsule 110 may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment.

As contemplated herein, a therapeutically effective amount of curcumin may be introduced into at least a portion of the receiving chamber 138 of the tertiary capsule 130 in the form of a solid, a therapeutically effective amount of Holy Basil and zinc may be introduced into at least a portion of the receiving chamber 128 of the secondary capsule 120 in the form of a solid and a therapeutically effective amount of fish oil may be introduced into at least a portion of the primary capsule 111 in the form of a liquid. Since the encapsulation process and multi-compartment, multi-phase capsule of the present invention are configured to apply to an anticipated treatment regime or medicinal design of a single dosage capsule, it will be readily appreciated that the introduction of one or more active ingredients into the receiving chambers of the primary and secondary capsules, respectively, is anticipated such that the various ingredients may be introduced in different receiving chambers to accommodate different treatment modalities. It is intended, therefore, that the examples provided herein be viewed as exemplary of the principles of the present invention, and not as restrictive to a particular structure or method for implementing those principles.

Example IV

Vitamin C (Solid) & Vitamin E (Liquid)

It is believed that vitamin C plays an important role as a component of enzymes involved in the synthesis of collagen and carnitine. A vital role of vitamin C, however, is believed to be that of the primary, water-soluble antioxidant in the human body. A daily intake of 60-1000 mg of vitamin C may be adequate for preventive purposes, but far larger quantities may be required to have an effect on halting or reversing cancer and heart disease.

As noted above, vitamin E is a popular anti-oxidant, but it is poorly soluble in water and therefore can be administered only as a liquid-oil formulation.

In one presently preferred embodiment of the present invention, therapeutically effective amounts of vitamin C and vitamin E (active ingredients) may be introduced into receiving chambers of a multi-compartment capsule wherein vitamin C comprises a physical state (e.g., solid, liquid, gas or dispersion) different from the physical state of vitamin E. Consistent with the foregoing, multi-compartment, multi-phase capsules and encapsulation technology are contemplated herein to produce a delivery vehicle for delivering anti-oxidant compounds to the body in a single dosage. A capsular format of the present invention may include the following composition:

| Primary Capsule: | |
|---|---|
| Vitamin C | 500 mg |
| [60-1000 mg/day] | |
| Secondary Capsule: | |
| Vitamin E | 200 IU |
| [200-400 IU/day] | |

The incorporation of time-release coatings to varying the release rates of the active ingredients (e.g., vitamin C and vitamin E) in different receiving chambers of a multi-compartment capsule may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment and is contemplated herein.

A therapeutically effective amount of vitamin C may be introduced into at least a portion of a first receiving chamber in the form of a solid and a therapeutically effective amount of vitamin E may be introduced into at least a portion of a second receiving chamber in the form of a liquid. Since the encapsulation process and multi-compartment, multi-phase capsule of the present invention are configured to apply to an anticipated treatment regime or medicinal design of a single dosage capsule, it will be readily appreciated that the introduction of one or more active ingredients into the receiving chambers of the primary and secondary capsules, respectively, is anticipated such that the various ingredients may be introduced in different receiving chambers to accommodate different treatment modalities. It is intended, therefore, that the examples provided herein be viewed as exemplary of the principles of the present invention, and not as restrictive to a particular structure or method for implementing those principles.

Example V

Selenium/Vitamin C (Solid) & Vitamin E/Beta-Carotene/Fish Oil (Omega 3 Fatty Acids DHA & EPA) (Liquid)

Selenium is an essential trace mineral in the human body and an important part of antioxidant enzymes that protect cells against the effects of free radicals that are produced during normal oxygen metabolism. As readily known in the art, the body has developed defenses, such as antioxidants, to assist in controlling levels of free radicals which can cause damage to cells and contribute to the development of some chronic diseases. It is also believed that Selenium is essential for normal functioning of the immune system and thyroid gland. The recommended dietary allowance for selenium is 55 mcg/day.

As noted above, it is believed that vitamin C plays an important role as a component of enzymes involved in the synthesis of collagen and carnitine and a vital role as a water-soluble antioxidant in the human body. Vitamin E is another important anti-oxidant.

Beta-carotene is a substance found in plants that the body converts into vitamin A. It is believed that beta-carotene acts as an antioxidant and an immune system booster. There is no RDA for beta-carotene. The most common beta-carotene supplement intake is about 25,000 IU (15 mg) per day, however supplementation with as much as 100,000 IU (60 mg) per day has been reported.

It has been suggested that fish and fish oils are beneficial to the heart, mental health and in reducing cancer risk. The recommended daily intake of EPA plus DHA (the active components of fish oil) is between 650 to 1000 mg/day. Clinical trials have used anywhere from 1 g/day to 10 g/day, but little additional benefit has been observed at levels above 5 g/day of EPA and DHA combined.

In one presently preferred embodiment of the present invention, therapeutically effective amounts of selenium, vitamin C, beta-carotene, vitamin E and fish oil (active ingredients) may be introduced into receiving chambers of a multi-compartment capsule wherein selenium and vitamin C comprise a physical state (e.g., solid, liquid, gas or dispersion) different from the physical state of vitamin E, beta-carotene and fish oil (omega 3 fatty acids DHA & EPA). Specifically, a therapeutically effective amount of selenium and vitamin C may be introduced into one or more receiving chambers of a primary capsule and a therapeutically effective amount of vitamin E, beta-carotene and fish oil (omega 3 fatty acids DHA & EPA) may be introduced into one or more receiving chambers of a secondary capsule to form a multi-compartment capsule of the present invention. Consistent with the foregoing, multi-compartment, multi-phase capsules and encapsulation technology are herein contemplated to produce a delivery vehicle for delivering anti-oxidant compounds to the body in a single dosage. A capsular format of the present invention may include the following composition:

| Primary Capsule: | |
|---|---|
| Selenium [50-100 mcg/day] | 50 mcg |
| Vitamin C [60-1000 mg/day] | 500 mg |
| Secondary Capsule: | |
| Beta-carotene [30-300 mg/day] | 50 mg |
| Vitamin E [200-400 IU/day] | 200 IU |
| Fish oil (Omega 3 fatty acids - DHA & EPA) [650-1000 mg/day] | 1000 mg |

The incorporation of time-release coatings to varying the release rates of the active ingredients (e.g., selenium, vitamin C, vitamin E, beta carotene and fish oil) in different receiving chambers of a multi-compartment capsule may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment and is contemplated herein.

A therapeutically effective amount of selenium and vitamin C may be introduced into one or more receiving chambers of a primary capsule in solid form and a therapeutically effective amount of vitamin E, beta carotene and fish oil may be introduced into one or more receiving chambers of a secondary capsule in the form of a liquid. Since the encapsulation process and multi-compartment, multi-phase capsule of the present invention are configured to apply to an anticipated treatment regime or medicinal design of a single dosage capsule, it will be readily appreciated that the introduction of one or more active ingredients into the receiving chambers of the primary and secondary capsules, respectively, is anticipated such that the various ingredients may be introduced in different receiving chambers to accommodate different treatment modalities. It is intended, therefore, that the examples provided herein be viewed as exemplary of the principles of the present invention, and not as restrictive to a particular structure or method for implementing those principles.

Example VI

Fluoxetine (Solid), S-Adenosylmethionine (SAMe) (Solid) & Vitamin E (Liquid)

As appreciated by those skilled in the art, depression is a mental state characterized by excessive sadness. Depression is one of several forms of mood disorders. Activity in those affected with depression may be agitated and restless or slow and retarded. Those affected may also show pessimistic or despairing behavior and may have disturbances in sleep, appetite and concentration. Depression is often a co-morbid condition with other chronic disease states involving the neurological system, cardiovascular system, respiratory system, endocrine system, musculoskeletal system, immune system, genitourinary system and the like. This list is should not be considered exclusive.

Administration of Fluoxetine is known by those of skill in the art to alleviate the signs and symptoms of depression. Fluoxetine belongs to a class of compounds which are given the functional name: selective serotonin re-uptake inhibitors (SSRI's). This class may include, for example: fluoxetine (PROZAC®), sertraline (ZOLOFT®), paroxetine (PAXIL®), fluvoxamine (LUVOX®), citalopram (CEL-EXA®) and escitalopram (LEXAPRO®). As appreciated, the foregoing list is provided herein as exemplary and should not be considered exclusive or exhaustive.

Fluoxetine is a bicyclic compound, similar in structure to phenylpropanolamine. Fluoxetine structure imparts a high selectivity for interaction with cells of the nervous system for the function of preventing the re-uptake of serotonin into pre-synaptic cell storage sites. This action leads to marked increases in synaptic concentration of serotonin and is facilitative of numerous physiological processes requiring serotonin neurotransmission. In the pharmaeceutical field Fluoxetine is available as a hydrochloride salt (HCl).

S-adenosylmethionine (SAMe), is derived from two materials: methionine, a sulfur-containing amino acid, and adenosine triphosphate (ATP), the body's main energy compound. SAMe was originally developed around 1950 as an antidepressant, but it was also found to be helpful in the alleviation of arthritic symptoms. SAMe is essential for the manufacture of melatonin, which is needed to regulate steep. It also helps to protect DNA from harmful mutations and may help prevent certain types of nerve damage. Current clinical research is beginning to confirm these antidepressant qualities of SAMe.

Vitamin E, also named alpha-tocopherol, is a well-known scavenger of free-radicals in the body. Free-radical scavengers are sometimes referred to as anti-oxidants. This scavenging process is important for detoxifying the body of chemicals which are known to promote apoptosis, or programmed cell death. Apoptosis is a scientific description of cellular destruction. Although it is a popular anti-oxidant, Vitamin E is poorly soluble in water and thus can be administered only as a liquid-oil formulation or in an oil formulation enclosed in a soft elastic capsule. Vitamin E is typically measured in international units (IU) of alpha tocopherol.

In one presently preferred embodiment of the present invention, therapeutically effective amounts of Fluoxetine, SAMe and Vitamin E (active ingredients) may be introduced into receiving chambers of a multi-compartment capsule wherein Fluoxetine and SAMe comprises a physical state (e.g., solid, liquid, gas or dispersion) different from the physical state of Vitamin E. As shown in FIGS. 3 and 4, a therapeutically effective amount of Fluoxetine and SAMe may be introduced into receiving chamber 218*a* and a therapeutically effective amount of Vitamin E may be introduced into receiving chamber 218*b* of a multi-compartment capsule 210 of the present invention. Consistent with the foregoing, multi-compartment, multi-phase capsules and encapsulation technology are herein contemplated to produce a delivery vehicle for delivering mood enhancing, anti-depressant and anti-oxidant compounds to the body in a single dosage. A capsular format of the present invention may include the following composition:

| Receiving Chamber (218a): | |
|---|---|
| Fluoxetine [20-60 mg/day] | 20 mg |
| S-adenosylmethionine [200-1600 mg/day] | 1000 mg |

The incorporation of time-release coatings to varying the release rates of the active ingredients (e.g., Fluoxetine/SAMe and Vitamin E) in the primary and secondary capsules, respectively, of the multi-compartment capsule may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment.

According to one presently preferred embodiment of the present invention, a therapeutically effective amount of Fluoxetine and SAMe may be introduced into at least a portion of the receiving chamber 218*a* in the form of a solid and a therapeutically effective amount of Vitamin E may be introduced into at least a portion of the receiving chamber 218*b* of the primary capsule 211 in the form of a liquid.

In an alternative presently preferred embodiment of the present invention, therapeutically effective amounts of Fluoxetine and SAMe and Vitamin E (active ingredients) may be introduced into receiving chambers of a multi-compartment capsule wherein Fluoxetine and SAMe comprises a physical state (e.g., solid, liquid, gas or dispersion) different from the physical state of Vitamin E. As shown in FIG. 2, a therapeutically effective amount of Fluoxetine and SAMe, in the form of a solid, may be introduced into receiving chamber 118 and 138 and a therapeutically effective amount of Vitamin E, in the form of a liquid, may be introduced into receiving chamber 128 of a multi-compartment capsule 110 of the present invention. The material forming the primary capsule shell 111 may be formulated in a manner allowing for immediate dissolution and release of the of the contents of receiving chamber 118. The material forming the secondary capsule shell 120 may be formulated in a manner allowing for either an immediate dissolution or a time-delayed dissolution and release of the contents of receiving chamber 128. The material forming the tertiary capsule shell 138 may be formulated in a manner allowing for time-delayed dissolution and release of the contents of receiving chamber 138. In this presently preferred embodiment of the present invention, a total daily dosage of Fluoxetine and SAMe may be delivered as two separate dosages within a single oral dosage form. One presently preferred embodiment of the present invention thus makes for a more convenient dosage form.

Since the encapsulation process and multi-compartment, multi-phase capsule of the present invention are configured to apply to an anticipated treatment regime or medicinal design of a single dosage capsule, it will be readily appreciated that the introduction of one or more active ingredients into the receiving chambers of the primary and secondary capsules, respectively, is anticipated such that the various ingredients may be introduced in different receiving chambers to accommodate different treatment modalities. For example, a multi-compartment capsule may be formulated having Fluoxetine and SAMe introduced into the receiving chambers of the secondary capsule and Vitamin E may be introduced into the receiving chamber of the primary capsule. It is intended, therefore, that the examples provided herein be viewed as exemplary of the principles of the present invention, and not as restrictive to a particular structure or method for implementing those principles.

Example VII

Rofecoxib (Solid) & Vitamin E (Liquid)

As appreciated by those skilled in the art, arthritis is an inflammatory condition typically affecting the synovia and cartilage of joints. It has been estimated that as many as one in three persons may experience symptoms associated with arthritis during their lifetime.

In addition to arthritis, various other chronic, debilitating conditions may afflict the aged. Many of these conditions result from the natural process of aging in humans. The natural aging process is partially due to the accumulation and effects of toxic free-radical chemicals. Free-radicals result from several homeostatic biochemical processes. It is, accordingly, desirable to develop pharmaeceutical, biotechnical, nutraceutical or dietary supplement products which may alleviate multiple chronic, debilitating conditions. It is also desirable to package and administer such products in the most economic and convenient possible fashion.

Anti-inflammatory agents may have many diverse therapeutic roles in the human body. Inflammation is the process undertaken by the body as it responds to an injury. A typical inflammatory response involves blood vessel dilation, increased blood flow to the site of injury, and influx of white blood cells to process and remove dead tissue. Inflammation can lead to pain and swelling at the site of injury. Medicaments used in modulating the inflammatory response may be divided into steroid and non-steroidal labels. The latter is more commonly identified as non-steroidal anti-inflammatory drugs (NSAIDs).

Rofecoxib belongs to a class of NSAID compounds given the functional name cyclo-oxygenase-2 ("COX-2") inhibitors. This class may include, for example: rofecoxib (VIOXX®), celecoxib (CELEBREX®), valdecoxib (BEXTRA®), and meloxicam (MOBIC®). As appreciated, the foregoing list is provided herein as exemplary and should not be considered exclusive or exhaustive.

Rofecoxib is presently believed to inhibit the action of COX-2, an enzyme involved in the production of prostaglandins in the human body. Prostaglandins serve many diverse roles, one of which is to stimulate an inflammation mechanism in immune responses. Recently, Rofecoxib was labeled for use in the treatment of osteoarthritis, rheumatoid arthritis, acute pain, and primary dysmenorrhea.

Vitamin E, also named alpha-tocopherol, is a well-known scavenger of free-radicals in the body. Free-radical scavengers are sometimes referred to as anti-oxidants. This scavenging process is important for detoxifying the body of chemicals which are known to promote apoptosis, or programmed cell death. Apoptosis is a scientific description of cellular destruction. Although it is a popular anti-oxidant, Vitamin E is poorly soluble in water and thus can be administered only as a liquid-oil formulation or in an oil formulation enclosed in a soft elastic capsule.

In one presently preferred embodiment of the present invention, therapeutically effective amounts of Rofecoxib and Vitamin E (active ingredients) may be introduced into receiving chambers of a multi-compartment capsule wherein Rofecoxib comprises a physical state (e.g., solid, liquid, gas or dispersion) different from the physical state of Vitamin E. As shown in FIGS. 3 and 4, a therapeutically effective amount of Rofecoxib may be introduced into receiving chamber 218a and a therapeutically effective amount of Vitamin E may be introduced into receiving chamber 218b of a multi-compartment capsule 210 of the present invention. Consistent with the foregoing, multi-compartment, multi-phase capsules and encapsulation technology are herein contemplated to produce a delivery vehicle for delivering anti-inflammatory and anti-oxidant compounds to the body in a single dosage. A capsular format of the present invention may include the following composition:

| Receiving Chamber (218a): | |
|---|---|
| Rofecoxib [12.5-25 mg/day] | 25 mg |
| Receiving Chamber (218b): | |
| Vitamin E [200-400 IU/day] | 200 IU |

The incorporation of time-release coatings to varying the release rates of the active ingredients (e.g., Rofecoxib and Vitamin E) of the multi-compartment capsule 210 may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment.

According to one presently preferred embodiment of the present invention, a therapeutically effective amount of Rofecoxib may be introduced into at least a portion of the receiving chamber 218a in the form of a solid and a therapeutically effective amount of Vitamin E may be introduced into at least a portion of the receiving chamber 218b of the primary capsule 211 in the form of a liquid.

In an alternative presently preferred embodiment of the present invention, therapeutically effective amounts of Rofecoxib and Vitamin E (active ingredients) may be introduced into receiving chambers of a multi-compartment capsule wherein Rofecoxib comprises a physical state (e.g., solid, liquid, gas or dispersion) different from the physical state of Vitamin E. As shown in FIG. 2, a therapeutically effective amount of Rofecoxib, in the form of a solid, may be introduced into receiving chamber 118 and 138 and a therapeutically effective amount of Vitamin E, in the form of a liquid, may be introduced into receiving chamber 128 of a multi-compartment capsule 110 of the present invention. The material forming the primary capsule shell 111 may be formulated in a manner allowing for immediate dissolution and release of the contents of receiving chamber 118. The material forming the secondary capsule shell 120 may be formulated in a manner allowing for either an immediate dissolution or a time-delayed dissolution and release of the contents of receiving chamber 128. The material forming the tertiary capsule shell 138 may be formulated in a manner allowing for time-delayed dissolution and release of the contents of receiving chamber 138. In this presently preferred embodiment of the present invention, a total daily dosage of Rofecoxib may be delivered as two separate dosages within a single oral dosage form. One presently preferred embodiment of the present invention thus makes for a more convenient dosage form.

Since the encapsulation process and multi-compartment, multi-phase capsule of the present invention are configured to apply to an anticipated treatment regime or medicinal design of a single dosage capsule, it will be readily appreciated that the introduction of one or more active ingredients into receiving chambers defined within a capsule is anticipated such that the various ingredients may be introduced in different receiving chambers to accommodate different treatment modalities. It is intended, therefore, that the examples provided herein be viewed as exemplary of the principles of the present inven-

Example VIII

Diphenhydramine Hydrochloride (Solid) & Vitamin E (Liquid)

As appreciated by those skilled in the art, allergic reactions are conditions wherein the immune system is stimulated to identify, segregate and dispose of exogenous chemicals which cannot be recognized by the body. Allergic reactions are often associated with the release of histamine, a chemical compound which produces changes in the permeability of blood vessels and the accumulation of other immune system cells. In some circumstances, it may be desirable to modulate the amount of allergic response that is capable of being generated by the immune system.

Diphenhydramine belongs to a class of compounds which are given the functional name: histamine-1 ($H_1$) receptor antagonists. These compounds are more generally labeled as antihistamines. These antagonists are further divided according to their chemical structures. Diphenhydramine is an ethanolamine (aminoalkyl ether) derivative. Other chemical divisions may include, for example: ethylenediamine, propylamine, phenothiazine, piperazine. The ethanolamine division may include, for example: diphenhydramine, clemastine, dimenhydrinate, and doxylamine. As appreciated, the foregoing list is provided herein as exemplary and should not be considered exclusive or exhaustive.

Antihistamines block the interaction of the neurotransmitter, histamine, with $H_1$ receptors located in smooth muscle linings of the gastrointestinal tract, bronchial tract and large blood vessels. This blocking action may lead to marked relaxation in smooth muscle tone and is facilitative of numerous physiological processes including respiration.

The $H_1$ antagonists may also be divided according to their selectivity for central and peripheral $H_1$ receptors. A second-generation of $H_1$ has emerged in recent years. These agents have a greater selectivity for peripheral $H_1$ receptors. Second-generation $H_1$ receptor antagonists may include, for example: azelastine (ASTELIN®), cetirizine (ZYRTEC®), desloratadine (CLARINEX®), fexofenadine (ALLEGRA®) and loratadine (CLARITINn®).

Vitamin E, also named alpha-tocopherol, is a well-known scavenger of free-radicals in the body. Free-radical scavengers are sometimes referred to as anti-oxidants. This scavenging process is important for detoxifying the body of chemicals which are known to promote apoptosis, or programmed cell death. Apoptosis is a scientific description of cellular destruction. Although it is a popular anti-oxidant, Vitamin E is poorly soluble in water and thus can be administered only as a liquid-oil formulation or in an oil formulation enclosed in a soft elastic capsule.

In one presently preferred embodiment of the present invention, therapeutically effective amounts of Diphenhydramine and Vitamin E (active ingredients) may be introduced into receiving chambers of a multi-compartment capsule wherein at least two of the active ingredients have physical states (e.g., solid, liquid, gas or dispersion) that differ. Consistent with the foregoing, multi-compartment, multi-phase capsules and encapsulation technology as herein contemplated to produce a delivery vehicle for delivering anti-allergic and anti-oxidant compounds to the body in a single dosage. A capsular format of the present invention may include the following composition:

| Primary Capsule: | |
|---|---|
| Diphenhydramine HCl [25-100 mg/day] | 50 mg |
| Secondary Capsule: | |
| Vitamin E [200-400 IU/day] | 200 IU |

The incorporation of time-release coatings to varying the release rates of the active ingredients (e.g., Diphenhydramine and Vitamin E) in the primary and secondary capsules, respectively, of the multi-compartment capsule may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment.

A therapeutically effective amount of Diphenhydramine may be introduced into at least a portion of the internal periphery of the receiving chambers of a primary capsule in the form of a solid and a therapeutically effective amount of Vitamin E may be introduced into at least a portion of a secondary capsule in the form of a liquid, if desired. Since the encapsulation process and multi-compartment, multi-phase capsule of the present invention are configured to apply to an anticipated treatment regime or medicinal design of a single dosage capsule, it will be readily appreciated that the introduction of one or more active ingredients into the receiving chambers of the primary and secondary capsules, respectively, is anticipated such that the various ingredients may be introduced in different receiving chambers to accommodate different treatment modalities. For example, a multi-compartment capsule may be formulated having Diphenhydramine introduced into the receiving chambers of the secondary capsule and Vitamin E may be introduced into the receiving chamber of the primary capsule. It is intended, therefore, that the examples provided herein be viewed as exemplary of the principles of the present invention, and not as restrictive to a particular structure or method for implementing those principles.

Example IX

Celecoxib (Solid) & Ibuprofen (Liquid)

As appreciated by those skilled in the art, arthritis is an inflammatory condition typically affecting the synovia and cartilage of joints. It has been estimated that as many as one in three persons may experience symptoms associated with arthritis during their lifetime.

Anti-inflammatory agents may have many diverse therapeutic roles in the human body. Inflammation is the process undertaken by the body as it responds to an injury. A typical inflammatory response involves blood vessel dilation, increased blood flow to the site of injury, and influx of white blood cells to process and remove dead tissue. Inflammation can lead to pain and swelling at the site of injury. Medicaments used in modulating the inflammatory response may be divided into steroid and non-steroidal labels. The latter is more commonly identified as non-steroidal anti-inflammatory drugs (NSAIDs).

Celecoxib belongs to a class of NSAID compounds given the functional name cyclo-oxygenase-2 ("COX-2") inhibitors. This class may include, for example: rofecoxib (VIOXX®), celecoxib (CELEBREX®), valdecoxib (BEXTRA®), etodolac (LODINE®) and meloxicam (MOBIC®). As appreciated, the foregoing list is provided herein as exemplary and should not be considered exclusive or exhaustive.

Celecoxib is believed to inhibit the action of COX-2, an enzyme involved in the production of prostaglandins in the human body. Prostaglandins serve many diverse roles, one of which is to stimulate an inflammation mechanism in immune responses. Recently, Celecoxib was labeled by the United States Food and Drug Administration (FDA) for use in the treatment of osteoarthritis, rheumatoid arthritis, acute pain, and primary dysmenorrhea.

Ibuprofen is another NSAID and is believed to function as a non-selective inhibitor of cyclo-oxygenase. Ibuprofen has been labeled by the FDA for use in the treatment of osteoarthritis, rheumatoid arthritis, relief of mild to moderate pain and primary dysmenorrhea. Ibuprofen belongs to a class of compounds called phenyl-a-methylacetic acids, which are derived from salicylic acid. Non-selective cyclo-oxygenase inhibitors may include, for example: ibuprofen (MOTRIN®), naproxen (NAPROSYN®), diclofenac (VOLTAREN®), flurbiprofen (ANSAID®), indomethacin (INDOCIN®), ketoprofen (ORUDIS®), ketorolac (TORADOL®), nabumetone (RELAFEN®), oxaprozin (DAYPRO®), piroxicam (FELDENE®) and sulindac (CLINORIL®). As appreciated, the foregoing list is provided herein as exemplary and should not be considered exclusive or exhaustive.

In one presently preferred embodiment of the present invention, therapeutically effective amounts of Celecoxib and Ibuprofen (active ingredients) may be introduced into receiving chambers of a multi-compartment capsule wherein Celecoxib comprises a physical state (e.g., solid, liquid, gas or dispersion) different from the physical state of Ibuprofen. As shown in FIGS. 3 and 4, a therapeutically effective amount of Celecoxib may be introduced into receiving chamber 218a and a therapeutically effective amount of Ibuprofen may be introduced into receiving chamber 218b of a multi-compartment capsule 210 of the present invention. Consistent with the foregoing, multi-compartment, multi-phase capsules and encapsulation technology are herein contemplated to produce a delivery vehicle for delivering anti-arthritic and anti-oxidant compounds to the body in a single dosage. A capsular format of the present invention may include the following composition:

| Receiving Chamber (218a): | |
|---|---|
| Celecoxib<br>[200-400 mg/day]<br>Receiving Chamber (218b): | 200 mg |
| Ibuprofen<br>[2400-3200 mg/day] | 800 mg |

The incorporation of time-release coatings to varying the release rates of the active ingredients (e.g., Celecoxib and Ibuprofen) of the multi-compartment capsule 210 may be used to target key time intervals or events when the body may be most able to utilize the named active ingredients. Thus, the incorporation of time-release coatings in the encapsulation process when forming a multi-compartment capsule may be specifically designed to fit the needs and desires of numerous different users having similar conditions that are being targeted for treatment.

According to one presently preferred embodiment of the present invention, a therapeutically effective amount of Celecoxib may be introduced into at least a portion of the receiving chamber 218a in the form of a solid and a therapeutically effective amount of Ibuprofen may be introduced into at least a portion of the receiving chamber 218b of the primary capsule 211 in the form of a liquid.

In an alternative presently preferred embodiment of the present invention, therapeutically effective amounts of Celecoxib and Ibuprofen (active ingredients) may be introduced into receiving chambers of a multi-compartment capsule wherein Celecoxib comprises a physical state (e.g., solid, liquid, gas or dispersion) different from the physical state of Ibuprofen. As shown in FIG. 2, a therapeutically effective amount of Celecoxib, in the form of a solid, may be introduced into receiving chamber 128 and a therapeutically effective amount of Ibuprofen, in the form of a liquid, may be introduced into receiving chambers 118 and 138 of a multi-compartment capsule 110 of the present invention.

The material forming the primary capsule shell 111 may be formulated in a manner allowing for immediate dissolution and release of the of the contents of receiving chamber 118. The material forming the secondary capsule shell 120 may be formulated in a manner allowing for either an immediate dissolution or a time-delayed dissolution and release of the contents of receiving chamber 128. The material forming the tertiary capsule shell 138 may be formulated in a manner allowing for time-delayed dissolution and release of the contents of receiving chamber 138. In this presently preferred embodiment of the present invention, a total daily dosage of Ibuprofen may be delivered as two separate dosages within a single oral dosage form. One presently preferred embodiment of the present invention thus makes for a more convenient dosage form.

Since the encapsulation process and multi-compartment, multi-phase capsule of the present invention are configured to apply to an anticipated treatment regime or medicinal design of a single dosage capsule, it will be readily appreciated that the introduction of one or more active ingredients into receiving chambers defined within a capsule is anticipated such that the various ingredients may be introduced in different receiving chambers to accommodate different treatment modalities. It is intended, therefore, that the examples provided herein be viewed as exemplary of the principles of the present invention, and not as restrictive to a particular structure or method for implementing those principles.

Examples X

Some embodiments of the present invention will use one or more of the below ingredients in a multi-compartment capsule, combinable as would be recognized in view of the teachings of the present application in combination with the knowledge available to one of ordinary skill in the art. It is noted that the following non-limiting lists illustrate exemplary ingredients that can be used with the present invention, including the the broader subclasses and classes to which they belong.

| Botanicals | |
|---|---|
| Acerola Extracts | Alfalfa |
| Algae, Blue Green | Aloe |

| Botanicals | |
|---|---|
| Amla | Angelica Root |
| Bacopa Monnieri | Mucuna Pruriens |
| Anise Seed | Arnica |
| Artichoke | Ashwagandha |
| Astragalus | Ayurvedic Herbs |
| Barberry | Barley Grass |
| Barley Sprout Extract | Benzoin |
| Bilberry | Bioflavonoids |
| Bitter Melon | Bitter Orange |
| Black Cohosh | Black Currant |
| Black Walnut | Bladderwrack |
| Blue Cohosh | Blueberry |
| Boswellia | Brahmi |
| Broccoli | Burdock |
| Butcher's Broom | Calendula |
| Capsicum | Cascara Sagrada |
| Cat's Claw | Cayenne |
| Celery Seed | Certified Organic Herbs |
| Chamomile | Chapparal |
| Chaste Berry | Chicory Root |
| Chinese Herbs | Chlorella |
| Chlorophyll | Citrus Aurantium |
| Cocoa | Coriander |
| Corn Silk | Cranberry |
| Curcuminoids | Damiana |
| Dandelion | Devil's Claw |
| Diosgenin | Dong Quai |
| Echinacea | Elderberry |
| Elecampane Root | Ephedra |
| Essential Oils | Eucalyptus |
| Evening Primrose | Eyebright |
| Fennel | Fenugreek |
| Feverfew | Flax Products |
| Fo Ti | Garcinia Cambogia |
| Garlic | Gentian |
| Ginger | Ginkgo Biloba |
| Ginseng (American) | Ginseng (Panax) |
| Ginseng (Siberian) | Goldenseal |
| Gotu Kola | Grape Seed Extract |
| Grape Skin Extract | Grapefruit Seed Extract |
| Green Food Products | Green Lipped Mussel Powder |
| Green Tea | Griffonia Simplicifolia |
| Guarana | Guggul |
| Gymnema Sylvestre | Hawthorne |
| Henna | Herbal Extracts, Standardized |
| Herbal Teas | Hops |
| Horehound | Horse Chestnut |
| Horsetail | Hysop |
| Ipriflavone | Jojoba Oil |
| Juniper Berries | Kava Kava |
| Kelp Extract | Kola Nut |
| Kombucha | Kudzu |
| Larch | Lavender |
| Lemon Balm | Licorice Extract |
| Linden Flowers | Lobelia |
| Maca | Maitake Mushroom |
| Marshmallow | Milk Thistle |
| Molasses | Mushrooms |
| Neem | Nettle |
| Noni | Nopal |
| Oatstraw | Octacosanol |
| Olive Extract | Orange Peel Extract |
| Oregano Oil | Oregon Mountain Grape |
| Organic Sweeteners | Parsley |
| Passion Flower | Pau d'Arco |
| Pennyroyal | Peppermint |
| Pfaffia Paniculata | Pine Bark Extract |
| Piper Longum | Pygeum Africanum |
| Quercitin | Raspberry Powder |
| Red Clover | Red Raspberry |
| Reishi Mushroom | Resveratrol Extract |
| Rhubarb Root | Rice Products |
| Rose Hips | Rosemary Extract |
| Sage | Sarsaparilla |
| Saw Palmetto | Schizandra |
| Seaweed extracts | Senna |
| Shatavari | Shiitake Mushroom |
| Silymarin | Skullcap |
| Slippery Elm | Soy Isoflavones |
| Soybean Products | Spirulina |
| St. John's Wort | Stevia |
| Summa | Tea Tree Oil |
| Terminalia Ajruna | Tribulus Terrestris |
| Triphala | Tumeric |
| Uva Ursi | Valerian Extract |
| Vegetable Extracts | Vitex |
| Wheat Germ | White Willow Bark |
| Wild Cherry bark | Wild Yam |
| Witch Hazel | Wormwood |
| Yarrow | Yellow Dock |
| Yerba Sante | Yohimbine |
| Yucca | |

| Extracts | |
|---|---|
| 20-ECD 7-9% | 4-Androstenedione 99% |
| Acetyl L-Carnitine HCl 99% | Adenophora Tetraohylla Ext 5:1 |
| Alisma Extract 10:1 | Alpha Lipoic Acid 99% |
| Angelica Root Extract | Arbutin 99% |
| Artemisia Extract 4:1 | Artichoke Extract 5%, Globe |
| Asparagus Extract 4:1 | Asparagus Powder |
| Astragulus Extract 10:1 | Astragulus Extract 4:1 |
| Astragulus Extract 5:1 | Astragulus Root Extract 0.5% |
| Astragulus Root Powder | Atractylodes Extract 10:1 |
| Avena Sativa Extract 10:1 | Avena Sativa Extract 4:1 |
| Barbed Skullcap Extract 10:1 | Barberry Extract 10% |
| Bee Pollen Powder | Beta-Sisterol 35% |
| Bilberry Extract 10:1 | Bitter Melon Extract 8:1 |
| Black Cohosh Extract 2.5% | Black Cohosh Root Powder |
| Black Pepper Extract 4:1 | Black Soy Bean Extract 10:1 |
| Bone Powder | Boswellia Serrata Extract 65% |
| Broccoli Sprout Extract 10:1 | Buchu Leaf Powder |
| Buplerum (Chai Hu) Extract 5:1 | Burdock Root Extract 4:1 |
| Cabbage Extract 4:1 | Caffeine (Natural) 86-87% |
| Caffeine 99% | Calcium Citrate Granular 21% |
| Calcium-Pyruvate 99% | Carrot Root Extract 4:1 |
| Cassia Nomame Extract 4:1 | Catnip Extract 4:1 |

-continued

| Extracts | |
|---|---|
| Cat's Claw (Inner Bark) Powder | Cauliflower Extract 4:1 |
| Celandine (Greater) Extract 4:1 | Celery Seed Extract |
| Cetyl Myristoleate 11% | Cetyl Myristoleate 20% |
| Chaenomeles Extract 4:1 | Chamomile Flower Extract 10:1 |
| Chamomile Flower Extract 4:1 | Chaste Tree Berry Extract 4:1 |
| Chitin | Chitosan 80% |
| Chitosan 90% | Chondroitin Sulfate 90% |
| Chrysin 99% | Cinnamon Powder |
| Cistanches Extract 5:1 | Citrus Aurantium Extract 6% |
| Citrus Bioflavonoid Complex 13% | Citrus Peel Extract 5:1 |
| Clove Extract 5:1 | Clove Powder |
| Coca Extract 4:1 | Codonopsis Pilosula Extract 5:1 |
| Colostrum | Common Peony Extract 8:1 |
| Cordyceps Extract 7% | Cornsilk Extract 4:1 |
| Cornsilk Powder | Corydalis Extract 10:1 |
| Cranberry Extract 4:1 | Cranberry Powder |
| Curcumin Extract 95% | Cuscuta Extract 5:1 |
| Damiana Extract 4:1 | Damiana Leaves Powder |
| Dandelion Powder | Dandelion Root Extract 6:1 |
| Danshen Extract 80% | D-Calcium Pantothenate |
| Devil's Claw Extract 2.5% | Devil's Claw Extract 4:1 |
| Devil's Claw Root Powder | DHEA 99% |
| Diosgenin 95% | DL-Phenyl Alanine |
| DMAE Bitartrate | Dong Quai Extract 10:1 |
| Dong Quai Extract 4:1 | Dong Quai Root Powder |
| D-Ribose | Echinacea Angustifolia Extract 4:1 |
| Echinacea Leaf Powder | Echinacea Purpurea Extract 10:1 |
| Echinacea Purpurea Extract 4% | Echinacea Purpurea Extract 4:1 |
| Echinacea Purpurea Root Powder | Elder Flower Extract 4:1 |
| Elderberry Extract 20:1 | Elderberry Extract 4:1 |
| Epimedium Extract 10% | Epimedium Extract 10:1 |
| Epimedium Extract 4:1 | Epimedium Extract 5% |
| Epimedium Powder | Eucommia (Du Zhong) Extract 5:1 |
| Fennel Seed Extract 4:1 | Fennel Seed Powder |
| Fenugreek Extract 4:1 | Fenugreek Extract 6:1 |
| Feverfew Extract 5:1 | Fisetin |
| Fish Oil Powder | Forbidden Palace Flower Extract 5:1 |
| Forskolin 8% | Fo-Ti Extract 12:1 |
| Fo-Ti Extract 8:1 | Fo-Ti Powder |
| Gardenia Extract 8:1 | Garlic Extract 4:1 |
| Garlic Powder | Gentian Root Extract 6:1 |
| Ginger Extract 4:1 | Ginger Root Extract 5% |
| Ginger Root Powder | Ginkgo Biloba Extract 8:1 |
| Ginkgo Extract 24/6% | Ginkgo Extract 24/6% < 5 |
| Ginkgo Extract 24/7% | Ginkgo Leaf Extract 4:1 |
| Ginkgo Leaf Powder | Ginseng (Korean) Powder |
| Ginseng (Panax) Extract 5% | Ginseng (Panax) Extract 8% |
| Ginseng (Panax) Extract 80% | Glucomannans Konjac Powder |
| Glucosamine HCl 95% Granulation | Glucosamine HCl 99% |
| Glucsosamine Sulfate Potassium | Glucsosamine Sulfate Sodium 95% Granulation |
| Glucsosamine Sulfate Sodium 99% | Goldenrod Extract 4:1 |
| Goldenrod Powder | Goldenseal Root Extract 14% |
| Goldenseal Root Powder | Gotu Kola Extract 16% |
| Gotu Kola Extract 4:1 | Gotu Kola Extract 8:1 |
| Gotu Kola Powder | Grape Fruit Powder |
| Grape Seed | Grape Seed Extract 10:1 |
| Grape Seed Extract 20:1 | Grape Seed Extract 4:1 |
| Grape Seed Extract 5:1 | Grape Seed Extract 95% |
| Grape Seed Powder | Grape Skin Extract 20:1 |
| Grape Skin Extract 4:1 | Grass-Leaved Sweetflai Extract |
| Green Lip Mussel Extract | Green Tea Extract 30% |
| Green Tea Extract 4:1 | Green Tea Extract 95% |
| Guarana Seed Extract 10% | Guarana Seed Extract 22% |
| Guarana Seed Extract 25% | Guggul Extract 10% |
| Guggul Extract 2.5% | Gugulipid Extract 10% |
| Gymnema Sylvestre Extract 25% | Gymnema Sylvestre Powder |
| Hawthorne Berry Extract 4:1 | Hawthorne Berry Powder |
| Hawthorne Leaf Extract 2% | Hearbacious Peony Extract 5:1 |
| Hesperidin Extract 98% | Honeysuckle Herb Extract 4:1 |
| Hops Flower Extract 4:1 | Horehound Extract 10:1 |
| Horehound Extract 4:1 | Horehound Herb Powder |
| Horse Chestnut Extract 20% | Horse Chestnut Extract 4:1 |
| Horse Chestnut Powder | Horsetail Extract 7% |
| Horsetail Powder | Houttuynia Cordata Extract 5:1 |
| Hydrangea Extract 8:1 | Hydroxy Apatite |
| Hyssop Extract 4:1 | Indole-3-Carbinol 99% |
| Isodon Glaucocalyx Extract 10:1 | Japanese Knotweed Extract |

-continued

| Extracts | |
|---|---|
| Jiaogulan Extract 4:1 | Jin Qian Cao Extract 4:1 |
| Jingjie Extract 4:1 | Jujube Fruits Extract 4:1 |
| Kava Kava Extract 30% | Kava Kava Powder |
| Kelp Extract 4:1 | Kelp Powder |
| Kidney Bean Extract 10:1 | Kidney Bean Pole 4:1 |
| Kidney Bean Pole 8:1 | Kidney Bean Powder |
| Kola Nut Extract 10% | Kudzu Extract 4:1 |
| Kudzu Extract 6:1 | Lettuce Extract 4:1 |
| L-Glutamine | L-Glycine |
| Licorice Extract 10% | Licorice Extract 5:1 |
| Licorice Powder | Lotus Leaf Powder |
| L-Tyrosine | Lycium Fruit Extract 4:1 |
| Lycium Fruit Extract 5:1 | Ma Huang Extract 6% |
| Ma Huang Extract 8% | Maca Extract 0.6% |
| Maca Extract 4:1 | Maca Root Powder |
| Magnesium Stearate | Magnolia Bark Powder |
| Magnolia Officinal Extract 4:1 | Maitake Mushroom Extract 4:1 |
| Marigold Extract (Lutein 5%) | Methozyisoflavone 99% |
| Methylsufonylmethane 99% | Milk Thistle Extract 4:1 |
| Milk Thistle Seed Extract 80% silymarin | Morinda Extract 5:1 |
| Motherwort Extract 4:1 | Motherwort Powder |
| Mucuna Pruriens Extract (15% L-Dopa) | Muira Puama Extract 12:1 |
| Muira Puama Extract 4:1 | Muira Puama Powder |
| Mushroom Extract 10:1 (feishi) | Mustard Seed Extract 8:1 |
| Myrobalan Extract 4:1 | Myrrha Gum Extract 2.5% |
| N-Acetyl-D-Glucosamine | N-Acetyl-L-Cysteine |
| Nettle Extract 7% | Nettle Leaf Extract 4:1 |
| Nettle Leaf Powder | Noni Powder |
| Olive Leaf Extract 18% | Olive Powder |
| Orange Peel Extract 4:1 | Orange Peel Powder |
| Oroxylum Indicum Extract 4:1 | Oroxylum Indicum Powder |
| Oyster Meat Powder | Oyster Shell Powder |
| Papaya Fruit Extract 4:1 | Parsley Extract 10:1 |
| Parsley Extract 4:1 | Parsley Leaf Extract 4:1 |
| Parsley Powder | Passion Flower Extract 4:1 |
| Passion Flower Powder | Pau D'Arco Powder |
| Peppermint Extract 4:1 | Peppermint Powder |
| Perilla Seed Extract 4:1 | Periwinkle Extract 4:1 |
| Pharbitidis Extract 4:1 | Phosphatidyl Serine 20% |
| Pine Bark Extract 4:1 | Plantago Asiatica Leaf Extract 5:1 |
| Polygala Tenoifolia Extract 4:1 | Polygonum Extract |
| Polygonum Extract 4:1 | Pregnenolone 99% |
| Propolis Extract 3% | Pseudoginseng Extract |
| Psyllium extract 4:1 | Pumpkin Seed Extract 4:1 |
| Purple Willow Bark Extract 4:1 | Purslane Herb Extract 4:1 |
| Pygeum Extract 4:1 | Quercetin |
| Radish Extract 4:1 | Radix Isatidis Extract 4:1 |
| Radix Polygoni Extract 4:1 | Red Clover Extract 4:1 |
| Red Pepper Extract 4:1 | Red Yeast Rice |
| Red Yeast Rice Extract 10:1 | Red Yeast Rice Powder |
| Rehmannia Root Extract 4:1 | Reishi Mushroom Extract 4:1 |
| Rhodiola Rosea Extract 4:1 | Rhododendron Extract 4:1 |
| Rhododendron Powder | Rhubarb Extract 4:1 |
| Rhubarb Root Powder | Riboflavin (B2) |
| Rice Powder | Rosemary Extract 20% |
| Rumex Madaid Extract 4:1 | Salvia Extract 10:1 |
| Salvia Extract 4:1 | SAMe |
| Saw Palmetto Extract 25% | Saw Palmetto Extract 25% |
| Saw Palmetto Extract 25% | Saw Palmetto Extract 4:1 |
| Saw Palmetto Extract 45-50% | Saw Palmetto Oil 85-95% |
| Saw Palmetto Powder | Schizandra Extract 10:1 |
| Schizandra Extract 4:1 | Scopolia Acutangula Powder |
| Sea Cucumber Powder | Senna Leaf Powder |
| Sesame (Black) Seed Powder | Shark Cartilage Powder |
| Shitake Mushroom Extract | Siberian Ginseng Extract 0.8% |
| Siberian Ginseng Extract 4:1 | Siberian Ginseng Powder |
| Skullcap Extract 4:1 | Skullcap Extract 4:1 |
| Slippery Elm Powder | Sodium-Pyruvate 99% |
| Songaria Cynomorium Extract 4:1 | Songaricum Powder |
| Spirulina Powder | St. John's Wort Extract 0.3% |
| St. John's Wort Extract 4:1 | St. John's Wort Powder |
| Stanol 50% | Stephania Extract 4:1 |
| Stevia Extract 4:1 | Sulfate N+ |
| Suma Root Extract 4:1 | Suma Root Powder |
| Taurine Powder | Thorowax Extract 4:1 |
| Tomato Extract | Tomato Extract (0.2% Lycopene) |
| (trans)-Resveratrol 20-25% | Tribulus Extract 10:1 |

-continued

Extracts

| | |
|---|---|
| Tribulus Extract 40% | Tribulus Powder |
| Trifal Extract 4:1 | Turmeric Extract 4:1 |
| Turmeric Root Powder | Uva Ursi Extract 4:1 |
| Uva Ursi Powder | Valerian Root Extract 0.8% |
| Valerian Root Extract 4:1 | Valerian Root Powder |
| Vinca Major Seed Extract 10:1 | White Wax Extract 4:1 |
| White Willow Bark 15% (total salicins) | White Willow Bark 20% |
| White Willow Bark 25% | White Willow Bark Extract 4:1 |
| White Willow Bark Powder | Wild Yam Extract 10:1 |
| Wild Yam Extract 16% | Wild Yam Extract 4:1 |
| Wild Yam Extract 6% | Wild Yam Powder |
| Williams Elder Extract 4:1 | Wolfberry Fruit Extract 10:1 |
| Wolfiporia Extract 8:1 | Yellow Dock Root Extract 4:1 |
| Yerba Mate Extract (2% caffeine) | Yerba Mate Extract 4:1 |
| Yohimbe Bark Extract 15:1 | Yohimbe Bark Extract 2% |
| Yohimbe Bark Extract 3% | Yohimbe Bark Powder |
| Yucca Extract 4:1 | |

Enzymes

| | |
|---|---|
| Alpha Galactosidase | Amylase |
| Bromelain | Cellulase |
| Papain | Peptidase |
| Protease | Proteolytic Enzymes |
| Superoxide Dismutase | Trypsin |

Phospholipids

| | |
|---|---|
| Lecithin | Phosphatidyl Choline |
| Phosphatidyl Serine | |

Specialty Nutraceuticals

| | |
|---|---|
| 5-Hydroxytryptophan | Acetyl L-Carnitine |
| Alpha Lipoic Acid | Alpha-Ketoglutarates |
| Bee Products | Betaine Hydrochloride |
| Bovine Cartilage | Caffeine |
| Cetyl Myristoleate | Charcoal |
| Chitosan | Choline |
| Chondroitin Sulfate | Coenzyme Q10 |
| Collagen | Colostrum |
| Creatine | Cyanocobalamin (Vitamin B12) |
| DMAE | Fumaric Acid |
| Germanium Sesquioxide | Glandular Products |
| Glucosamine HCL | Glucosamine Sulfate |
| HMB (Hydroxyl Methyl Butyrate) | Immunoglobulin (Immune System Support) |
| Lactic Acid | L-Carnitine |
| Liver Products | Malic Acid |
| Maltose-anhydrous | Mannose (d-mannose) |
| MSM | Other Carnitine Products |
| Phytosterols | Picolinic Acid |
| Pyruvate | Red Yeast Extract |
| SAMe | Selenium Yeast |
| Shark Cartilage | Theobromine |
| Vanadyl Sulfate | Velvet Deer Antler |
| Yeast | |

Herbal Oils

| | |
|---|---|
| Aloe Vera | Artichoke Oil |
| Artichoke Oil | Black Currant Seed Oil 14% GLA |
| Black Currant Seed Oil 15% GLA | Borage Oil 20% GLA |
| Borage Oil 22% GLA | Boswellia Serrata Oil |
| CLA Conjugated Linolic Acid 75% min. | Evening Primrose Oil 10% GLA |
| Evening Primrose Oil 9% GLA | Flax Seed Oil 50% ALA |
| Garlic Oil | Grape Seed Oil |
| Guggul Lipid Oil | Olive Leak Extract |

Herbal Oils

| | |
|---|---|
| Oregano Oil | Perilla Oil 60% ALA |
| Pumpkin Seed Oil | Pygeum Oil |
| Rosehip Oil | Rosemary Oil |
| Saw Palmetto Oil | Sterols |
| Tocotrienol Palm Oil | Walnut Oil |
| Wheat Germ Oil | Sesame Seed Oil |
| | Dill Seed Oil |
| | Clove Bud Oil |
| | Ginger Root Oil |
| | Cinnamon Leaf Oil |
| | Fennel Seed Oil |
| | Curcuma Longa Oil |
| | Cummin Seed Oil |
| | Celery Seed Oil |
| | Coriander Seed Oil |
| | Red Rasberry Seed Oil |
| | Cranberry Seed Oil |
| | Blackberry Seed Oil |

Marine Oils

| | |
|---|---|
| Cod Liver Oil (1000 A/100 D) | Cod Liver Oil (2500A/250D) |
| Fish Oil 30% EPA/20% DHA | Fish Oil Concentrated |
| Fish Oil Deodorized | Marine Lipid Oil 18/12 |
| Marine Lipid Oil 30/20 | Marine Lipid Oil 36/24 |
| Salmon Oil 18% EPA/12% DHA | Squalene Oil (Shark) |

Other Oils

| | |
|---|---|
| Alpha Lipoic Acid | Cetyl Myristoleate CM |
| Coenzyme Q10 . | Lecithin |
| Medium Chain Triglycerides MCT. | |

Vitamins

| | |
|---|---|
| Ascorbic Acid (Vitamin C) | B Vitamins |
| Biotin | Fat Soluble Vitamins |
| Folic Acid | HCA (Hydroxycitric Acid) |
| Inositol | Mineral Ascorbates |
| Mixed Tocopherols | Niacin (Vitamin B3) |
| Orotic Acid | PABA (Para-Aminobenzoic Acid) |
| Pantothenates | Pantothenic Acid (Vitamin B5) |
| Pyridoxine Hydrochloride (Vitamin B6) | Riboflavin (Vitamin B2) |
| Synthetic Vitamins | Thiamine (Vitamin B1) |
| Tocotrienols | Vitamin A |
| Vitamin D | Vitamin E |
| Vitamin F | Vitamin K |
| Vitamin Oils | Vitamin Premixes |
| Vitamin-Mineral Premixes | Water Soluble Vitamins |

Carotenoids

| | |
|---|---|
| Apocarotenal | Astaxanthin |
| Beta-Carotene | Canthaxanthin |
| Carotenoids | Lutein/Lutein Esters |
| Lycopene | Zeaxanthin |

Hormones

| | |
|---|---|
| 7-Keto-DHEA | Androstenedione |
| DHEA | Melatonin |
| Nor-Androstenedione | Pregnenolone |
| Progesterone | 19 Nor-4-Androstendiol |
| | 19 Nor-4-Androstenedione |
| | 19 Nor-5-Androstenediol |
| | 19 Nor-5-Androstendione |
| | 3-Indolebutyric Acid |
| | 4 Androstendiol |
| | 4 Androstendione |
| | 6 Furfurylaminopurene |
| | 6-Benzylaminopurine |

| Minerals | |
|---|---|
| Boron | Calcium |
| Chelated Minerals | Chloride |
| Chromium | Coated Minerals |
| Cobalt | Copper |
| Dolomite | Iodine |
| Iron | Magnesium |
| Manganese | Mineral Premixes |
| Mineral Products | Molybdenum |
| Other Minerals | Phosphorus |
| Potassium | Selenium |
| Sodium | Specialty Minerals |
| Trace Minerals | Vanadium |
| Zinc | Malic Acid |
| | Pyruvate |

| Probiotics | |
|---|---|
| *Acidophilus* | Bifido Bacteria |
| *Lactobacillus* | |

| Proteins/Amino Acids | |
|---|---|
| Amino Acids | Betaine |
| Casein | Functional Soy |
| Glutamic Acid | L-Alanine |
| L-Arginine | L-Cysteine |
| L-Glutamine | L-Glycine |
| L-Histidine | L-Isoeucince |
| L-Leucine | L-Lysine |
| L-Methionine | L-Ornithine |
| L-Phenylalaline | L-Proline |
| L-Taurine | L-Threonine |
| L-Tryptophan | L-Tyrosine |
| L-Valine | N-Acetly-L-Cysteine |
| Protein | Soluble Soy |
| Soy Protein Isolates | Textured Soy |
| Whey Protein Isolates | |

Specialty Nutrients

ATP

Forskolin

Sterol Esters

Stanol Esters

Probiotics

Lactoferin

Lutein Esters

Zeaxanthin

Immunoglobulins

Ipriflavone

Isoflavones

Fructo-Oligo-Saccharides

Inulin

Huperzine A

Melatonin

Medicinal Mushrooms

Bile Products

Peptone Products

Glandular Products

Pancreatic Products

Thyroid Products

Ribose

Probiotics

Oleo Resins

Dill Seed Oleo Resin

Black Pepper Oleoresin

Capsicum Oleoresin

Examples XI

The present invention further contemplates the use of any active ingredients or medicaments known in the art. In this regard, it is well within the purview of the skilled artisan to select a particular combination of active ingredients or medicaments. The following non-limiting lists illustrate exemplary active ingredients or medicaments and the broader subclasses and classes to which they belong for use in this invention.

Medicaments Acting on the Autonomic Nervous System
    Adrenergic Medicaments
    Cholinergic Medicaments
    Direct Muscarinic Agonists Choline Esters
        acetylcholine
        bethanechol (URECHOLINE®)
        carbachol
        methacholine (PROVOCHOLINE®)
    Alkaloids
        muscarine
        pilocarpine (PILOCAR®)
    Direct Nicotinic Agonist
        nicotine
    Acetylcholinesterase Inhibitors Acetylcholinesterase Inhibitors ("Reversible")
        edrophonium (TENSILON®)
        neostigmine (PROSTIGMIN®)
        physostigmine (ANTILIRIUM®)
    Acetylcholinesterase Inhibitors ("Irreversible")
        (diisopropylflurorphosphate DFP)
        echothiophate (PHOSPHOLINE®)
        isoflurophate (FLOROPRYL®)
    Muscarinic Antagonists Atropine
        ipratropium (ATROVENT®)
        pirenzepine
        scopolamine
    2-PAM: Acetylcholinesterase Reactivator Pralidoxime (Protopam) {2-PAM}: peripheral acetylcholinesterase reactivator for certain phosphoryl-enzyme complexes
    Ganglionic Blockers
        hexamethonium
        mecamylamine (INVERSINE®)
        trimethaphan
    Catecholamines
        dobutamine (DOBUTREX®)
        dopamine (INTROPIN®)
        epinephrine isoproterenol (ISUPREL®)
norepinephrine (LEVOPHED®)
Direct Adrenoceptor Agonist Medicaments
   albuterol (VENTOLIN®, PROVERITIL®)
   clonidine (CATAPRES®)
   methoxamine (VASOXYL®)
   oxymetazohne (AFRIN®)
   phenylephrine (NEO-SYNEPHRINE®)
   ritodrine (YUTOPAR®)
   salmeterol (SEREVENT®)
   terbutaline (BRETHINE®)
Indirect-Acting Sympathomimetic Medicaments
   amphetamine
   cocaine
   ephedrine, Pseudoephedrine tyramine
Alpha-Adrenoceptor Antagonists Medicaments
   doxazosin (Cardura CARDURA®)
   labetalol (TRANDATE®, NORMODYNE®)
   phenoxybenzamine (DIBENZYLINE®)
   phentolamine (REGITINE®)
   prazosin (MINIPRESS®)
   terazosin (HYTRIN®)
   tolazoline (PRISCOLINE®)
   trimazosin
   yohimbine (YOCON®)
β-Adrenoceptor antagonist Medicaments
   atenolol (TENORMIN®)
   butoxamine
   esmolol (BREVIBLOC®)
   labetalol (TRANDATE®, NORMODYNE®)
   metoprolol (LOPRESSOR®)
   nadolol (CORGARD®)
   pindolol (VISKEN®)
   propranolol (INDERAL®)
   timolol (BLOCADREN®)
Adrenergic Neuron Blocking Medicaments
guanethidine (ISMELIN®)
reserpine Cardiovascular System Disorders
   Cardiovascular testing and diagnosis
   Hypertension (HTN)
   Heart Failure
   Ischemic Heart Disease
   Myocardial Infarction
   Arrhythmias
   Isolated Diastolic Heart Failure and Cardiomyopathies
   Cardiac Transplantation
   Venous Thromboembolism
   Stroke
   Hyperlipidemia
   Peripheral vascular disease
   Diuretics
     carbonic-anhydrase inhibitors
     loop diuretics
     osmotic diuretics
     potassium sparing diuretics
     thiazide diuretics
   Anitiarrhythmic Medicaments
     Sodium Channel blocking agents
     isopyramide (NORPACE®)
     flecainide (TAMBOCOR®)
     ibutilide
     lidocaine (XYLOCAINE®)
     mexiletine (MEXITIL®)
     moricizine (ETHMOZINE®)
     procainamide (PRONESTYL®, PROCAN®)
     propafenone (RYTHMOL®)
     quinidine
     tocainide (TONOCARD®)
   Calcium Channel blocking agents
     bepridil (VASOCOR®)
     diltiazem (CARDIZEM®)
     verapamil (ISOPTIN®, CALAN®)
   Adrenergic receptor antagonists
     propranolol (INDERAL®)
   Other medicaments
     adenosine (ADENOCARD®)
     amiodarone (CORDARONE®)
     bretylium (BRETYLOL®)
     disopyramide (NORPACE®)
     esmolol (BREVIBLOC®)
     sotalol (BETAPACE®)
   Hypolipidemic medicaments
     HMG CoA Reductase Inhibitors
       atorvastatin (LIPITOR®)
       cerivistatin (BAYCOL®)
       lovastatin (MEVACOR®)
       pravastatin (PRAVOCHOL®)
       simvastatin (ZOCOR®)
   Bile-acid sequestrants
     cholestyramine (QUESTRAN®)
     colestipol (COLESTID®)
   Fibric acids
     clofilbrate
     fenofibrate (TRICOR®)
     gemfibrozil (LOPID®)
     niacin, nicotinic acid
     probucol (LORELCO®)

Antihypertensive Medicaments
   Adrenergic receptor antagonists
     acebutalol (SECTRAL®)
     atenolol (TENORMIN®)
     betaxolol (BETOPTIC®)
     bisoprolol (ZEBETA®)
     carteolol (CARTROL®)
     clonidine (CATAPRES®)
     labetalcl (NORMODYNE®)
     metoprolol (TOPROL®)
     penbutalol (LEVATOL®)
     pindolol (VISKEN®)
     prazosin (MINIPRES®)
     propranolol (INDERAL®)
     terazosin (HYTRIN®)
     timolol (TIMOPTIC®)
   Calcium Channel Antagonists
     amlodipine (NORVASC®)
     diltiazem (CARDIZEM®)
     felodipine (Plendil)
     isradipine (DYNACIRC®)
     nicardipine (CARDENE®)
     nifedipine (PROCARDIA®)
     nimodipine (NIMOTOP®)
     nisoldipine (SULAR®)
     verapamil (ISOPTIN®, CATAN®)
   Angiotensin Converting Enzyme (ACE) Inhibitor
     benazepril (LOTENSIN®)
     bepridil (VASCOR®)
     captopril (CAPOTEN®)
     enalapril (VASOTEC®)
     fosinopril (MONOPRIL®)
     lisinopril (PRINIVIL®, ZESTRIL®)
     moexipril (UNIVASC®)

quinapril (ACCUPRIL®)
ramipril (ALTACE®)
Angiotensin II Receptor Antagonists
　losartan (COZAAR®)
　valasartan (DIOVAN®)
Diuretics
　amiloride (MIDAMOR®)
　bumetanide (BUMEX®)
　chlorothalidone (HYGROTON®)
　ethacrynic acid (EDECRIN®)
　furosemide (LASIX®)
　hydrochlorothiazide (DIURIL®)
　indapamide (LOZOL®)
　metolazone (ZAROXOLYN®)
　torsemide (DEMADEX®)
　triamterene
Other Agents
　hydralazine (APRESOLINE®)
　minoxidil (ROGAINE®)
　nitroprusside (NIPRIDE®)
　prazosin (MINIPRES®)
　reserpine
　sotalol (BREVIBLOC®)
　spironolactone (ALDACTONE®)
　terazosin (HYTRIN®)
Antianginal medicaments
　Organic nitrates
　Calcium Channel Antagonists
　Adrenergic Receptor Antagonists
　amyl nitrite
　erythrityl tetranitrate
　isosorbide dinitrate (ISORDIL®)
　nitroglycerin
　pentaerythritol tetranitrate
Congestive Heart Failure Medicaments
　phosphodiesterase (PDE) inhibitors
　　amrinone (INOCOR®)
　　milrinone (PRIMACOR®)
　carvedilol (COREG®)
　cardiac glycosides
　　digitoxin
　　digoxin
　diuretics
　ACE Inhibitors
　Dobutamine
　dopamine Respiratory System Disorders
　Asthma
　Chronic Obstructive Lung Disease (COLD)/Chronic Obstructive Pulmonary Disease (COPD)
　Acute Respiratory Distress Syndrome (ARDS)
　Drug-Induced Pulmonary Disease
　Cystic Fibrosis
　Corticosteroids
　　beclomethasone
　　betamethasone
　　cortisone
　　dexamethasone
　　fluticasone (FLOVENT®/FLONASE®)
　　hydrocortisone
　　methylprednisolone
　　prednisolone
　　prednisone
　　triamcinolone
　sympathomimetics
　　albuterol (PROVENTIL®/VENTOLIN®)
　　salmeterol (SEREVENT®)
　muscarinic antagonists
　　ipratropium (COMBIVENT®)
　leukotriene pathway inhibitors
　　montelukast (SINGULAIR®)
　　zafirtukast (ACCOLATE®)
　mast cell stabilizers
　　cromolyn (INTAL®)
　methylxanthines
　　theophylline
　　aminophylline
　Dnase (Pulmozyme)

Gastrointestinal System Disorders
　Gastro-esophageal Reflux Disease (GERD)
　Peptic Ulcer Disease
　Inflammatory Bowel Disease
　Nausea and Vomiting
　Diarrhea, Constipation, Irritable Bowel Disease (IBD)
　Portal Hypertension and Cirrhosis
　Drug-Induced Liver Disease
　Pancreatitis
　Viral Hepatitis
　Liver Transplantation
　Histamine-2 receptor antagonists
　　famotidine (PEPCID®)
　　nizatidine (AXID®)
　　pantoprazole (PROTONIX®)
　　rabeprazole (ACIPHEX®)
　　ranitidine (ZANTAC®)
　Proton Pump Inhibitors (PPIs)
　　esomeprazole (NEXIUM®)
　　lansoprazole (PREVACID®)
　　omeprazole (PRILOSEC®)
　Anti-nausea/anti-vertigo medicaments
　　anticholinergics
　　antihistamines (Histamine-1 receptor antagonists)
　　dopamine antagonists
　　prokinetic gastric stimulant
　　serotonin 5HT$_3$ receptor antagonists
　　　dolasetron (ANZMET®)
　　　granisetron (KYTRIL®)
　　　ondansetron (ZOFRAN®)
　　other medicaments
　　　hydroxyzine (ATARAX®, VISTARIL®)
　　　corticosteroids
　　　benzodiazepines
　　　cannabinoids
　Prokinetic gastric stimulants (gastric motility stimulants)
　　cisapride (PROPULSID®)
　　metoclopramide (REGLAN®)
　Laxatives
　　Saline laxatives
　　magnesium salts
　　sodium salts
　irritant/stimulant medicaments
　　cascara
　　senna
　　phenolphthalein
　　bisacodyl
　　casanthranol
　　castor oil bulk-producing medicaments
  methylcellulose
  psyllium
  polycarbophil
lubricant
  mineral oil
surfactants
  docusate
miscellaneous
  glycerin
    lactulose
Anti-diarrheal medicaments
  diphenoxylate
  atropine
  diphenoxin
  loperamide
  bismuth
  lactobacillus
Ulcerative Colitis Medicaments
  mesalamine
  olsalazine Renal System Disorders
  Acute Renal Failure
  Progressive Renal Failure/Chronic Renal Failure Neurologic System Disorders
  Multiple Sclerosis and inflammatory polyneuropathies
  Epilepsy
  Parkinson's disease and Movement Disorders
  Pain management
  Headache
  Amyotrophic Lateral Sclerosis
  Anti-epileptic medicaments
    carbamazepine (TEGRETOL®)
    divalproex sodium (DEPAKOTE®)
    felbamate (Felbatol FELBATOL®)
    gabapentin (NEURONTIN®)
    lamotrigine (LAMICTAL®)
    oxcarbazepine (TRILEPTAL®)
    phenytoin (DILANTIN®)
    topiramate (TOPAMAX®)
    zonisamide (ZONEGRAN®)
  Antimigraine medicaments
    Serotonin $5HT_1d$ receptor agonists
      almotriptan (AXERT®)
      frovatriptan (FROVA®)
      naratriptan (AMERGE®)
      rizatriptan (RIZALT®)
      sumatriptan (IMITREX®)
      zolmitriptan (ZOMIG®)
    ergot alkaloids
      dihydroergotamine (DHE®)
      isomethepine/dichlorophenazone (MIDRIN®)
      caffeine
      pizotifen (SANOMIGRAN®)
  Sedative-hypnotic Medicaments
    benzodiazepines
      alprazolam (XANAX®)
      clonazepam (KLORIOPIN®)
      clorazepate (TRANXENE®)
      diazepam (VALIUM®)
      flumazenil (ROMAZICON®)—antagonist
      lorazepam (ATIVAN®)
      midazolam (VERSED®)
      triazolam (HALCION®)
    barbiturates/Anesthetics
      pentobarbital (Nembutal)
      Phenobarbital (Luminal LUMINAL®)
      thiopental (PENTOTHAL®)
    non-depressant anxiolytic
      buspirone (BUSPAR®)
    Treatment of alcoholism
      disulfiram (ANTABUSE®)
  Pain Management Medicaments
    Opioids
      Opioid Peptides
        beta-endorphin
        dynorphin
        enkephalins
      Agonists
        codeine
        etorphine
        fentanyl (SUBLIMAZE®)
        hydrocodeine
        hydromorphone
        meperidine (DEMEROL®)
        methadone (DOLOPHINE®)
        morphine
        oxycodone
        propoxyphene
      Agonist-antagonists
        buprenorphine
      Partial Agonist
        dezocine (DALGAN®)
        nalbuphine (NUBAIN®)
        pentazocine (TALWAIN®)
      Antagonist
        naloxone (NARCAN®)
    Non-opiate
      acetaminophen (TYLENOL®)
      tramadol (ULTRAM®)
  Anti-Parkinsonism Medicaments
    levodopa
    carbidopa
    bromocriptine (PARLODEL®)
    pergolide (PERMAX®)
    amantadine (SYMMETREL®)
    selegiline (DEPRENYL®)
    anticholinergic agents
    dopamine Agonists
      pramipexole (MIRAPEX®)
      ropinirole (REQUIP®)
    COMT inhibitors
      entacapone (COMTAN®)
      tolcapone (TASMAR®)
  Anti-Spasticity Medicaments
    baclofen (LIORESAL®)
    botulinum toxin type A (BOTOX®)
    carisoprodol (SOMA®, RELA®)
    chlorphenesin (Maolate MAOLATE®)
    chlorzoxazone (PARAFLEX®)
    cyclobenzaprine (FLEXERIL®)
    dantrolene (DANTRIUM®)
    diazepam (VALIUM®)
    metaxalone (SKELAXIN®)
    methocarbamol (ROBAXIN®)
    orphenadrine (NOR-FLEX®)
    tizanidine (ZANAFLEX®)

Psychiatric System Disorders
  Childhood psychiatric disorders
    Attention Deficit Hyperactivity Disorder (ADHD)/Attention Deficit Disorder (ADD)
  Eating disorders
  Alzheimer's disease and Dementia Disorders
  Substance abuse and Addictive Disorders
    alcohol, tobacco and caffeine abuse
  Schizophrenia
  Depressive disorders
  Bipolar disorders
  Anxiety disorders
  Obsessive-Compulsive disorders
  Sleep disorders
  Psychostimulant Medicaments
    amphetamine mixed salts (ADDERALL®)
    dextroamphetamine (DEXEDRINE®)
    methylphenidate (RITALIN®, CONCERTA®)
  Antipsychotic Medicaments (dopamine antagonists)
    Phenothiazine type
      chlorpromazine (THORAZINE®)
      fluphenazine (PROLIXIN®)
    Thioxanthene type
      thiothixene (NAVANE®)
    Butyrophenone type
      haloperidol (HALDOL®)
    Dibenzodiazepine type
      clozapine (CLOZARIL®)
    Thienobenzodiazepine type
      olanzapine (ZYPREXA®)
      quetiapine (SEROQUEL®)
  Antidepressant Medicaments
    Tricyclic antidepressants (TCA's)
      amitriptyline (EVAVIL®, ENDEP®)
      clomipramine (ANAFRANIL®), also a SSRI
      desipramine (Norpramin NORPRAMIN®)
      doxepin (SINEQUAN®)
      imipramine (TOFRANIL®)
      maprotiline (LUDIOMIL®)
      nortriptyline (AVENTYL®, PAMELOR®)
      protriptyline (VIVACTIL®)
    Monoamine oxidase inhibitors (MAO-I's)
      clorgyline (specific for MAO type A)
      isocarboxazid (MARPLAN®)
      phenelzine (NARDIL®)
      tranylcypromine (PARNATE®)
    Second Generation Medicaments (not including SSRIs)
      amoxapine (ASENDIN®)
      bupropion (WELLBUTRIN®)
      netazodone (SERZONE®)
      trazodone (DESYREL®)
    Serotonin-Specific Reuptake Inhibitors (SSRIs)
      citalopram (CELEXA®)
      clomipramine (ANAFRANIL®)
      escitalopram (LEXAPRO®)
      fluoxetine (PROZAC®)
      fluvoxamine (LUVOX®)
      paroxetine (PAXIL®)
      sertraline (ZOLOFT®)
    Other
      lithium
      mirtazapine (TEMERON®)
      venlafaxine (EFFEXOR®)
  Anti-anxiety agents
    barbiturates
    benzodiazepines
    buspirone (BUSPAR®) chloral hydrate
    doxepin
    hydroxyzine
    sedative-hypnotics
    serotonin reuptake inhibitors
  Anti-demential Medicaments
    cholinesterase inhibitors
      donepezil (ARICEPT®)
      galantamine (REMINYL®)
      rivastigmine (EXELON®)
      tacrine (COGNEX®)
Endocrinologic System Disorders
  Diabetes mellitus
  Thyroid disorders
  Adrenal Gland disorders
  Pituitary Gland disorders
  ACTH
  Adrenal androgens
  Adrenocortical Function Antagonists
  Mineralocorticoid antagonists
  Anti-Diabetic Medicaments
    Insulin
    Sulfonylureas
      acetohexamide (DYMELOR®)
      chlorpropamide (DIABINESE®)
      glimepiride (AMARYL®)
      glipizide (GLUCOTROL®)
      glyburide (MICRONASE®, DIABETA®)
      tolazamide (TOLINASE®)
      tolbutamide (ORINASE®)
    Biguanides
      metformin (GLUCOPHAGE®)
    Alpha-glucosidase Inhibitors
      acarbose (PRECOSE®)
      miglitol (GLYSET®)
    Thiazolidinedione Derivatives
      pioglitazone (ACTOS®)
      rosiglitazone (AVANDIA®)
      troglitazone (REZULIN®)
  Thyroid Disorder Medicaments
    Levothyroxine
    Liothyronine
    Liotrix
  Hypothalamic and Pituitary Gland Medicaments
    bromocriptine (PARLODEL®)
    chorionic gonadotropin (hCG®)
    corticotropin generic (ACTH®)
    cosyntropin (CORTROSYN®)
    desmopressin (DDAVP®)
    gonadorelin acetate (GnRH) (LUTREPULSE®)
    gonadorelin hydrochloride (GnRH) (FACTREL®)
    goserelin acetate (ZOLADEX®)
    growth hormone
    histrelin (SUPPRELIN®)
    leuprolide (LUPRON®)
    menotropins (hMG) (PERGONAL®, HUMEGON®)
    natarelin (SYNAREL®)
    octreotide (SANDOSTATIN®)
    oxytocin (PITOCINIT®, SYNTOCINON®)
    pergolide (PERMAX®)
    protirelin (THYPINONE®, RELEFACT TRH®)
    sermorelin (GHRH) (GEREF®)
    somatrem (PROTROPIN®)
    somatropin (HUMATROPE®, NUTROPIN®)
    thyrotropin (TSH) (THYTROPAR®)
    urofollitropin (METRODIN®)
    vasopressin (Pitressin Synthetic)

Gynecologic System and Obstetric Conditions
  Pregnancy and Lactation
  Infertility
  Contraception
  Menstruation-related disorders
  Endometriosis
  Hormone Replacement Therapy (HRT)
  Conjugated estrogens (PREMARIN®)
  desogestrel
  di-norgestrel
  ethinyl diacetate
  ethinyl estradiol
  levonorgestrel
  medroxyprogesterone
  norethindrone norgestimate
  progesterone Urologic System Disorders
  Erectile Dysfunction
  Benign Prostatic Hypertrophy
  Urinary Incontinence
  apomorphine
  alprostadit
  phosphodiesterase (PDE-5) inhibitors
    sildenafil (VIAGRA®)
    tadalafil (CIALIS®)
    vardenafil (LEVITRA®)
  tolterodine (DETROL®)
  tamulosin (FLOMAX®)
  yohimbine Immunologic System Disorders
  Systemic Lupus Erythematosus and other Collagen-vascular diseases
  Allergic and pseudo-allergic drug reactions Bone and Joint System Disorders
  Osteoporosis and Osteomalacia
  Rheumatoid Arthritis
  Osteoarthritis
  Gout and hyperuricemia
  Medicaments used in the Control of Inflammation
    Non-steroidal anti-inflammatory drugs (NSAIDs) aspirin
    diclofenac (CATAFLAM®, VOLTAREN®)
    diflusnisal (DOLOBID®)
    etodolac (LODINE®)
    fenoprofen (NALFON®)
    flubiprofen (ANSAID®)
    ibuprofen (MOTRIN®, ADVIL®, NUPRIN®)
    indomethacin (INDOCIN®)
    ketoprofen (ORUDIS®)
    ketorolac (TORADOL®)
    meclofenamate
    nabumetone (RELAFEN®)
    naproxen (NAPROSYN®)
    oxaprozin (DAYPRO®)
    phenylbutazone
    piroxicam (FELDENE®)
    salicytate
    sulindac (CLINORIL®)
    tolmetin (TOLECTIN®)
  Cyclocxygenase-2 inhibitors (COX-2)
    celecoxib (CELEBREX®)
    rofecoxib (VIOXX®)
  Arthritis and Gout Medicaments
    allopurinol
    anti-malarial compounds
      chloroquine
    colchicine
    enbrel
    Glucocorticoids
    Gold
    methotrexate
    NSAIDs
    Penicillamine
  Other Medicaments
    alendronate (FOSAMAX®)
    raloxifene (EVISTA®)

Disorders of the Eyes, Ears, Nose, and Throat Systems
  Glaucoma
  Allergic rhinitis
    Histamine-1 receptor antagonists
      brompheniramine (DIMETANE®)
      cetirizine (ZYRTEC®)
      chlorpheniramine (CHLOR-TRIMETON®)
      clemastine (TAVIST®)
      cyproheptadine (PERIACTIN®)
      dimenhydrinate (DRAMAMINE®)
      diphenhydramine (BENDARYL®)
      doxylamine (SOMINEX®, UNISOM®)
      fexofenadine (ALLEGRA®)
      loratidine (CLARITIN®)
    Sympathomimetic medicaments
      pseudoephedrine (Sudated)

Dermatologic System Disorders
  Acne
  Psoriasis
  Rosacea and pigmentation disorders Hematologic System Disorders
  Hematopoeisis
  Anemias
  Coagulation disorders
  Sickle-cell anemia
  Drug-induced hematologic disorders
  Coagulation disorders Medicaments
    aspirin
    clopidogrel (PLAVIX®)
    fibrinolytic inhibitors
    fibrinolytics
    glycoprotein (GP) IIb/IIIa antagonists/monoclonal antibodies
      abciximab (REOPRO®)
      eptifibatide (INTEGRELIN®)
      tiofibran (AGGRASTAT®)
    heparin
    low-molecular weight heparins
    Plasma fractions—blood factors
    ticlopidine (TICLID®)
    vitamin K
    warfarin (COUMADIN®)

Infectious System Diseases
  Central Nervous System (CNS) infections
  Lower Respiratory Tract Infections
  Upper Respiratory Tract Infections
  Skin and Soft Tissue Infections
  Infective Endocarditis
  Tuberculosis
  Gastrointestinal Infections and Enterotoxigenic poisonings Intra-abdominal Infections
Parasitic diseases
Urinary Tract Infections and Prostatis
Sexually Transmitted Diseases
Bone and Joint Infections
Sepsis and Septic Shock
Superficial Fungal Infections
Invasive Fungal Infections
Infections in Immunocompromised Patients
Antimicrobial prophylaxis in Surgery
Vaccines, toxoids, and other immunobiologics
Human Immunodeficiency Virus Infection
Medicaments Used in Infectious Diseases
Cell Wall Synthesis Inhibitors
   Penicillins
      amoxicillin (AMOXIL POLYMOX®)
      ampicillin (PRINCIPEN®, OMNIPEN®)
      benzathine Penicillin G
      benzyl Penicillin (PENICILLIN G®)
      carbenicillin (GEOCILLIN®)
      cloxacillin (CLOXAPEN®)
      dicloxacillin (DYNAPEN®)
      methicillin (STAPHCILLIN®)
      mezlocillin
      nafcillin (NAFCIL®, UNIPEN®)
      oxacillin
      phenoxymethyl Penicillin (PENICILLIN V®)
      piperacillin (PIPRACH®)
      ticarcillin (TICAR®)
Cephalosporins
   1st generation:
      cefazolin (ANCEF®, DEFZOL®)
      cephalexin (KEFLEX®)
      cephatothin (KEFLIN®)
   2nd generation:
      cefaclor (CECLOR®)
      cefoxitin (MEFOXIN®)
      cefpodoxime (VANTIN®)
      cefuroxime (ZINACEF®, CEFTIN®)
      loracarbef (LORABID®)
   3rd generation:
      cefoperazone
      cefotaxime (CLAFORAN®)
      cefotetan
      ceftazidime (FORTAX®, TAXIDIME®, TAZICEF®)
      ceftriaxone (ROCEPHIN®)
      veftizoxime (CEFIZOX®)
   4th generation:
      cefepime
Other beta-Lactams aztreonam (AZACTAN®)
   clavulanic acid
   imipenem (PRIMAXIN®)
   meropenem (MERREM IV®)
   sulbactam
Other Cell-Wall Synthesis Inhibitors bacitracin
   cycloserine
   fosfomycin (MONUROL®)
   vancomycin (VANCOCIN®)
Agents Which Affect Cell Membranes
   Polymixins
      Colistimethate
      Potymyxin B
Protein Synthesis Inhibitors
   Aminoglycosides
      amikacin (AMIKIN®)
      gentamicin (GARAMYCIN®)
      kanamycin (KANTREX®)
      neomycin
      netilmicin (NETROMYCIN®)
      streptomycin
      tobramycin
   Tetracyclines
      demeclocycline (DECLOMYCIN®)
      doxycycline
      doxycyclmne (VIBRAMYCIN®, DORYX®)
      tetracycline (ACHROMYCIN®)
   Macrolides
      azithromycin (ZITHROMAX®)
      clarithromycin (BIAXIN®)
      erythromycin esters erythromycin
   Other Protein Synthesis Inhibitors
      Chloramphenicol (CHLOROMYCETIN®)
      Clindamycin (CLEOCIN®)
      Spectinomycin (TROBICIN®)
Inhibitors of Folate-Dependent Pathways
   co-trimoxazole
   silver Sulfadiazine
   sodium Sulfacetamide
   sulfamethoxazole (GANTANOL®)
   sulfasalazine (AZULFIDINE®) (SALICYLAZO-SULFAPYRIDINE®)
   sulfisoxazole (GANTRISIN®)
   sulfonamides
Dihydrofolate Reductase Inhibitor
   trimethoprim
DNA Gyrase Inhibitors
   ciprofloxacin (CIPRO®)
   gatifloxacin (TEQUIN®)
   levofloxacin (LEVAQUIN®)
   lomefloxacin (MAXAQUIN®)
   nalidixic acid
   ofloxacin (FLOXIN®)
Urinary Tract Antiseptics
   nitrolurantoin
Antimyobacterial Agents
   First-line anti-TB medicaments
      ethambutol
      isoniazid (INI-I®)
      pyrazinamide
      rifampin (RIMACTANE®)
      streptomycin
   Second-line anti-TB medicaments
      capreomycinA
      cycloserine
      dapsone
      ethionamide
      para-aminosalicylic acid
AntiFungal Agents
   amphotericin B (FUNGIZONE®, AMPHOTEC®)
   clotrimazole (MYCELEX®)
   fluconazole (DIFLUCAN®)
   flucytosine
   griseofulvin
   itraconazole (SPORANOX®)
   ketoconazole (NIZORAL®)
   miconazole (MONISTAT®)
   nystatin (MYCOSTATIN®)
AntiParasitic Agents
   Antimalarials
      chloroquine (ARALEN®)
      mefloquine (LARIAM®)
      primaquine
      pyrimethamine-sulfadoxine (FANSIDAR®)

Anti protozoals
  metronidazole (FLAGYL®)
  pentamidine isethionate
  pyrimethamine-sulfonamide
  trimethoprim (generic) sulfamethoxazole (GANTANOL®)
Antihelminthic Medicaments
  mebendazole
  praziquantel (BILTRICIDE®)
  pyrantel pamoate
  thiabendazole (MINTEZOL®)
Antiviral Medicaments
  acyclovir (ZOVIRAX®)
  didanosine (DDI®)
  foscarnet (FOSCAVIR®)
  ganciclovir (DHPG®, CYTOVENE®)
  ribavirin
  rimantadine
  stavudine (d4T))
  valacyclovir (VALTREX®)
  vidarabine (VIRA-A®)
  zalcitabine (DDC®)
  zidovudine (AZIDOTHYMIDINE®, AZT®)
  Protease inhibitors
    indinavir (CRIXIVAN®)
    ritonavir (NORVIR®)
    saquinavir (FORTOVASE®)

Oncologic and Immunological Disorders
  Breast Cancer
  Lung Cancer
  Colorectal Cancer
  Prostate Cancer
  Malignant Lymphomas
  Ovarian Cancer
  Acute Leukemias
  Chronic Leukemias
  Melanoma and other Skin Cancers
  Hematopoeitic Stem Cell Transplantation
  Anti-neoplastic Medicaments
    Alkylating Agents
      busulfan (MYLERAN®)
      carboplatin (PARAPLATIN®)
      carmustine (BNCU®, BiCNU®)
      cisplatin (PLATINOL®)
      cyclophosphamide (CYTOXAN®)
      ifofamide (IFEX®)
      lomustine (CCNU®, CeeNU®)
      mechlorethamine (MUSTARGEN®)
      meiphalan (ALKERAN®)
      procarbazine (MATULANE®)
      thiotepa
    Antimetabolites
      folic acid Antagonist
        methotrexate
    Purine Antagonists 6-mercaptopurine
      6-thioguanine
    Pyrimidine Antagonists
      cytarabine (ARA-C®)
      fluorouracil (5-FU®)
    Hormonal Agents Hormones
      diethylstilbestrol (DES®)
      estrogens
      prednisone (DELTASONE®)
    Modulation of Hormone Release & Action Aminoglutethimide
      leuprolide acetate
      tamoxifen (NOLVADEX®)
    Plant Alkaloids
      Vinca Alkaloids
        vinblastine (VELBAN®)
        vincristine (Oncovin ONCOVIN®)
      Podophyllotoxins
        Etoposide (VP-16®)
      Other
        docetaxel (TAXOTERE®)
        paclitaxel (TAXOL®)
    Antibiotics
      bleomycin (BLENOXANE®)
      dactinomycin (COSMEGEN®)
      daunorubicin (DAUNOXOME®)
      doxorubicin (ADRIAMYCIN®)
      mitomycin (MUTAMYCIN®)
    Other Anti-neoplastic Medicaments
      amsacrine (AMSA®)
      azathioprine (IMURAN®)
      capecitabine (XELODA®)
      chlorambucil (LEUKERAN®)
      cyclosporine (SANDIMMUNE®, NEORAL®)
      gemcitabine (GEMZAR®)
      hydroxyurea (HYDREA®)
      mitotane (SODREN®)
      mitoxantrone (NOVANTRONE®)
      pamidronate (AREDIA®)
  Immunosuppressant Medicaments
    15-desoxyspergualin
    corticosteroids
    cyclosporine
    Interferons
    Interleukins
    mycophenolate mofetil
    sirolimus (RAPAMYCIN®)
    tacrolimus
    thalidomide
Nutritional Disorders
Malnutrition, vitamin and mineral deficiencies
Enteral Nutrition
Obesity
  orlistat (XENICAL®)
  appetite suppressants
  sympathomimetic stimulants
  amphetamine stimulants
Mineral supplementation
  calcium ion iodine
  iron
  magnesium ion
  phosphorous
  potassium ion
  selenium
  sodium ion
  zinc
Fat-soluble vitamins
  vitamin A
  vitamin D
  vitamin E
  vitamin K
Water-soluble vitamins
  vitamin C
  thiamine (vitamin B1)
  riboflavin (vitamin B2)
  niacin (vitamin B3)

pyridoxine (vitamin B6)
folate
cyanocobalamin (vitamin B12)

Medicaments Used to Alleviate Symptoms of Allergic Rhinitis, Upper Respiratory Symptoms, Cough, Mild Aches and Pains
  Nasal Decongestants
    ephedrine
    phenylephrine
    phenylpropanolamine
    pseudoephedrine
  Antihistamines (Histamine-1 receptor antagonists)
  Antitussive agents
    benzonatate
    codeine
    dextromethorphan
  Expectorants
    guaifenesin
    iodinated glycerol
    terpin hydrate
  Xanthines
    aminophylline
    caffeine
    dyphylline
    theophylline
  Pain relievers
    narcotic agonists
    NSAIDS
    acetaminophen Dietary Supplements
  Arnica
  Bilberry
  Black Cohosh
  Cat's claw
  Chamomile
  Echinacea
  Evening Primrose Oil
  Fenugreek
  Flaxseed
  Feverfew
  Garlic
  Ginger root
  Ginkobiloba
  Ginseng
  Goldenrod
  Hawthorn
  Kava-Kava
  Licorice
  Milk thistle
  Psyllium
  Rauwolfia
  Senna
  Soybean
  St. John's wort
  Saw palmetto
  Turmeric
  Valerian Therapeutic Proteins and Biotechnology Medicaments Additional Agents: NORVACS®, NEURONTIN®, PAXIL®, AUGMENTIN®, PROPECIA®, LAMISIL®, LESCOL®, bisphosphonate.

Other Drugs abacavir sulfate
acetazolamide
acetylsalicylic acid
albendazole
allopurinol
amiloride hydrochloride
amitriptyline hydrochloride artemether
atropine sulfate
benznidazole
biperiden hydrochloride
chloroquine phosphate
chlorpheniramine maleate
chlorpromazine hydrochloride
cimetidine
ciprofloxacin hydrochloride
clofazimine
clomiphene citrate
clomipramine hydrochloride
cloxacillin sodium
codeine phosphate
dapsone
didanosine
diethylcarbamazine citrate
digoxin
diloxanide furoate
DL-methionine
Doxycycline
Efavirenz
ergometrine maleate
ergotamine tartrate
erythromycin ethyl succinate
ethambutol hydrochloride
ethosuximide
ferrous sulfate Examples XII As can be seen above, various embodiments of the present invention can be utilized in specific medical applications. By way of example only and not by way of limitation, the present invention can be practiced to prepare delivery devices for use in chemotherapy to address/treat, by way of example and not by limitation, the following aspects of chemotherapy: psychological, timing (to coincide with tumor growth for example) route of administration, nausea, vomiting (CINV), compliance, and cost (e.g. reduce hospital management of patients, reduce the number of "repeat" drug doses due to patient vomiting, etc.). Still further, the just mentioned aspects are not limited to chemotherapy, as the present invention can be practiced to address common aspects between chemotherapy and other treatments.

Further by way of examples, capsules containing ZOFRAN® (ondansertron), TEMODAR® (temozolomide) can be made.

Still further, the present invention can be used in cardiovascular treatments, for example hypertension, heart failure, and heart rhythm disorders. Also, the present invention can be used in immunology (e.g. transplant rejections, auto-immune disorders, etc.). The present invention can be used to treat neurological disorders (such as Parkinson's disease, dementia, stroke, epilepsy, and migraine headache, etc.), psychiatric disorders (schizophrenia, bipolar disease, depression, anxiety, ADHD/ADD, Addictions, etc.), infectious diseases (fungal, bacterial, viral (HIV), etc.), and in anesthesiology (induction anesthesia, local anesthesia). Furthermore, the present invention has application in endocrinology (cholesterol, diabetes, hormone replacement therapy, thyroid dysfunction, oral contraception, obesity, etc.), dermatology (onychomycosis, acne, rosaceae, psoriasis, etc.), rheumatology (arthritis, gout, osteoporosis/Osteomalacia), respiratory fields (asthma, emphysema, cystic fibrosis, etc.), gastro-intestinal fields (gastro-esophageal reflux disease, ulcer prophylaxis, crohn's disease, inflammatory bowel disease, etc.), chronic renal failure (vitamin and mineral replacement, blood pressure regulation, diabetes, depression, etc.), genito-urinary (enlarged prostate/BPH, overactive bladder, erectile dysfunction, feminine yeast infections, etc.) and hematology-oncology (thromboembolous, hermatopoeisis, neoplastic disease, nausea/vomiting).

Examples XIII

The present invention can be utilized with a variety of exipients. Categories of exipients include, but are not limited to, Binders, Disintegrants Fillers (diluents), Lubricants, Glidants (flow enhancers), Compression aids, Colors, Sweeteners, Preservatives, Suspending/dispersing agents, Film formers/coatings, Flavors, and Printing inks. Still further by way of example and not by limitation, the present invention can be utilized with the following exipients:

| | |
|---|---|
| Magnesium Stearate | Povidone |
| Lactose | Pregelatinized Starch |
| Microcrystalline Cellulose | Hydroxy Propyl Methylcellulose |
| Starch (corn) | OPA products (coatings & inks) |
| Silicon Dioxide | |
| Titanium Dioxide | Croscarmellose |
| Stearic Acid | Hydroxy Propyl Cellulose |
| Sodium Starch Glycolate | Ethylcellulose |
| Gelatin | Calcium Phosphate (dibasic) |
| Talc | Crospovidone |
| Sucrose | Shellac (and Glaze) |
| Calcium Stearate | |

Examples XIV

Examples of the supporting nutraceutical formulations are to illustrate examples where specific categories of the natural products industry can be utilized with the present invention. There are many more categories than the ones that are listed and therefore this is for simply for the purpose to show that the technology is broad and could be utilized for many specific categories. The specific mg of each product is not included due to the amounts of each material is typically based upon the formulators opinions, however there are some (RDA) recommended daily allowances that could be used to determine the formulation.

Category: Antioxidant

Primary Capsule:
   d alpha Tocopherol
   Beta Carotene
   Tocotrineol
   Grape Seed Oil Secondary Capsule:
   Selenium
   Vitamin C Ester Category: Brain Support Primary Capsule:
   d alpha Tocopherol
   DHA
   Omega 3
   Lecithin
   Choline Secondary Capsule:
   Coenzyme Q 10
   Ginkgo Biloba
   B 12

Category: Mood Support

Primary Capsule:
   D alpha Tocopherol
   Lecithin
   DHA
   Omega 3

Secondary Capsule:
   SAME
   L Tyrosine

Category: Cardio Support

Primary Capsule:
   d alpha Tocopherol
   Tocotrienol
   Flax Oil Omega 6
   Fish Oil Omega 3

Secondary Capsule:
   Calcium
   Magnesium
   Coenzyme Q 10

Category: Diet Support

Primary Capsule:
   Cojugated Linolic Acid
   Flax Seed Oil

Secondary Capsule:
   Chromium
   Zinc
   L Carnitine

Category: Immune Support

Primary Capsule:
   Garlic Oil
   Olive Leaf Oil
   d alpha Tocopherol

Secondary Capsule:
   Zinc
   Echinacea

Category: Laxative Support

Primary Capsule:
  Aloe Vera
  Flax Seed Oil

Secondary Capsule:
  Senna Leaf
  Psyllium

Category: Prostate Support

Primary Capsule:
  Saw Palmetto Oil
  Pygeum Oil
  Flaxseed Oil
  Pumpkin Seed Oil Secondary Capsule:
  Selenium
  Zinc
  Boswellia Serrata Category: Inflammation Support Primary Capsule:
  Boswellia Serrata Oil
  Guggul Oil
  Omega 3 Oil
  Ginger Oil Secondary Capsule:
  Curcumin
  Holy Basil Category: Sports Nutrition/Muscle Support Primary Capsule:
  Cojugated Linolic Acid
  MCT Oil Secondary Capsule:
  Zinc
  Chromium
  Tribulus Terrestris
  19 Nor-5-Androstendione Category: Menopause Support Primary Capsule:
  Evening Primrose Oil
  Red Rasberry Oil Secondary Capsule:
  Licorice Root
  Black Cohosh
  Soy Isoflavones Category: Cholesterol Support Primary Capsule:
  Sterol Esters
  Guggul Oil
  d alpha Tocopherol
  Tocotrienol Secondary Capsule:
  Garlic Extract
  Zinc From the above discussion, it will be appreciated that the present invention provides novel integrated capsule delivery apparatus and methods for delivering diverse physical states (e.g., solid, liquid, gas or dispersion) of a single active ingredient or medicament (e.g., pharmaeceutical, biotechnical, nutraceutical, vitamin, dietary supplement, mineral or combination thereof), or a plurality of active ingredients or medicaments, in a single dosage capsular form, wherein at least two of the active ingredients or medicaments if different receiving chambers have physical states that differ. In preferred design, the encapsulation processes and multi-compartment capsular technology of the present invention may include various desirable properties such as, for example, controlling time-release of key active ingredients or medicaments, prolonging shelf-life of the active ingredients or medicaments, improving palatability, reducing overall production costs and reducing the number of capsules consumed by a patient or consumer as nutritional or therapeutic agents.

The present invention provides novel integrated capsule delivery apparatus and methods for delivering a single dosage, multi-compartment capsule comprising a capsular base and cap configuration, wherein the size and shape of the cap, relative to its sealing relationship with the base, generally eliminates or substantially reduces any potential dead space volume within the internal periphery of the capsule, thereby functionally negating the opportunity for reaction between an air bubble and one or more active ingredients introduced into the capsule and, accordingly, improving stability of the capsular ingredient(s).

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A multi-compartment capsule comprising:
  a first receiving chamber comprising at least one oil ingredient in immediate release form, wherein said oil ingredient is selected from the group consisting of a nutraceutical, a vitamin, a dietary supplement; and
  a second receiving chamber containing only solid ingredients and comprising at least one active ingredient in a solid state, formulated in a manner allowing for a time-delayed dissolution and release of said solid active ingredient, wherein said ingredient is selected from the group consisting of a nutraceutical, a vitamin, a dietary supplement and a mineral,
    wherein the ingredients of said first receiving chamber is different from the ingredients of said second receiving chamber, and wherein the multi-compartment capsule is a hard shell capsule.

2. A multi-compartment capsule as defined in claim 1, wherein said first receiving chamber comprises no dead volume space.

3. A multi-compartment capsule as defined in claim 1, wherein said solid active ingredient is selected from the group consisting of a pill, a tablet, a capsule, a powder, granulation, flakes, a troche, a suppository, an ointment, a paste, an emulsion and a cream.

4. A multi-compartment capsule as defined in claim 1, further comprising a third receiving chamber comprising at least one ingredient selected from the group consisting of a nutraceutical, a vitamin, a dietary supplement and a mineral.

5. A multicompartment capsule as defined in claim 1, wherein said first receiving chamber is a primary capsule and said second receiving chamber is a secondary capsule, said primary capsule comprising an internal periphery sufficient for receiving said ingredient and said secondary capsule therein,
wherein the primary and secondary capsules are hard shell capsules.

6. A multi-compartment capsule as defined in claim 5, wherein said primary and said secondary capsules each comprise a base and a corresponding cap, wherein said cap is configured to provide a sealing relationship when engaging said base.

7. A multi-compartment capsule as defined in claim 5, wherein said primary capsule comprises no dead volume space.

8. A multi-compartment capsule as defined in claim 5, wherein said oil ingredient of said primary capsule is a pharmaceutical, wherein said active ingredient of said secondary capsule is a pharmaceutical.

9. A multi-compartment capsule as defined in claim 5, wherein said oil ingredient of said primary capsule and/or said active ingredient of said secondary capsule is a vitamin.

10. A multi-compartment capsule as defined in claim 5, wherein said secondary capsule is received in said primary capsule.

11. A multi-compartment capsule according to claim 1, wherein the second receiving chamber contains Glucosamine/Chondroitin and the first receiving chamber contains Vitamin E.

12. A multi-compartment capsule according to claim 11, wherein the Glucosamine/Chondroitin is in a solid physical state and the Vitamin E is in a liquid physical state.

13. A multi-compartment capsule according to claim 1, wherein the second receiving chamber contains S-adenosylmethionine (SAMe) and the first receiving chamber contains Vitamin E.

14. A multi-compartment capsule according to claim 13, wherein the S-adenosylmethionine (SAMe) is in a solid physical state and the Vitamin E is in a liquid physical state.

15. A multi-compartment capsule according to claim 1, wherein the second receiving chamber contains Curcumin, Holy Basil, Zinc and the first receiving chamber contains Omega 3 Fatty Acids DHA & EPA.

16. A multi-compartment capsule according to claim 15, wherein the Curcumin, Holy Basil, Zinc is in a solid physical state and the Omega 3 Fatty Acids DHA & EPA is in a liquid physical state.

17. A multi-compartment capsule according to claim 1, wherein the second receiving chamber contains Vitamin C and the first receiving chamber contains Vitamin E.

18. A multi-compartment capsule according to claim 1, wherein said ingredient of said first receiving chamber and/or said ingredient of said second receiving chamber is a vitamin.

19. A multi-compartment capsule according to claim 1, wherein said oil ingredient of said first receiving chamber is incompatible with said active ingredient of said second receiving chamber.

20. A multi-compartment capsule according to claim 1, wherein said oil ingredient of said first receiving chamber is pharmaceutically incompatible with said active ingredient of said second receiving chamber.

21. A multi-compartment capsule as defined in claim 1, the multi-compartment capsule provides for stability and sufficient shelf-life of the ingredients to make the multi-compartment capsule fit for human consumption.

22. A multi-compartment capsule as defined in claim 1, wherein said capsule is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, oleoresin, polyvinylacetate, hydroxypropyl methyl cellulose, polymerisates of acrylic or methacrylic esters, polyvinylacetate-phtalate and combinations thereof.

23. A multi-compartment capsule as defined in claim 1, wherein the release of the solid ingredient is delayed by a time-release coating.

24. A multi-compartment capsule as defined in claim 1, wherein said second receiving chamber is enveloped by said first receiving chamber.

25. A multi-compartment capsule as defined in claim 24, wherein the solid active ingredient in the second receiving chamber is caffeine.

26. A multi-compartment capsule as defined in claim 24, wherein the release of the solid ingredient is delayed by a time-release coating.

27. A multi-compartment capsule as defined in claim 26, wherein the second receiving chamber comprises a time-release coating.

28. A multi-compartment capsule as defined in claim 24, wherein the solid ingredient is encapsulated with a time-release coating.

29. A multi-compartment capsule as defined in claim 1, wherein the oil is selected from the group consisting of a herbal oil, a marine oil, a vitamin oil, an extract, and mixtures of any of the foregoing.

30. A multi-compartment capsule, comprising:
a first receiving chamber comprising an active oil ingredient selected from the group consisting of a nutraceutical, a vitamin, and a dietary supplement in immediate release form; and
a second receiving chamber containing only solid ingredients and comprising at least one active ingredient in a solid state and formulated in a manner allowing for a time-delayed dissolution and release of said solid active ingredient, wherein said active ingredient of said first receiving chamber is different from said at least one active ingredient of said second receiving chamber and not present in said second receiving chamber, said second receiving chamber being located within said first receiving chamber, and the multi-compartment capsule is a hard shell capsule.

31. A multi-compartment capsule as defined in claim 30, wherein the release of the solid ingredient is delayed by a time-release coating.

32. A multi-compartment capsule as defined in claim 30, wherein the solid ingredient is encapsulated with a time-release coating.

33. A multi-compartment capsule, comprising:
a first receiving chamber comprising at least one oil in immediate release form; and
a second receiving chamber containing only solid ingredients and comprising at least one active ingredient in a solid state and formulated in a manner allowing for a time-delayed dissolution and release of said solid active ingredient, wherein the ingredients contained in said first receiving chamber are different from the ingredients of said second receiving chamber, and wherein said second receiving chamber is enveloped by said first receiving chamber, and wherein the multi-compartment capsule is a hard shell capsule.

34. A multi-compartment capsule as defined in claim 33, wherein the release of the solid ingredient is delayed by a time-release coating.

35. A multi-compartment capsule as defined in claim 33, wherein the solid ingredient is encapsulated with a time-release coating.

36. A multi-compartment capsule, comprising:
a first receiving chamber comprising at least one active ingredient in an oil in immediate release form; and
a second receiving chamber containing only solid ingredients and comprising at least one active ingredient in a solid state, and means for allowing for a time-delayed dissolution and release of said solid active ingredient,
wherein (A) said active ingredient of said first receiving chamber is different from said active ingredient of said second receiving chamber and not present in said second receiving chamber, and (B) the multi-compartment capsule is a hard shell capsule.

37. A multi-compartment capsule as defined in claim 36, wherein said first receiving chamber comprises no dead space.

38. A multi-compartment capsule as defined in claim 36, further comprising a base and a corresponding cap, wherein said cap is configured to provide, a sealing relationship when engaging said base.

39. A multi-compartment capsule as defined in, claim 38, wherein said cap is configured to reduce dead volume space within said first receiving chamber.

40. A multi-compartment capsule as defined in claim 38, further comprising a filling material introduced into said cap to reduce dead volume space within said first receiving chamber.

41. A multi-compartment capsule as defined in claim 36, wherein said ingredient in said first receiving chamber is selected from the group consisting of a pharmaceutical, a biotechnical, a nutraceutical, a vitamin, a dietary supplement and a mineral.

42. A multi-compartment capsule as defined in claim 41, wherein said ingredient in said second receiving chamber is selected from the group consisting of a pharmaceutical, a biotechnical, a nutraceutical, a vitamin, a dietary supplement and a mineral.

43. A multi-compartment capsule as defined in claim 41, wherein said solid is selected from the group consisting of a pill, a tablet, a powder, granulation, flakes, a troche, and a suppository.

44. A multi-compartment capsule as defined in claim 36, wherein said ingredient in said first receiving chamber comprises a pharmaceutical and said ingredient in said second receiving chamber comprises a pharmaceutical.

45. A multi-compartment capsule as defined in claim 36, wherein said ingredient in said first receiving chamber comprises a pharmaceutical and said ingredient in said second receiving chamber is selected from the group consisting of a biotechnical, a nutraceutical, a vitamin, a dietary supplement and a mineral.

46. A multi-compartment capsule as defined in claim 36, wherein at least one of said receiving chambers comprises a time-release coating.

47. A multi-compartment capsule as defined in claim 36, further comprising a third receiving chamber comprising at least one ingredient.

48. A multi-compartment capsule as defined in claim 47, wherein said ingredient in said third receiving chamber is selected from the group consisting of a pharmaceutical, a biotechnical, a nutraceutical, a vitamin, a dietary supplement and a mineral.

49. A multi-compartment capsule as defined in claim 48, wherein said ingredient in said third receiving chamber is different than the ingredients in said first and said second receiving chamber.

50. A multi-compartment capsule as defined in claim 48 or 49, wherein said ingredient in said third receiving chamber is at a different physical state from the physical states of the ingredients in said first and said second receiving chamber.

51. A multi-compartment capsule as defined in claim 36, wherein the second receiving chamber contains Fluoxetine and the first receiving chamber contains Vitamin E.

52. A multi-compartment capsule as defined in claim 36, wherein the second receiving chamber contains Rofecoxib and the first receiving chamber contains Vitamin E.

53. A multi-compartment capsule as defined in claim 36, wherein the second receiving chamber contains Diphenhydramine Hydrochloride and the first receiving chamber contains Vitamin E.

54. A multi-compartment capsule as defined in claim 36, wherein the second receiving chamber contains Celecoxib and the first receiving chamber contains Ibuprofen.

55. A multi-compartment capsule according to claim 54, wherein the Celecoxib is in a solid physical state and the Ibuprofen is in a liquid physical state.

56. A multi-compartment capsule as defined in claim 36, wherein said active ingredient of said first receiving chamber is a pharmaceutical, and wherein said active ingredient of said second receiving chamber is a pharmaceutical.

57. A multi-compartment capsule as defined in claim 36, wherein said active ingredient of said first receiving chamber and/or said active ingredient of said second receiving chamber is a vitamin.

58. A multi-compartment capsule as defined in claim 36, wherein said active ingredient of said first receiving chamber is incompatible with said active ingredient of said second receiving chamber.

59. A multi-compartment capsule as defined in claim 36, wherein said active ingredient of said first receiving chamber is pharmaceutically incompatible with said active ingredient of said second receiving chamber.

60. The multi-compartment capsule as defined in claim 36, wherein the multi-compartment capsule provides for stability and sufficient shelf-life of the ingredients to make the multi-compartment capsule fit for human consumption.

61. A multi-compartment capsule as defined in claim 36, wherein the means is a time-release coating.

62. A multi-compartment capsule as defined in claim 36, wherein the means is a time-release coating encapsulating the solid ingredient.

63. A multi-compartment capsule as defined in claim 36, wherein the means is a time-release coating encapsulating the solid ingredient.

64. A multi-compartment capsule as defined in claim 36, wherein said capsule is formed of a material selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, oleoresin, polyvinylacetate, hydroxypropyl methyl cellulose, polymerisates of acrylic or methacrylic esters, polyvinylacetate-phtalate and combinations thereof.

65. A multi-compartment capsule as defined in claim 36, wherein said second receiving chamber is enveloped by said first receiving chamber.

66. A multi-compartment capsule as defined in claim 65, wherein the means is a time-release coating.

67. A multi-compartment capsule as defined in claim 65, wherein the means is a time-release coating encapsulating the solid ingredient.

68. A multicompartment capsule as defined in claim 67, wherein the second receiving chamber comprises a time-release coating.

69. A multi-compartment capsule as defined in claim 65, wherein the solid active ingredient in the second receiving chamber is caffeine.

70. A multi-compartment capsule as defined in claim 36, wherein the oil is selected from the group consisting of a herbal oil, a marine oil, a vitamin oil, an extract, and mixtures of any of the foregoing.

71. An encapsulation process for forming a multi-compartment capsule, said process comprising the steps of:
providing a capsule comprising a cap, a base configured having a longitudinally extending body including a length and at least one dividing wall formed along said length of said extending body, said dividing wall adapted to form a first receiving chamber and a second receiving chamber;
introducing into said second receiving chamber only solid ingredients including at least one active ingredient in a solid state, formulated in a manner allowing for a time-delayed dissolution and release of said solid ingredient, wherein said ingredient introduced into said second receiving chamber is selected from the group consisting of a nutraceutical, a vitamin, a dietary supplement and a mineral;
introducing into said first receiving chamber at least one oil ingredient in immediate release form, wherein said oil ingredient introduced into said first receiving chamber is selected from the group consisting of a nutraceutical, a vitamin, and a dietary supplement, wherein the active ingredients of said second receiving chamber are different from the active ingredients of said first receiving chamber; and
positioning said cap in sealing relationship with said base, wherein the multi-compartment capsule is a hard shell capsule.

72. An encapsulation process as defined in claim 71, further comprising the step of reducing dead volume space within said primary capsule.

73. An encapsulation process for forming a multi-compartment capsule, said process comprising the steps of:
providing a primary capsule having a base and a cap;
providing a secondary capsule having a base and a cap;
introducing only solid ingredients including at least one active ingredient in a solid state into said secondary capsule, formulated in a manner allowing for a time-delayed dissolution and release of said solid ingredient;
positioning said cap of said secondary capsule in sealing relationship with said base;
introducing at least one oil ingredient selected from the group consisting of a nutraceutical, a vitamin, and a dietary supplement in immediate release form into said primary capsule, wherein the active ingredients of said secondary capsule are different from the ingredients of said primary capsule;
introducing said secondary capsule into said base of said primary capsule; and positioning said cap of said primary capsule in sealing relationship with said base, wherein the multi-compartment capsule is a hard shell capsule.

74. An encapsulation process as defined in claim 73, further comprising the step of reducing dead volume space within said primary capsule.

75. An encapsulation process as defined in claim 73, further comprising the step of adding a filler material into said secondary capsule selected from the group consisting of gelatin, starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methyl cellulose, oleoresin, polyvinylacetate-phtalate, polymerisates of acrylic or methacrylic esters and combinations thereof.

76. An encapsulation process as defined in claim 73, wherein at least one cap of said capsules comprises a configuration sufficient for reducing dead volume space within the primary capsule.

77. An encapsulation process as defined in claim 73, wherein said ingredient introduced into said primary and secondary capsules is selected from the group consisting of a pharmaceutical, a biotechnical, a nutraceutical, a vitamin, a dietary supplement and a mineral.

78. An encapsulation process as defined in claim 73, wherein said solid is selected from the group consisting of a pill, a tablet, a capsule, a powder, granulation, flakes, a troche, and a suppository.

79. An encapsulation process as defined in claim 73, wherein said oil ingredient in said primary capsule comprises a pharmaceutical and said active ingredient in said secondary capsule is selected from the group consisting of a biotechnical, a nutraceutical, a vitamin, a dietary supplement and a mineral.

80. An encapsulation process as defined in claim 73, wherein said oil ingredient introduced into said primary capsule and said active ingredient in said secondary capsule is a pharmaceutical.

81. An encapsulation process as defined in claim 73, wherein at least one of said capsules comprises a time-release coating.

82. An encapsulation process as defined in claim 73, further comprising the steps of:
providing a tertiary capsule having a base and a cap;
introducing at least one ingredient having a third physical state into said tertiary capsule;
positioning said cap of said secondary capsule in sealing relationship with said base; and
introducing said tertiary capsule into said base of said secondary capsule.

83. An encapsulation process as defined in claim 82, wherein said ingredient in said tertiary capsule is selected from the group consisting of a pharmaceutical, a biotechnical, a nutraceutical, a vitamin, a dietary supplement and a mineral.

84. An encapsulation process as defined in claim 83, wherein said ingredient in said tertiary capsule is different from the other ingredients of the other capsules.

85. An encapsulation process as defined in claim 83 or 84, wherein the ingredients are pharmaceuticals.

86. An encapsulation process as defined in claim 82, wherein said tertiary capsule comprises a time-release coating.

87. An encapsulation process as defined in claim 73 or claim 82, wherein at least one of said capsules further comprise a soft elastic capsule formed of a material selected from the group consisting of glycerin and sorbitol.

88. An encapsulation process as defined in claim 87, wherein said soft elastic capsule includes an antimicrobial selected from the group consisting of paraben and sorbic acid.

89. An encapsulation process as defined in claim 73, wherein said ingredient introduced in said primary capsule comprises a moisture content in the range of about 0% to 6% by weight.

90. An encapsulation process as defined in claim 73, wherein said primary and secondary capsules contain at least one pharmaceutically acceptable lubricant in the range of about 0% to 10% by weight.

91. An encapsulation process as defined in claim 90, wherein said lubricant is selected from the group consisting of aluminiumstearate, calciumstearate, magnesiumstearate, tinstearate, talc, sodium lauryl sulfate, lecithins, mineral oils, stearic acid, silicones and combinations thereof.

92. An encapsulation process as defined in claim 73, wherein said oil ingredient of said secondary capsule is a pharmaceutical, wherein said active ingredient of said primary capsule is a pharmaceutical.

93. An encapsulation process as defined in claim 73, wherein said active ingredient of said secondary capsule and/or said oil ingredient of said primary capsule is a vitamin.

94. An encapsulation process for forming a multi-compartment capsule, said process comprising the steps of:
   providing a capsule comprising a cap, a base configured having a longitudinally extending body including a length and at least one dividing wall formed along said length of said extending body, said dividing wall adapted to form a first receiving chamber and a second receiving chamber;
   introducing only solid ingredients including at least one non-excipient ingredient in a solid state into said second receiving chamber, formulated in a manner allowing for a time-delayed dissolution and release of said solid ingredient;
   introducing at least one non-excipient oil ingredient into said first receiving chamber in immediate release form, wherein said non-excipient ingredients of said second receiving chamber are different from the non-excipient ingredients of said first receiving chamber and not present in said first receiving chamber; and
   positioning said cap in sealing relationship with said base, wherein the multi-compartment capsule is a hard shell capsule.

95. An encapsulation process as defined in claim 94, further comprising the step of reducing dead volume space within said capsule.

96. An encapsulation process as defined in claim 94, wherein said cap comprises a configuration sufficient for reducing dead volume space within said capsule.

97. An encapsulation process as defined in claim 94, wherein said non-excipient ingredient in said first receiving chamber is selected from the group consisting of a pharmaceutical, a biotechnical, a nutraceutical, a vitamin, a dietary supplement and a mineral.

98. An encapsulation process as defined in claim 94, wherein said solid is selected from the group consisting of a pill, a tablet, a capsule, a powder, granulation, flakes, a troche, and a suppository.

99. An encapsulation process as defined in claim 94, wherein said non-excipient ingredient in said second receiving chamber is selected from the group consisting of a pharmaceutical, a biotechnical, a nutraceutical, a vitamin, a dietary supplement and a mineral.

100. An encapsulation process as defined in claim 94, wherein said solid is selected from the group consisting of a pill, a tablet, a capsule, a powder, granulation, flakes, a troche, and a suppository.

101. An encapsulation process as defined in claim 94, wherein said non-excipient ingredient in said first receiving chamber comprises a pharmaceutical and said ingredient in said second receiving chamber is selected from the group consisting of a pharmaceutical.

102. An encapsulation process as defined in claim 94, wherein said non-excipient ingredient in said first receiving chamber comprises a pharmaceutical and said non-excipient ingredient in said second receiving chamber is selected from the group consisting of a biotechnical, a nutraceutical, a vitamin, a dietary supplement and a mineral.

103. An encapsulation process as defined in claim 94, wherein said non-excipient ingredient in said first receiving chamber comprises a pharmaceutical and said non-excipient ingredient in said second receiving chamber is also a pharmaceutical.

104. An encapsulation process as defined in claim 94, wherein said first receiving chamber comprises a time-release coating.

105. An encapsulation process as defined in claim 94 or 104, wherein said second receiving chamber comprises a time-release coating.

106. An encapsulation process as defined in claim 94, further comprising the steps of:
   positioning a second dividing wall along said length of said extending body of said base, said second dividing wall adapted to form a third receiving chamber; and
   introducing at least one ingredient having a physical state into said third receiving chamber.

107. An encapsulation process as defined in claim 106, wherein said ingredient introduced into said third receiving chamber is selected from the group consisting of a pharmaceutical, a biotechnical, a nutraceutical, a vitamin, a dietary supplement and a mineral.

108. An encapsulation process as defined in claim 106, wherein said ingredient introduced into said third receiving chamber is a pharmaceutical.

109. An encapsulation process as defined in claim 106 or 108, wherein all of the ingredients are pharmaceuticals.

110. An encapsulation process as defined in claim 94 or 106, wherein said primary and secondary capsules contain at least one pharmaceutically acceptable lubricant in the range of about 0% to 10% by weight.

111. An encapsulation process as defined in claim 110, wherein said lubricant is selected from the group consisting of aluminiumstearate, calciumstearate, magnesiumstearate, tinstearate, talc, sodium lauryl sulfate, lecithins, mineral oils, stearic acid, silicones and combinations thereof.

* * * * *

(12) SUPPLEMENTAL EXAMINATION CERTIFICATE

United States Patent
Miller

(10) Number: US 7,670,612 F1
(45) Certificate Issued: Oct. 31, 2025

Control No.: 96/050,103
Primary Examiner: Alan Diamond

Filing Date: Sep. 15, 2025

No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| 1,815,902 | 07/28/1931 | Ellzey |
| 5,310,555 | 05/10/1994 | Zimmer |
| 5,501,857 | 03/26/1996 | Zimmer |
| 6,350,468 | 02/26/2002 | Sanso |
| 7,445,795 | 11/04/2008 | Bakhshaee et al. |

FOREIGN PATENT DOCUMENTS

| | | |
|---|---|---|
| WO | 95/16438 A1 | 06/22/1995 |
| DE | 2729068 A1 | 01/11/1979 |
| FR | 2524311 | 10/07/1983 |
| FR | 1454013 | 09/30/1966 |
| GB | 2103564 A | 02/23/1983 |
| GB | 2365336 A | 02/20/2002 |